US011273178B2

(12) United States Patent
Eisenbach et al.

(10) Patent No.: US 11,273,178 B2
(45) Date of Patent: *Mar. 15, 2022

(54) AFFINITY MATURATED T CELL RECEPTORS AND USE THEREOF

(71) Applicant: Yeda Research and Development Co. Ltd., Rehovot (IL)

(72) Inventors: Rachel Lea Eisenbach, Mazkeret Batia (IL); Yosi Gozlan, Rehovot (IL); Esther Tzehoval, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 369 days.

This patent is subject to a terminal disclaimer.

(21) Appl. No.: 16/055,241

(22) Filed: Aug. 6, 2018

(65) Prior Publication Data

US 2019/0031733 A1   Jan. 31, 2019

Related U.S. Application Data

(60) Division of application No. 13/958,277, filed on Aug. 2, 2013, now Pat. No. 10,081,663, which is a continuation of application No. PCT/IL2012/000061, filed on Feb. 5, 2012.

(60) Provisional application No. 61/439,894, filed on Feb. 6, 2011.

(51) Int. Cl.
| | |
|---|---|
| *A61K 35/17* | (2015.01) |
| *C07K 14/725* | (2006.01) |
| *C12N 15/10* | (2006.01) |
| *C12N 15/63* | (2006.01) |
| *C12N 15/85* | (2006.01) |
| *C12N 5/0783* | (2010.01) |
| *C12N 5/10* | (2006.01) |
| *C07K 14/705* | (2006.01) |

(52) U.S. Cl.
CPC .......... *A61K 35/17* (2013.01); *C07K 14/7051* (2013.01); *C07K 14/70503* (2013.01); *C12N 5/0636* (2013.01); *C12N 5/10* (2013.01); *C12N 15/102* (2013.01); *C12N 15/63* (2013.01); *C12N 15/85* (2013.01); *C12N 2840/20* (2013.01)

(58) Field of Classification Search
CPC .............. A61K 35/17; C07K 14/70503; C07K 14/7051; C12N 5/0636; C12N 5/10; C12N 15/102; C12N 15/63; C12N 15/85; C12N 2840/20
USPC .......... 424/93.21, 93.71; 435/372.3, 440, 455
See application file for complete search history.

(56) References Cited

U.S. PATENT DOCUMENTS

| | | | |
|---|---|---|---|
| 7,569,357 B2 | 8/2009 | Kranz et al. | |
| 10,081,663 B2 * | 9/2018 | Eisenbach ........ | C07K 14/70503 |
| 2006/0099679 A1 | 5/2006 | Tsien et al. | |
| 2009/0054257 A1 | 2/2009 | Dunn et al. | |
| 2012/0151613 A1 | 6/2012 | Wang et al. | |
| 2014/0065111 A1 | 3/2014 | Eisenbach et al. | |
| 2019/0321478 A1 | 10/2019 | Alten et al. | |

FOREIGN PATENT DOCUMENTS

| | | | |
|---|---|---|---|
| EP | 2414507 | | 2/2012 |
| WO | 2003/061363 | * | 7/2003 |
| WO | WO 03/061363 | | 7/2003 |
| WO | 2006/053021 | * | 5/2006 |
| WO | WO 2006/053021 | | 5/2006 |
| WO | WO 2008/103474 | | 8/2008 |
| WO | WO 2008/103475 | | 8/2008 |
| WO | WO 2010/132092 | | 11/2010 |
| WO | WO 2012/104843 | | 8/2012 |
| WO | WO 2014/118236 | | 8/2014 |
| WO | WO 2020/037239 | | 2/2020 |

OTHER PUBLICATIONS

Zhao et al. (2007) J. Immunol., vol. 179(9), 5845-5854.*
Robbins et al. (2011) J. Clin. Oncology, vol. 29 (7), 917-924, published online Jan. 31, 2011.*
Robbins et al. (2008) J. Immunol., vol. 180,6116-6131, hereafter referred to as Robbins 2008.*
Restifo et al. (2012) Nat. Rev. Immunol., vol. 12, 269-281.*
Advisory Action Before the Filing of An Appeal Brief dated Jun. 21, 2017 From the US Patent and Trademark Office Re. U.S. Appl. No. 13/958,277. (8 pages).
International Preliminary Report on Patentability dated Aug. 6, 2013 From the International Bureau of WIPO Re. Application No. PCT/IL2012/000061.
International Search Report and the Written Opinion dated Jul. 5, 2012 From the International Searching Authority Re. Application No. PCT/IL2012/000061.
Notice of Allowance dated Jun. 20, 2018 From the US Patent and Trademark Office Re. U.S. Appl. No. 13/958,277. (10 pages).
Official Action dated Jul. 1, 2015 From the US Patent and Trademark Office Re. U.S. Appl. No. 13/958,277.
Official Action dated Jul. 6, 2016 From the US Patent and Trademark Office Re. U.S. Appl. No. 13/958,277.
Official Action dated Feb. 17, 2016 From the US Patent and Trademark Office Re. U.S. Appl. No. 13/958,277.

(Continued)

*Primary Examiner* — Anne Marie S Wehbe

(57) ABSTRACT

The present invention relates to methods and systems for increasing the affinity of a T cell receptor (TCR) to its ligand by subjecting the TCR gene to somatic hypermutation. The present invention further relates to use of affinity maturated TCRs to create T cells reactive against a selected antigen.

6 Claims, 48 Drawing Sheets

Specification includes a Sequence Listing.

(56) References Cited

OTHER PUBLICATIONS

Official Action dated Feb. 23, 2017 From the US Patent and Trademark Office Re. U.S. Appl. No. 13/958,277. (13 pages).
Official Action dated Dec. 28, 2017 From the US Patent and Trademark Office Re. U.S. Appl. No. 13/958,277. (12 pages).
Alajez et al. "Therapeutic Potential of A Tumor-Specific, MHC-Unrestricted T-Cell Receptor Expressed on Effector Cells of the Innate and the Adaptive Immune System Through Bone Marrow Transduction and Immune Reconstitution", Blood, 105(12): 4583-4589, Published Online Mar. 3, 2005.
Arakawa et al. "Requirement of the Activation-Induced Deaminase (AID) Gene for Immunoglobulin Gene Conversion", Science, 295(5558): 1301-1306, Feb. 15, 2002.
Bachl et al. "Increased Transcription Levels Induce Higher Mutation Rates in A Hypermutating Cell Line", The Journal of Immunology, 166(8): 5051-5057, Apr. 15, 2001.
Besmer et al. "The Transcription Elongation Complex Directs Activation-Induced Cytidine Deaminase-Mediated DNA Deamination", Molecular and Cellular Biology, 26(11): 4378-4385, Jun. 2006.
Brar et al. "Activation Induced Cytosine Deaminase (AID) Is Actively Exported Out of the Nucleus But Retained by the Induction of DNA Breaks", The Journal of Biological Chemistry, 279(25): 26395-26401, Published Online Apr. 15, 2004.
Carson et al. "Six Chains of the Human T Cell Antigen Receptor•CD3 Complex Are Necessary and Sufficient for Processing the Receptor Heterodimer to the Cell Surface", The Journal Of Biological Chemistry,266(12): 7883-7887, Apr. 25, 1991.
Chang et al. "Phase II Trial of Autologous Tumor Vaccination, Anti-CD3-Activated Vaccine-Primed Lymphocytes, and Interleukin-2 in Stage IV Renal Cell Cancer", Journal of Clinical Oncology, 21(5): 884-890, Mar. 1, 2003.
Chen et al. "Affinity Maturation of Anti-TNF-Alpha ScFv With Somatic Hypermutation in Non-B Cells", Protein & Cell, 3(6): 460-469, Published Online Apr. 1, 2012.
Chervin et al. "Engineering Higher Affinity T Cell Receptors Using A T Cell Display System", Journal of Immunological Methods, 339(2): 175-184, Dec. 31, 2008.
Cooper et al. "T-Cell Clones Can Be Rendered Specific for CD19: Toward the Selective Augmentation of the Graft-Versus-B-Lineage Leukemia Effect", Blood, 101(4): 1637-1644, Published Online Oct. 10, 2002.
Dudley et al. "Adoptive Cell Transfer Therapy Following Non-Myeloablative But Lymphodepleting Chemotherapy for the Treatment of Patients With Refractory Metastatic Melanoma", Journal of Clinical Oncology, 23(10): 2346-2357, Apr. 1, 2005.
Dudley et al. "Cancer Regression and Autoimmunity in Patients After Clonal Repopulation With Antitumor Lymphocytes", Science, 298(5594): 850-854, Oct. 25, 2002.
Dudley et al. "Generation of Tumor-Infiltrating Lymphocyte Cultures for Use in Adoptive Transfer Therapy for Melanoma Patients", Journal of Immunotherapy, 26(4): 332-342, 2003.
Fang et al. "Stable Antibody Expression at Therapeutic Levels Using the 2A Peptide", Nature Biotechnology, 23(5): 584-590, May 5, 2005.
Finkelstein et al. "Bedside to Bench and Back Again: How Animal Models are Guiding the Development of New Immunotherapies for Cancer", Journal of Leukocyte Biology, 76(2): 333-337, Aug. 2004.
Holler et al. "In Vitro Evolution of A T Cell Receptor With High Affinity for Peptide/MHC", Proc. Natl. Acad. Sci. USA, PNAS, 97(10): 5387-5391, May 9, 2000.
Holler et al. "Quantitative Analysis of the Contribution of TCR/PepMHC Affinity and CD8 to T Cell Activation", Immunity, 18(2): 255-264, Feb. 2003.
Hooijberg et al. "Immortalization of Human CD8+ T Cell Clones by Ectopic Expression of Telomerase Reverse Transcriptase", The Journal of Immunology, 165(8): 4239-4245, Oct. 2000.

Hughes et al. "Transfer of A TCR Gene Derived From A Patient With A Marked Antitumor Response Conveys Highly Active T-Cell Effector Functions", Human Gene Therapy, 16(4): 457-472, Apr. 2005.
Hunder et al. "Treatment of Metastatic Melanoma With Autologous CD4+ T Cells Against NY-ESO-1", The New England Journal of Medicine, 358(25): 2698-2703, Jun. 19, 2008.
Ito et al. "Activation-Induced Cytidine Deaminase Shuttles Between Nucleus and Cytoplasm Like Apolipoprotein B mRNA Editing Catalytic Polypeptide 1", Proc. Natl. Acad. Sci. USA, PNAS, 101(7): 1975-1980, Feb. 17, 2004.
June "Principles of Adoptive T Cell Cancer Therapy", The Journal of Clinical Investigation, 117(5): 1204-1212, May 2007.
Kershaw et al. "A Phase I Study on Adoptive Immunotherapy Using Gene-Modified T Cells for Ovarian Cancer", Clinical Cancer Research,12(20 Pt. 1): 6106-6115, Oct. 15, 2006.
Kieback et al. "Enhanced T Cell Receptor Gene Therapy for Cancer", Expert Opinion on Biological Therapy, 10(5): 749-762, May 1, 2010.
Kieke et al. "Selection of Functional T Cell Receptor Mutants From A Yeast Surface-Display Library", Proc. Natl. Acad. Sci. USA, XP002177390, 96(10): 5651-5656, May 11, 1999.
Klebanoff et al. "Central Memory Self/Tumor-Reactive CD8+ T Cells Confer Superior Antitumor Immunity Compared With Effector Memory T Cells", Proc. Natl. Acad. Sci. USA, PNAS, 102(27): 9571-9576, Jul. 5, 2005.
Kotani et al. "A Target Selection of Somatic Hypermutations Is Regulated Similary Between T and B Cells Upon Activation-Induced Cytidine Deaminase Expression", Proc. Natl. Acad. Sci. USA, PNAS, XP002677718, 102(12): 4506-4511, Mar. 22, 2005.
Lamers et al. "Treatment of Metastatic Renal Cell Carcinoma With Autologous T-Lymphocytes Genetically Retargeted Against Carbonic Anhydrase IX: First Clinical Experience", Journal of Clinical Oncology, 24(13): e20-e22, May 1, 2006.
Lazarides et al. "Actin Is the Naturally Occurring Inhibitor of Deoxyribonuclease I", Proc. Natl. Acad. Sci. USA, PNAS, 71(12): 4742-4746, Dec. 1, 1974.
Lederberg "Genes and Antibodies", Science, 129(3364): 1649-1653, Jun. 19, 1959.
Mackensen et al. "Phase I Study of Adoptive T-Cell Therapy Using Antigen-Specific CD8+ T Cells for the Treatment of Patients With Metastatic Melanoma", Journal of Clinical Oncology, 24(31): 5060-5069, Nov. 1, 2006.
Maul et al. "Aid And Somatic Hypermutation", Advances in Immunology, 105: 159-191, Dec. 31, 2010.
McBride et al. "Somatic Hypermutation Is Limited by CRM 1-Dependent Nuclear Export of Activation-Induced Deaminase", The Journal of Experimental Medicine, 199(9): 1235-1244, May 3, 2004.
Michael et al. "The E Box Motif CAGGTG Enhances Somatic Hypermutation Without Enhancing Transcription", Immunity, 19(2): 235-242, Aug. 31, 2003.
Morgan et al. "Cancer Regression in Patients After Transfer of Genetically Engineered Lymphocytes", Science, 314(5796): 126-129, Oct. 6, 2006.
Muramatsu et al. "Class Switch Recombination and Hypermutation Require Activation-Induced Cytidine Deaminase (AID), A Potential RNA Editing Enzyme", Cell, 102(5): 553-563, Sep. 1, 2000.
Muramatsu et al. "Specific Expression of Activation-Induced Cytidine Deaminase (AID), A Novel Member of the RNA-Editing Deaminase Family in Germinal Center B Cells", The Journal of Biological Chemistry, 274(26): 18470-18476, Jun. 25, 1999.
Odegard et al. "Targeting of Somatic Hypermutation", ONature Reviews, 6(8): 573-583, Aug. 1, 2006.
Ogg et al. "HLA-Peptide Tetrameric Complexes", Current Opinion in Immunology, 10(4): 393-396, Aug. 31, 1998.
Overwijk "Tumor Regression and Autoimmunity After Reversal of A Functionally Tolerant State of Self-Reactive CD8+ T Cells", The Journal of Experimental Medicine, 198(4): 569-580, Aug. 18, 2003.
Overwijk et al. "GP100/Pmel 17 Is A Murine Tumor Rejection Antigen: Induction of 'Self'-Reactive, Tumoricidal T Cells Using High-Affinity, Altered Peptide Ligand", The Journal of Experimental Medicine, 188(2): 277-286, Jul. 20, 1998.

(56) References Cited

OTHER PUBLICATIONS

Park et al. "Adoptive Transfer of Chimeric Antigen Receptor Re-Directed Cytolytic T Lymphocyte Clones in Patients With Neuroblastoma", Molecular Therapy,15(4): 825-833, Apr. 1, 2007.
Powell et al. "Transition of Late-Stage Effector T Cells to CD27+ CD28+ Tumor-Reactive Effector Memory T Cells in Humans After Adoptive Cell Transfer Therapy", Blood, 105(1): 241-250, Jan. 1, 2005.
Qin et al. "Activation-Induced Cytidine Deaminase Expression in CD4+ T Cells Is Associated With A Unique IL-10-Producing Subset That Increases With Age", PLoS One, XP002677720, 6(12): e29141-1-e29141-15, Dec. 28, 2011.
Rajewsky et al. "Evolutionary and Somatic Selection of the Antibody Repertoire in the Mouse", Science, 238(4830): 1088-1094, Nov. 20, 1987.
Roszkowski et al. "Simultaneous Generation of CD8+ and CD4+ Melanoma-Reactive T Cells by Retrovirai-Mediated Transfer of A Single T-Cell Receptor", Cancer Research, 65(4):1570-1576, Feb. 15, 2005.
Shen et al. "The Activation-Induced Cytidine Deaminase (AID) Efficiently Targets DNA in Nucleosomes But Only During Transcription", The Journal of Experimental Medicine, 206(5): 1057-1071, May 11, 2009.
Spiotto et al. "Bystander Elimination of Antigen Loss Variants in Established Tumors", Nature Medicine, 10(3): 294-298, Mar. 1, 2004.
Storb et al. "Targeting of AID to Immunoglobulin Genes", Mechanisms of Lymphocyte Activation and Immune Regulation XI, Advances in Experimental Medicine and Biology, 596(Chap.8): 83-91, Jan. 1, 2007.
Szymczak et al. "Correction of Multi-Gene Deficiency in Vivo Using A Single 'Self-Cleaving' 2A Peptide-Based Retroviral Vector", Nature Biotechnology, 22(5): 589-594, May 1, 2004.
Tanaka et al. "Attracting AID to Targets of Somatic Hypermutation", The Journal of Experimental Medicine, 207(2): 405-415, Jan. 25, 2010.
Teng et al. "Immunoglobulin Somatic Hypermutation", Annual Review of Genetics, 41: 107-120, Dec. 1, 2007.
Topp et al. "Restoration of CD28 Expression in CD28-CD8+ Memory Effector T Cells Reconstitutes Antigen-Induced IL-2 Production", Journal of Experimental Medicine, 198(6): 947-955, Sep. 15, 2003.

Weber et al. "Class II-Restricted T Cell Receptor Engineered In Vitro for Higher Affinity Retains Peptide Specificity and Function", Proc. Natl. Acad. Sci. USA, PNAS, 102(52): 19033-19038, Dec. 27, 2005.
Yang et al. "Neutralization of Multiple Staphylococcal Superantigens by A Single-Chain Protein Consisting of Affinity-Matured, Variable Domain Repeats", Journal of Infectious Diseases, 198(3): 344-348, Aug. 1, 2008.
Yee et al. "Adoptive T Cell Therapy Using Antigen-Specific CD8+ T Cell Clones for the Treatment of Patients With Metastatic Melanoma: In Vivo Persistence, Migration, and Antitumor Effect of Transferred T Cells", Proc. Natl. Acad. Sci. USA, PNAS, 99(25): 16168-16173, Dec. 10, 2002.
Yee et al. "Melanocyte Destruction After Antigen-Specific Immunotherapy of Melanoma: Direct Evidence of T Cell-Mediated Vitiligo", The Journal of Experimental Medicine, 192(11): 1637-1643, Dec. 4, 2000.
Zhao et al. "High-Affinity TCRs Generated by Phage Display Provide CD4+ T Cells With the Ability to Recognize and Kill Tumor Cell Lines", The Journal of Immunology, 179(9): 5845-5854, Nov. 1, 2007.
Office Action and Search Report dated Apr. 21, 2021 From the Israel Patent Office Re. Application No. 276599. (11 Pages).
Bassan et al. "Optimizing T Cell Receptor Avidity With Somatic Hypermutation", International Journal of Cancer, 145(10): 2816-2826, Published Online Aug. 5, 2019.
Wang et al. "AID Upmutants Isolated Using A High-Throughput Screen Highlight the Immunity/Cancer Balance Limiting DNA Deaminase Activity", Natural Structural & Molecular Biology, 16(7): 769-777, Published Online Jun. 21, 2009.
Invitation to Pay Additional Fees, Communication Relating to the Results of the Partial International Search and the Provisional Opinion Dated Dec. 10, 2021 From the International Searching Authority Re. Application No. PCT/IL2021/050959. (16 Pages).
Bassan et al. "Avidity Optimization of A MAGE-A1-Specific TCR With Somatic Hypermutation", European Journal of Immunology, XP055859787, 51(6): 1505-1518, Published Online May 5, 2021.
Obenaus et al. "Identification of Human T-Cell Receptors With Optimal Affinity to Cancer Antigens Using Antigen-Negative Humanized Mice", Nature Biotechnology, XP055212602, 33(4): 402-407, Published Online Mar. 16, 2015.
Weon et al. "The MAGE Protein Family and Cancer", Current Opinion in Cell Biology, XP029343219, 37: 1-8, Published Online Sep. 3, 2015.

* cited by examiner

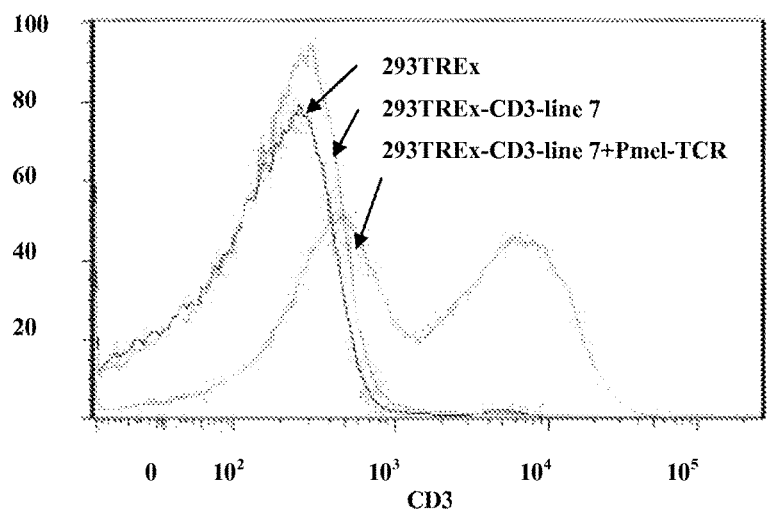
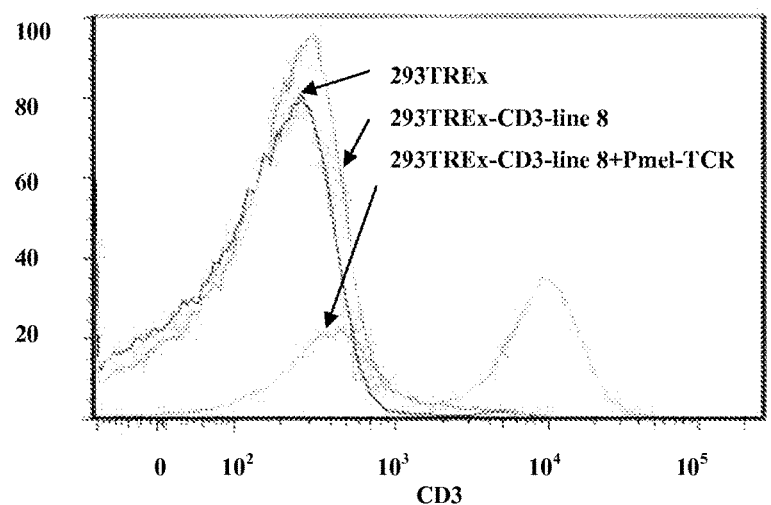
Figure 6B
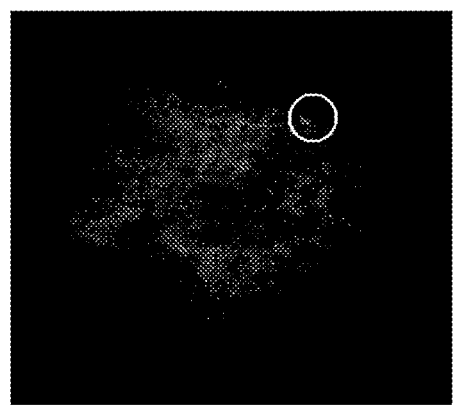
Figure 7

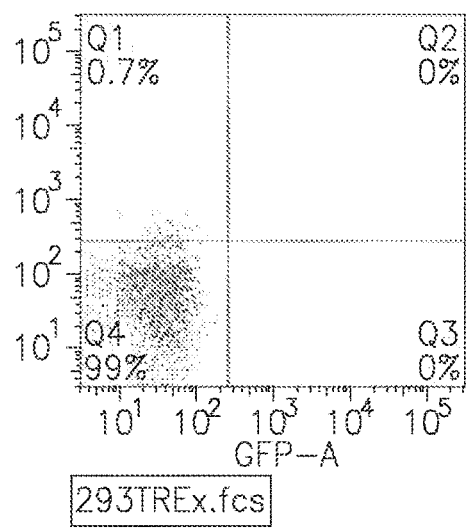
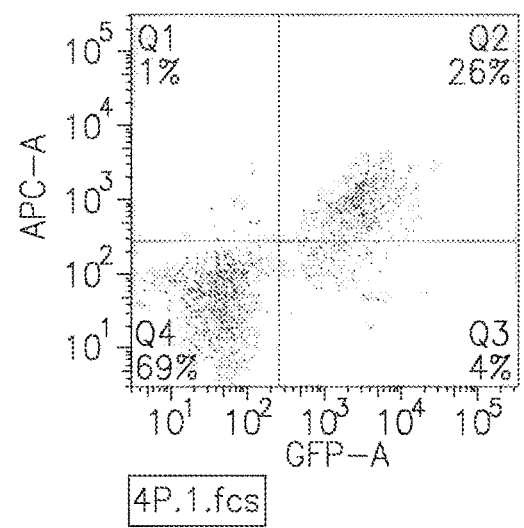
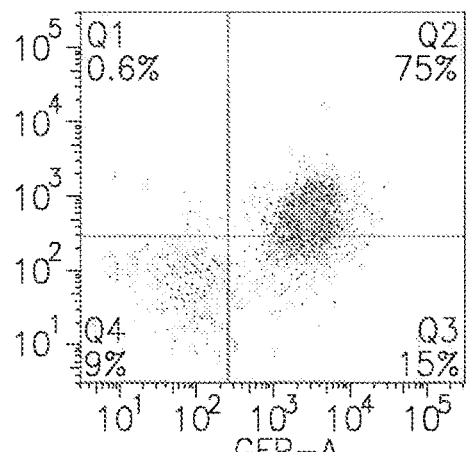
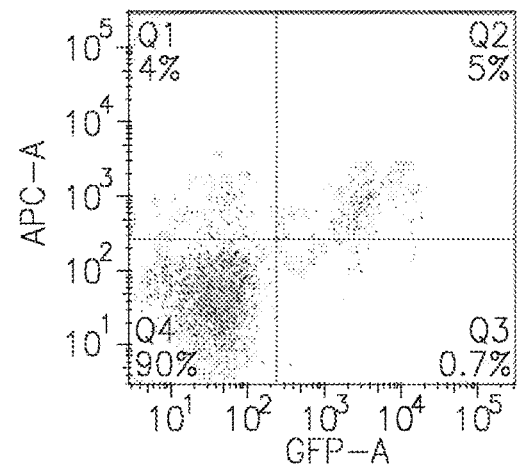
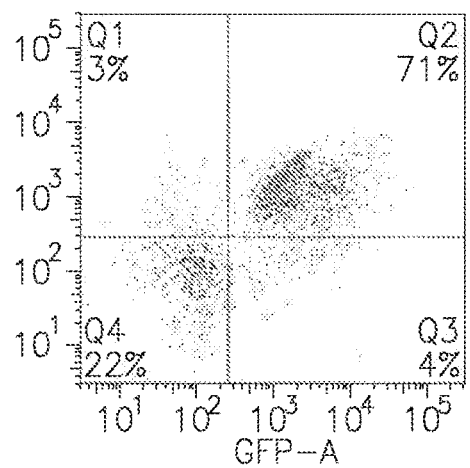
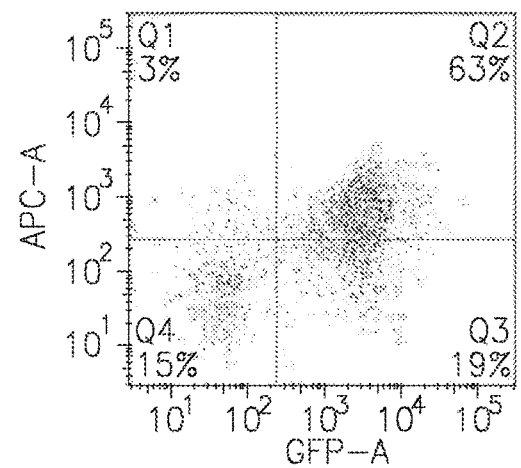
FIG.11

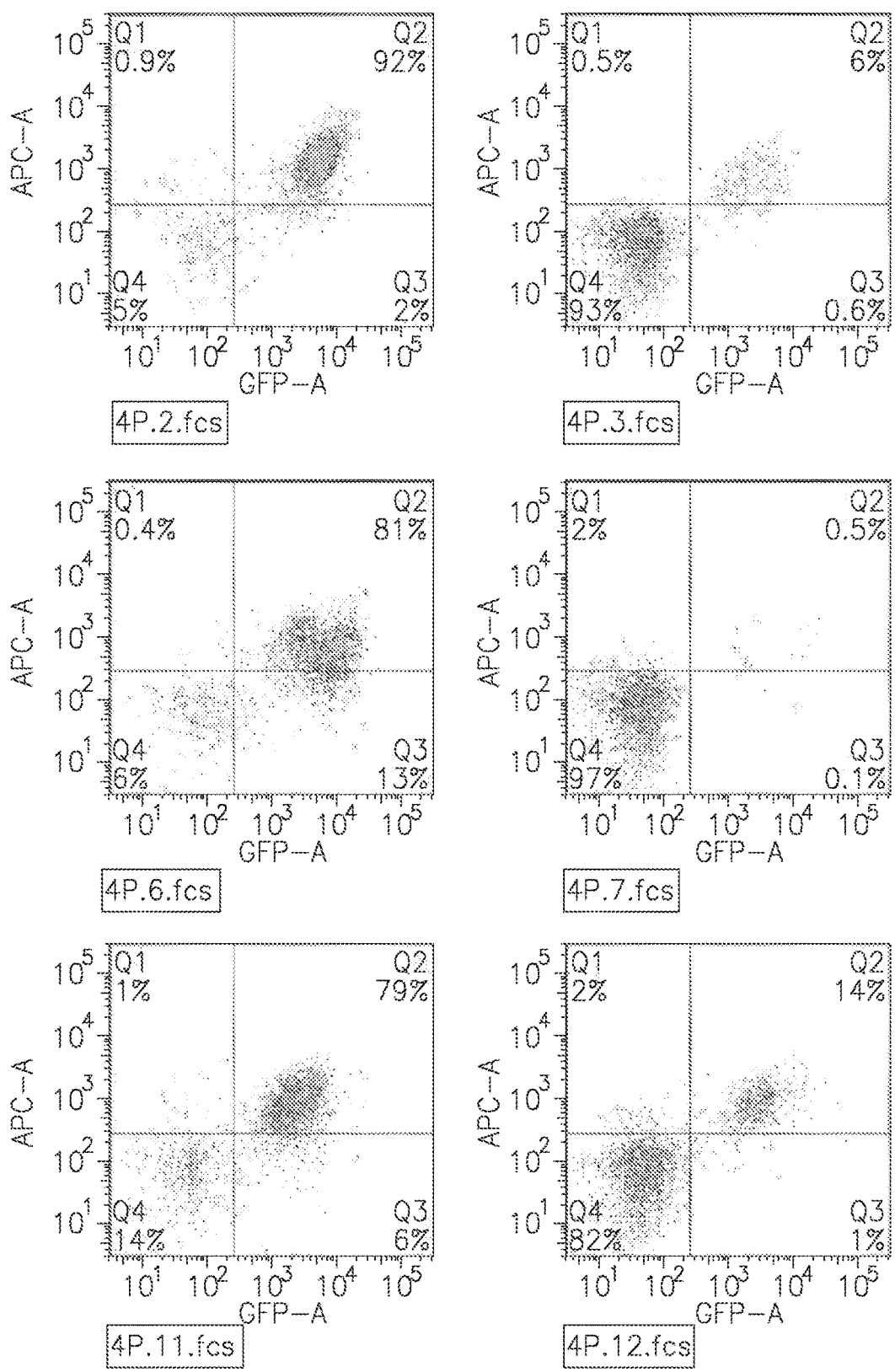
FIG.11 (cont. 1)

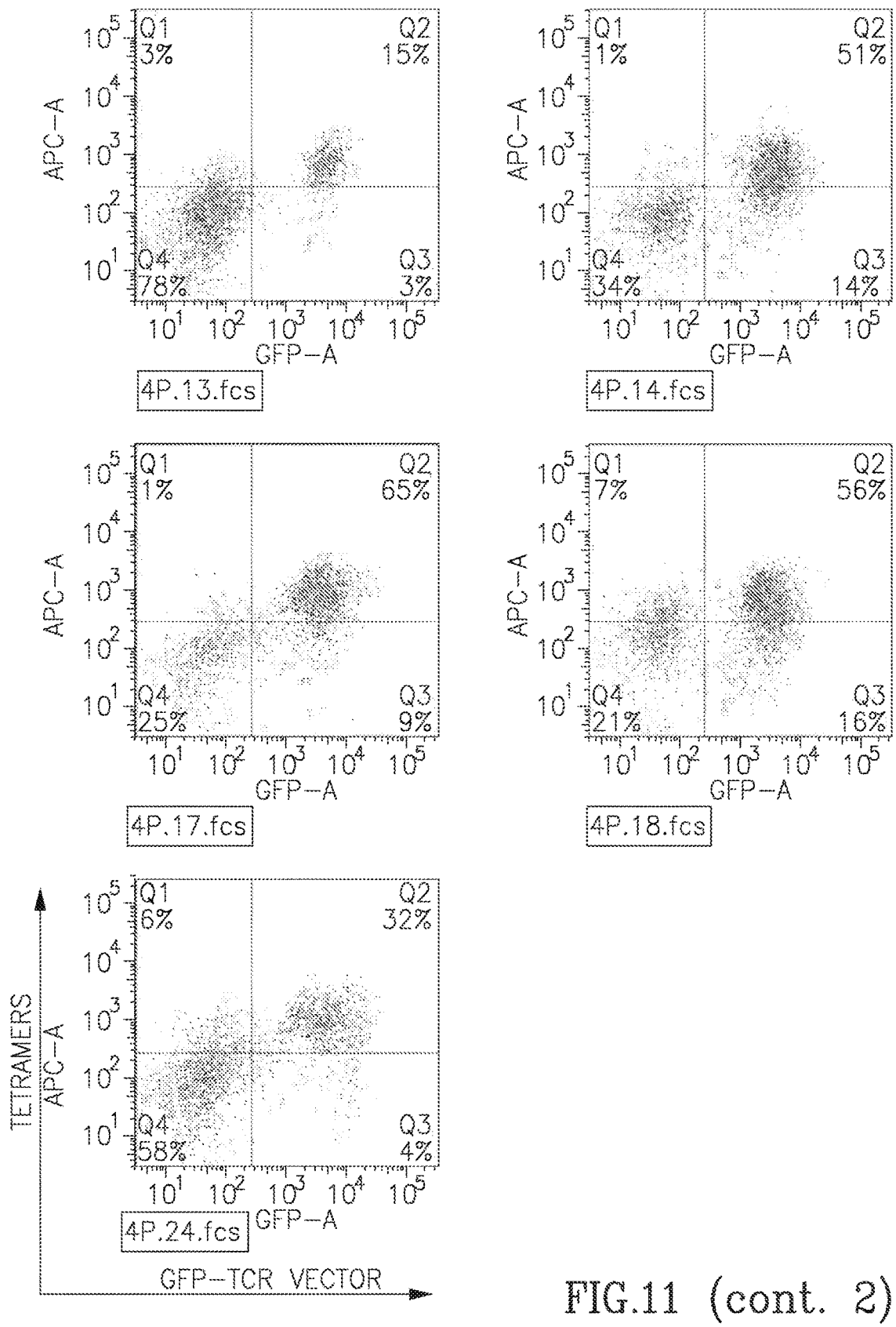
FIG.11 (cont. 2)

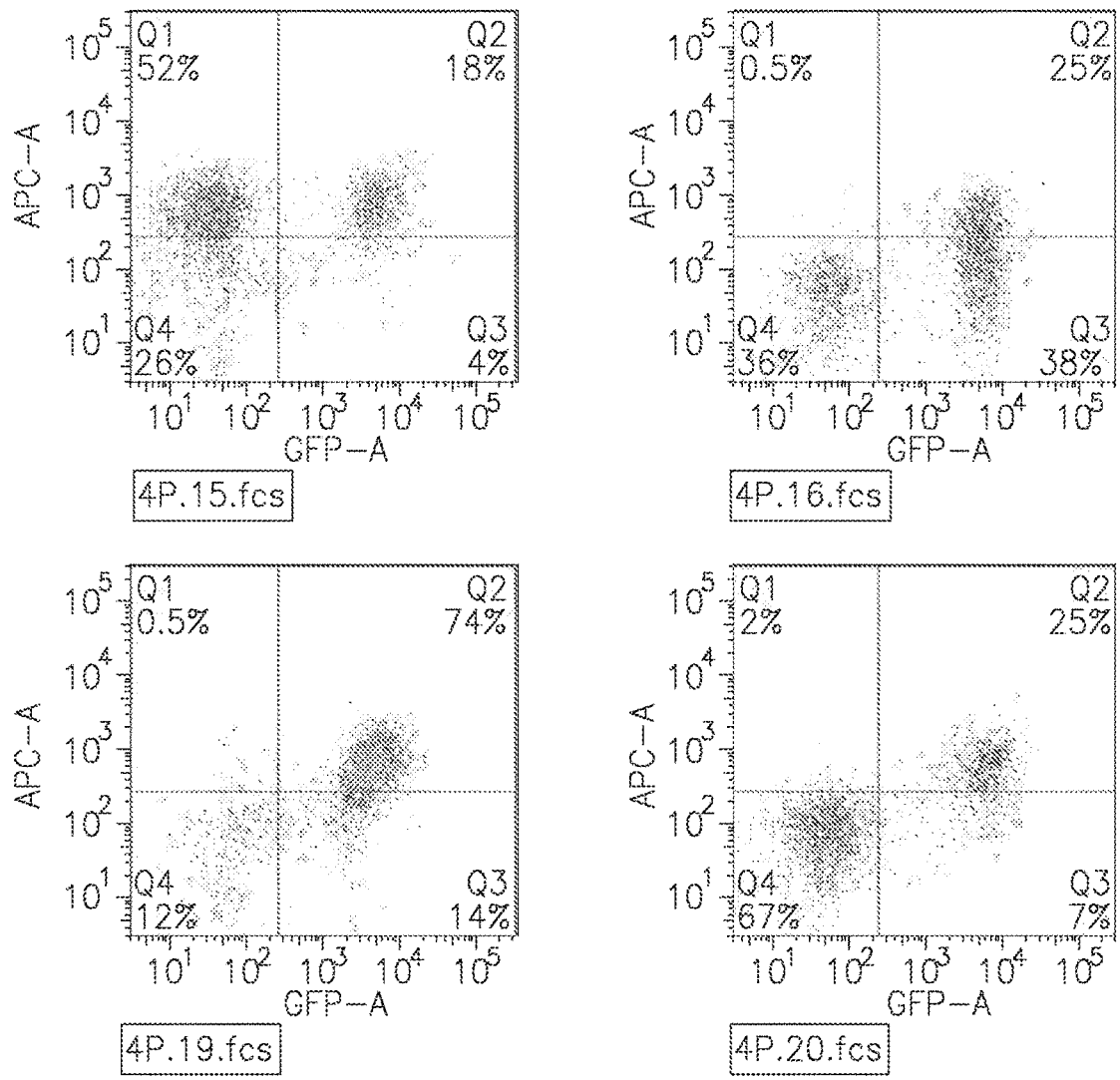
FIG.11 (cont. 3)

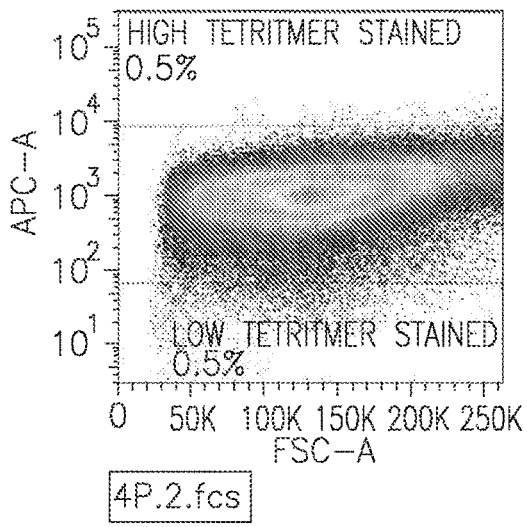
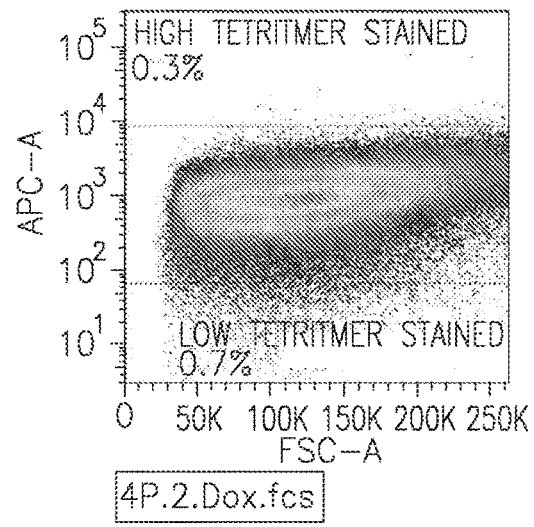
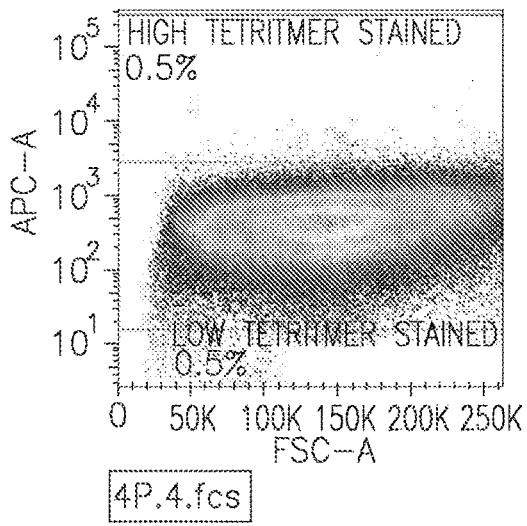
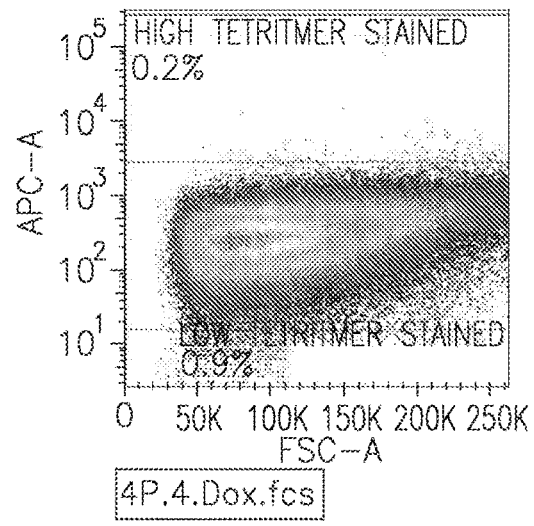
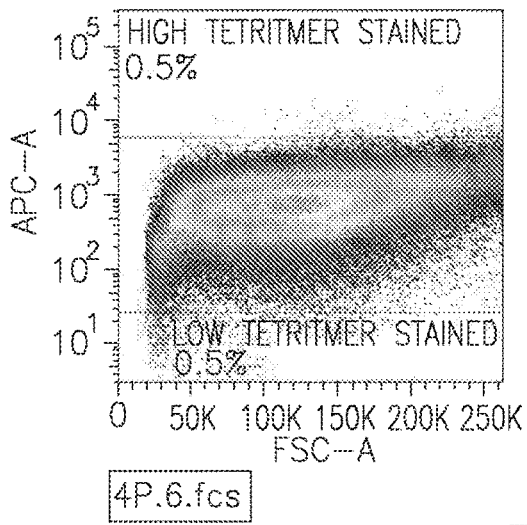
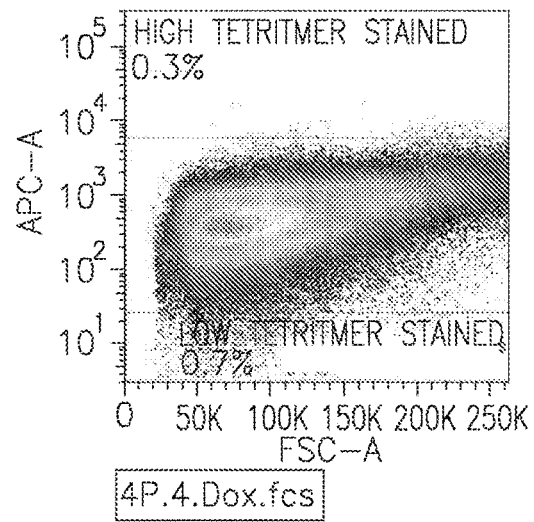
FIG.12

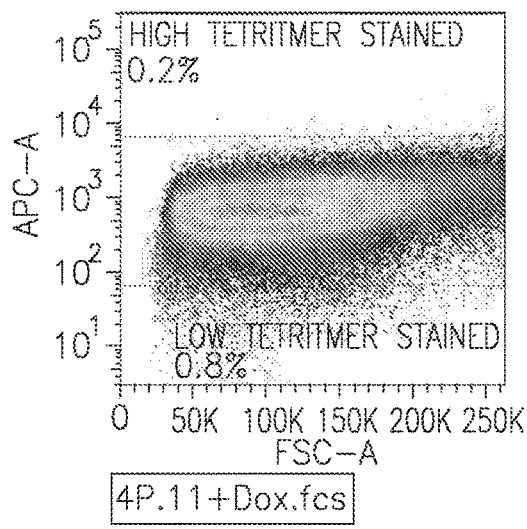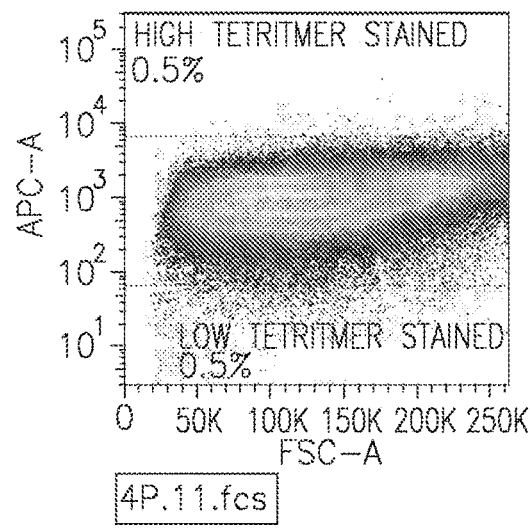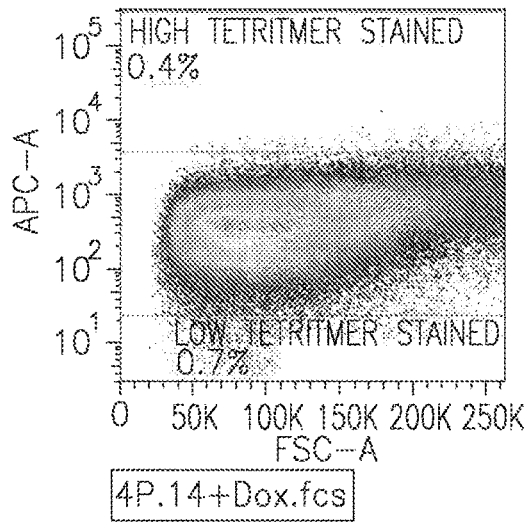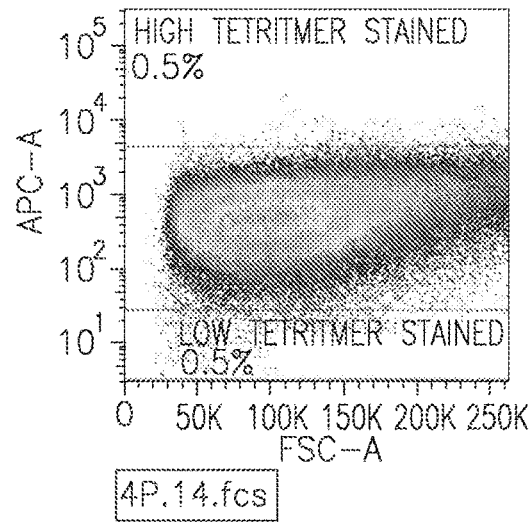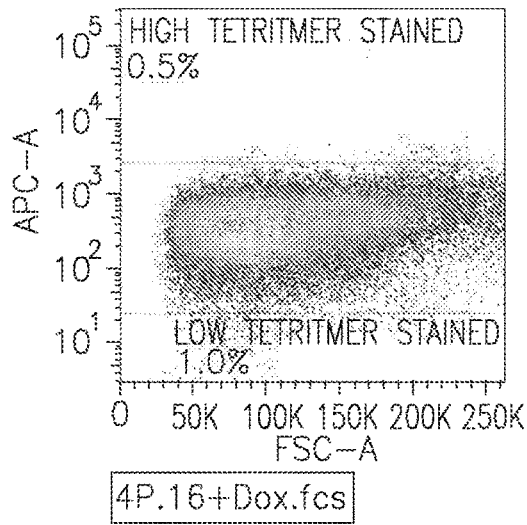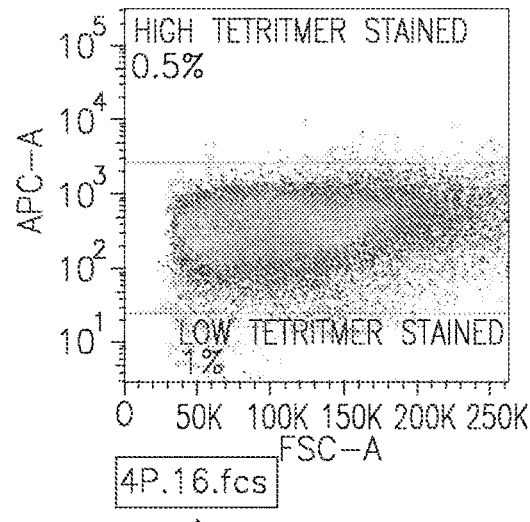
FIG.12 (cont. 1)

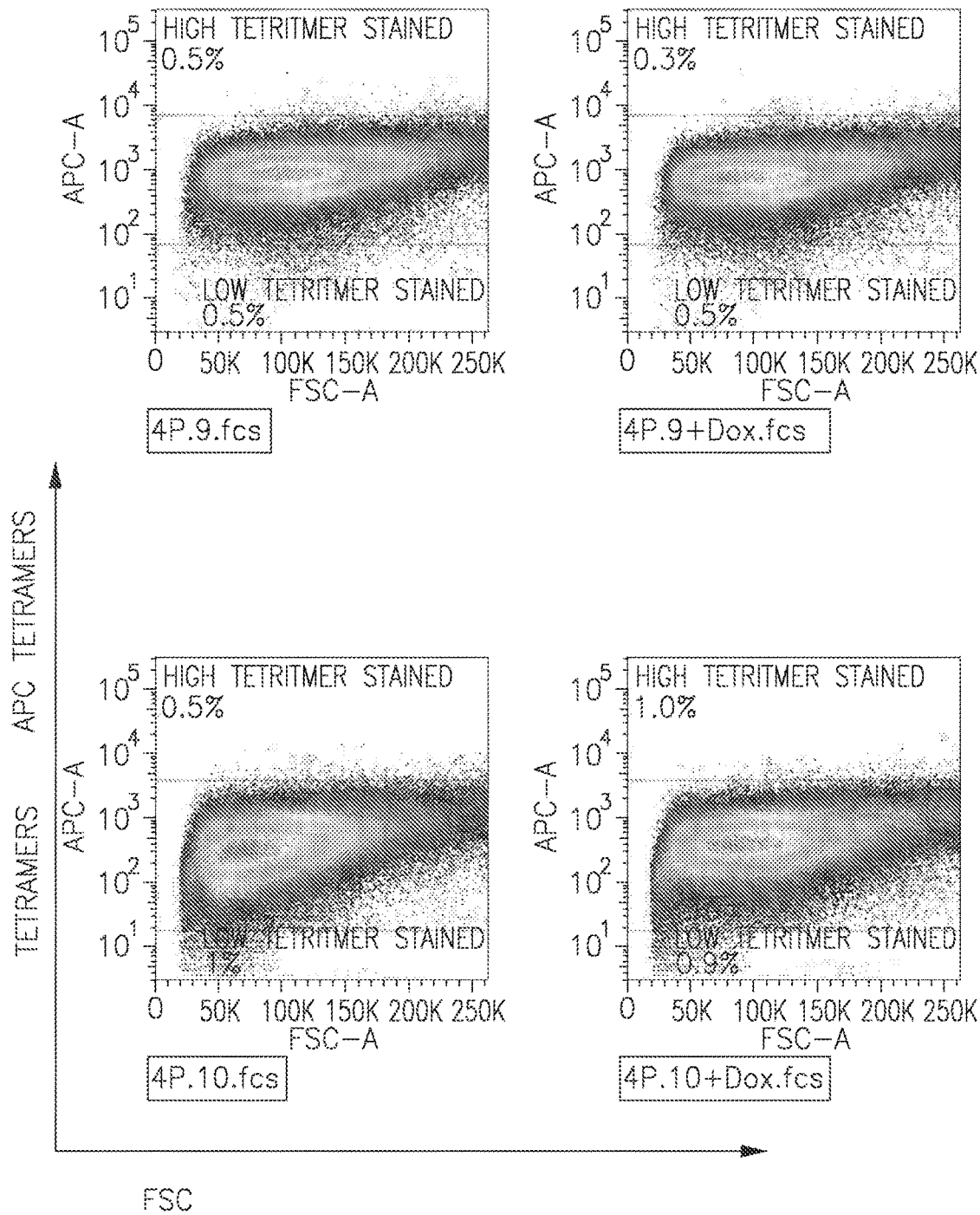
FIG.12 (cont. 2)

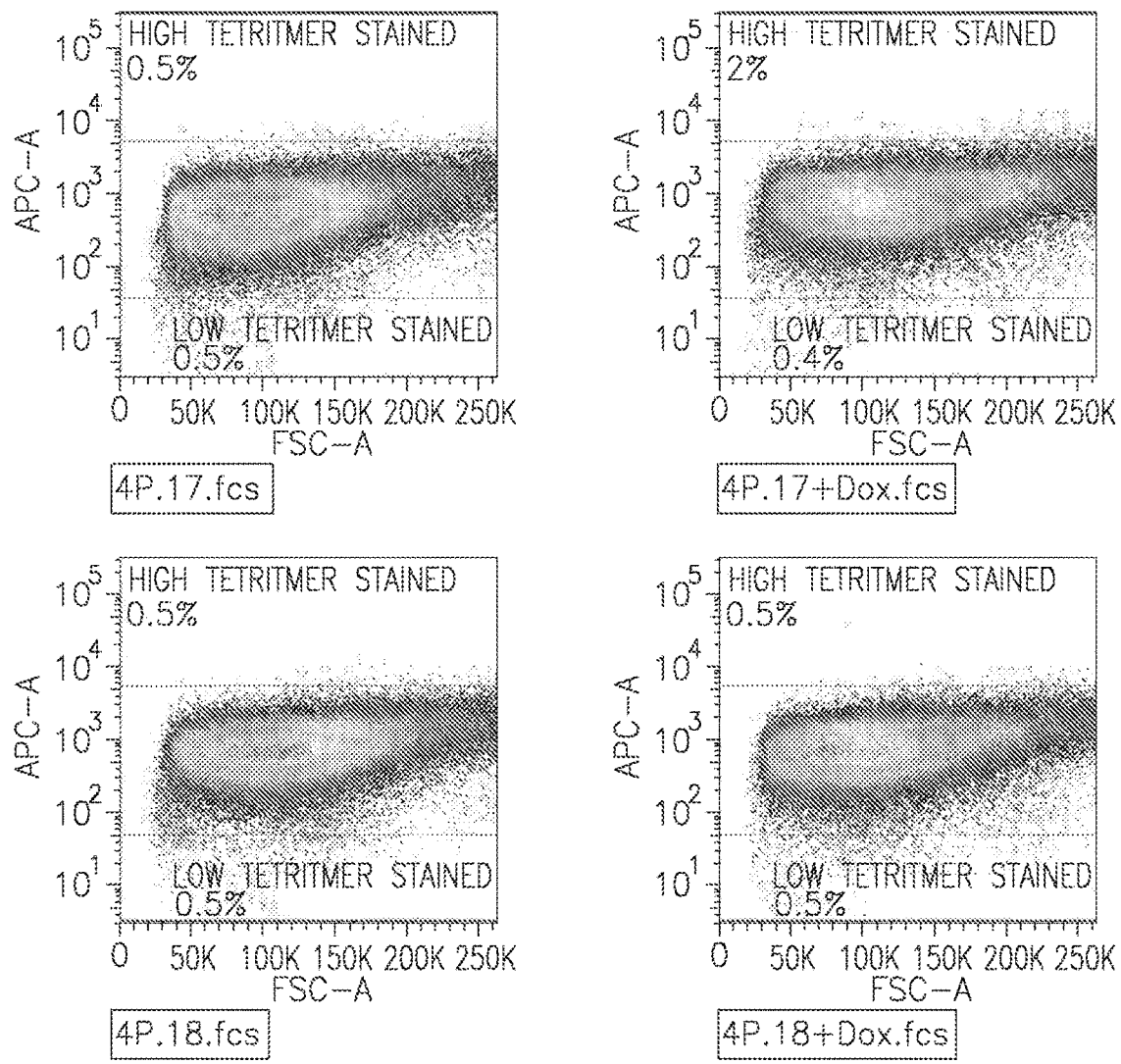
FIG.12 (cont. 3)

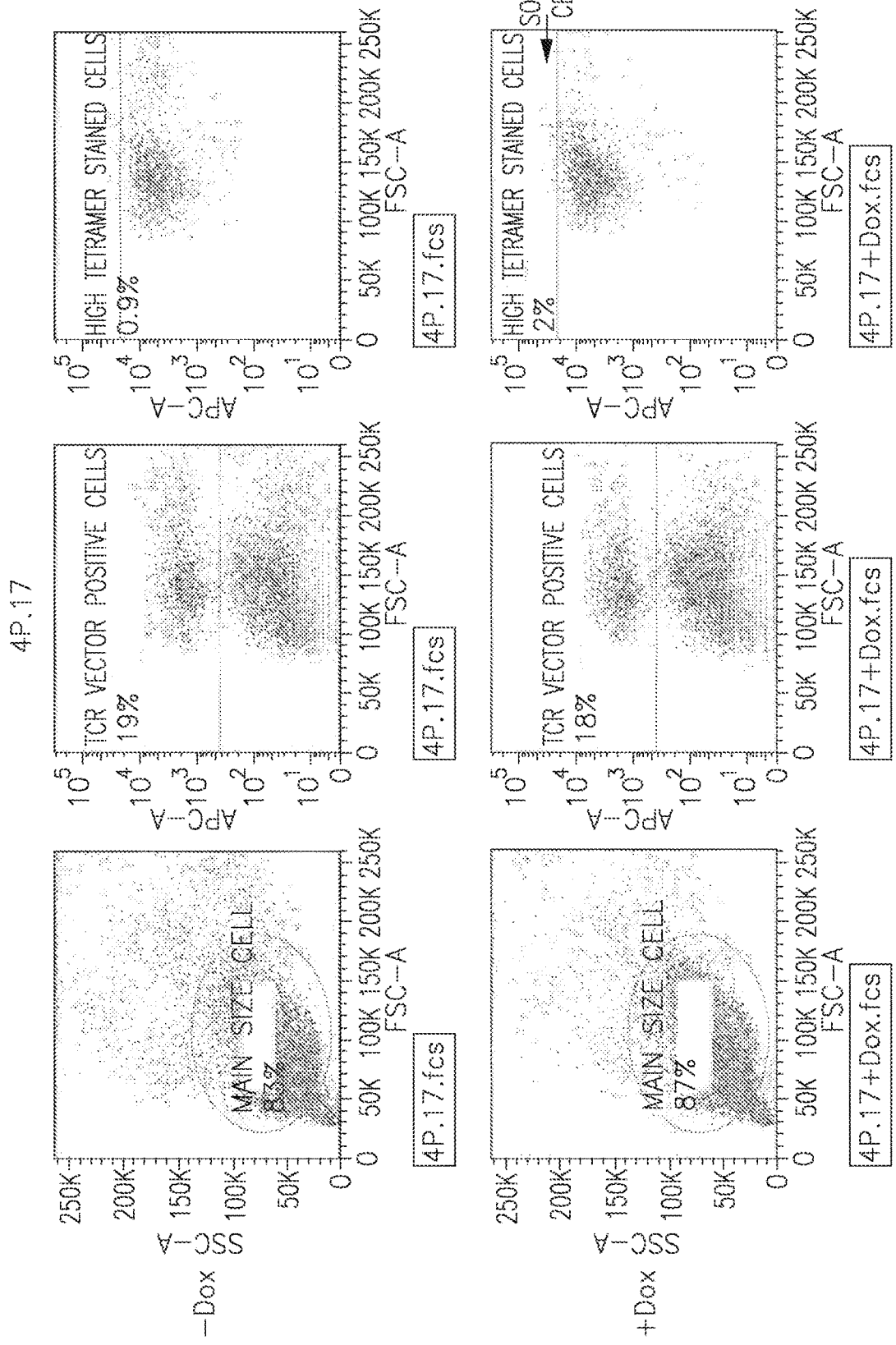
FIG. 13 (cont. 1)

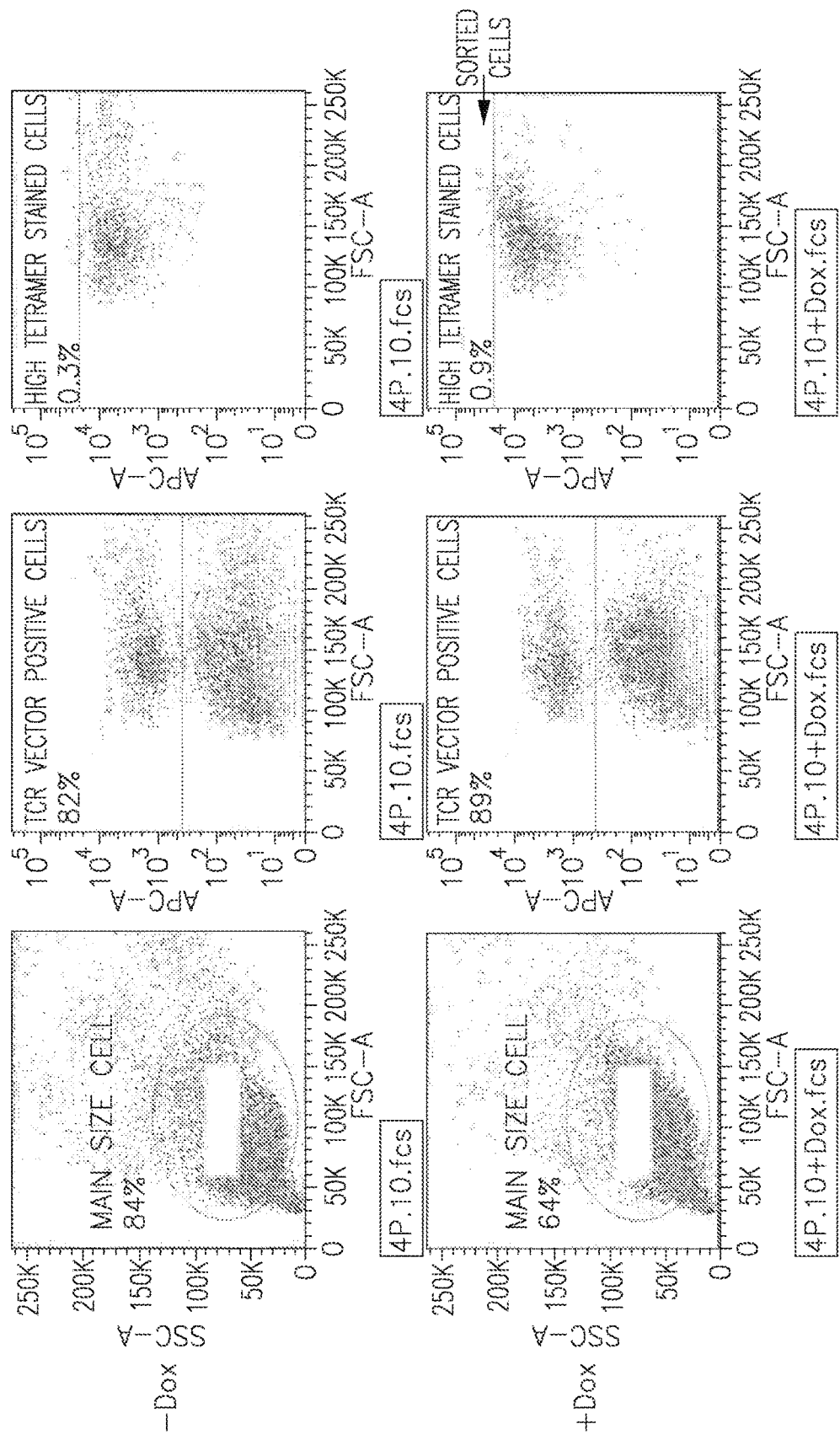
FIG. 13 (cont. 2)

CD3 delta chain mRNA cds: gi|227498960: (SEQ ID NO: 16)

ATGGAACACAGCGGGATTCTGGCTAGTCTGATACTGATTGCTGTTCTCCCCCAAGGGAGCC
CCTTCAAGATACAAGTGACCGAATATGAGGACAAAGTATTTGTGACCTGCAATACCAGCG
TCATGCATCTAGATGGAACGGTGGAAGGATGGTTTGCAAAGAATAAAACACTCAACTTGG
GCAAAGGCGTTCTGGACCCACGAGGGATATATCTGTGTAATGGGACAGAGCAGCTGGCAA
AGGTGGTGTCTTCTGTGCAAGTCCATTACCGAATGTGCCAGAACTGTGTGGAGCTAGACTC
GGGCACCATGGCTGGTGTCATCTTCATTGACCTCATCGCAACTCTGCTCCTGGCTTTGGGC
GTCTACTGCTTTGCAGGACATGAGACCGGAAGGCCTTCTGGGGCTGCTGAGGTTCAAGCA
CTGCTGAAGAATGAGCAGCTGTATCAGCCTCTTCGAGATCGTGAAGATACCCAGTACAGC
CGTCTTGGAGGGAACTGGCCCCGGAACAAGAAATCTTAA

CD3 epsilon chain mRNA cds: gi|158508719:79-648 (SEQ ID NO: 17)

ATGCGGTGGAACACTTTCTGGGGCATCCTGTGCCTCAGCCTCCTAGCTGTTGGCACTTGCC
AGGACGATGCCGAGAACATTGAATACAAAGTCTCCATCTCAGGAACCAGTGTAGAGTTGA
CGTGCCCTCTAGACAGTGACGAGAACTTAAAATGGGAAAAAAATGGCCAAGAGCTGCCTC
AGAAGCATGATAAGCACCTGGTGCTCCAGGATTTCTCGGAAGTCGAGGACAGTGGCTACT
ACGTCTGCTACACACCAGCCTCAAATAAAAACACGTACTTGTACCTGAAAGCTCGAGTGT
GTGAGTACTGTGTGGAGGTGGACCTGACAGCAGTAGCCATAATCATCATTGTTGACATCT
GTATCACTCTGGGCTTGCTGATGGTCATTTATTACTGGAGCAAGAATAGGAAGGCCAAGG
CCAAGCCTGTGACCCGAGGAACCGGTGCTGGTAGCAGGCCCAGAGGGCAAAACAAGGAG
CGGCCACCACCTGTTCCCAACCCAGACTATGAGCCCATCCGCAAAGGCCAGCGGGACCTG
TATTCTGGCCTGAATCAGAGAGCAGTCTGA

CD3 gamma chain mRNA cds: gi|160333908 (SEQ ID NO: 18)

ATGGAGCAGAGGAAGGGTCTGGCTGGCCTCTTCCTGGTGATCTCTCTTCTTCAAGGCACTG
TAGCCCAGACAAATAAAGCAAAGAATTTGGTACAAGTGGATGGCAGCCGAGGAGACGGT
TCTGTACTTCTGACTTGTGGCTTGACTGACAAGACTATCAAGTGGCTTAAAGACGGGAGCA
TAATAAGTCCTCTAAATGCAACTAAAAACACATGGAATCTGGGCAACAATGCCAAAGACC
CTCGAGGCACGTATCAGTGTCAAGGAGCAAAGGAGACATCAAACCCCCTGCAAGTGTATT
ACAGAATGTGTGAAAACTGCATTGAGCTAAACATAGGCACCATATCCGGCTTTATCTTCGC
TGAGGTCATCAGCATCTTCTTCCTTGCTCTTGGTGTATATCTCATTGCGGGACAGGATGGA
GTTCGCCAGTCAAGAGCTTCAGACAAGCAGACTCTGTTGCAAAATGAACAGCTGTACCAG
CCCCTCAAGGACCGGGAATATGACCAGTACAGCCATCTCCAAGGAAACCAACTGAGGAA
GAAGTGA

CD3 Zeta chain mRNA cds: gb|J04967.1 (SEQ ID NO: 19)

ATGAAGTGGAAAGTGTCTGTTCTCGCCTGCATCCTCCACGTGCGGTTCCCAGGAGCAGAG
GCACAGAGCTTTGGTCTGCTGGATCCCAAACTCTGCTACTTGCTAGATGGAATCCTCTTCA
TCTACGGAGTCATCATCACAGCCCTGTACCTGAGAGCAAAATTCAGCAGGAGTGCAGAGA
CTGCTGCCAACCTGCAGGACCCCAACCAGCTCTACAATGAGCTCAATCTAGGGCGAAGAG
AGGAATATGACGTCTTGGAGAAGAAGCGGGCTCGGGATCCAGAGATGGGAGGCAAACAG
CAGAGGAGGAGGAACCCCCAGGAAGGCGTATACAATGCACTGCAGAAAGACAAGATGGC
AGAAGCCTACAGTGAGATCGGCACAAAAGGCGAGAGGCGGAGAGGCAAGGGGCACGAT
GGCCTTTACCAGGGTCTCAGCACTGCCACCAAGGACACCTATGATGCCCTGCATATGCAG
ACCCTGGCCCCTCGCTAA

Figure 25

AFFINITY MATURATED T CELL RECEPTORS AND USE THEREOF

RELATED APPLICATIONS

This application is a continuation application of U.S. patent application Ser. No. 13/958,277 filed on Aug. 2, 2013, which is a Continuation of PCT Patent Application No. PCT/IL2012/000061 having International Filing Date of Feb. 5, 2012, which claims the benefit of priority under 35 USC § 119(e) of U.S. Provisional Patent Application No. 61/439,894, filed on Feb. 6, 2011.

The contents of the above applications are all incorporated by reference as if fully set forth herein in their entirety.

SEQUENCE LISTING STATEMENT

The ASCII file, entitled 74743SequenceListing.txt, created on Jul. 25, 2018, comprising 14,159 bytes, submitted concurrently with the filing of this application is incorporated herein by reference.

FIELD OF THE INVENTION

The present invention relates to methods and systems for increasing the affinity of a T cell receptor (TCR) to its ligand by subjecting the TCR gene to somatic hypermutation. The present invention further relates to use of affinity maturated TCRs to create reactive T cells, such as anti-tumor reactive T cells.

BACKGROUND OF THE INVENTION

Immune therapy has already been established as a central component of many cancer treatment regimens. Tumors express a wide variety of proteins that can be recognized by the immune system. In addition to mutated proteins and fusion proteins, the immune system can recognize developmentally and tissue-restricted proteins, as well as proteins highly overexpressed in cancer cells. Established therapies employ a variety of manipulations to activate antitumor immunity. These include passive immunization with monoclonal antibodies, introduction of adjuvants into the tumor microenvironment and systemic delivery of cytokines. Immune therapy can ameliorate the toxic effects of standard chemotherapy and is an essential element in the curative mechanism of bone marrow transplantation for hematologic malignancies. To date, experimental cancer immune therapies are based on established treatment regimens with the purpose of devising a more efficacious and less toxic protocol.

Adoptive T Cell Therapy

Adoptive T cell therapy relies on the in-vitro expansion of endogenous, cancer-reactive T cells. These T cells are harvested from cancer patients, manipulated and then reintroduced as a mechanism for generating productive tumor immunity. Adoptive T cell therapy has had some promising early clinical results and has been associated with clinical responses in a minority of patients with metastatic melanoma. $CD8^+$ cytotoxic T lymphocytes are the primary effector cells in adoptive T cell therapy. However, $CD4^+$ T cells may also play an important role in maintaining CD8+ cytotoxic function and transplantation of tumor reactive $CD4^+$ T cells has been associated with some efficacy in metastatic melanoma. T cells used in adoptive therapy can be harvested from a variety of sites, including peripheral blood, malignant effusions, resected lymph nodes and tumor biopsies. Although T cells harvested from the peripheral blood are technically easier to obtain, tumor-infiltrating lymphocytes (TILs) obtained from biopsies may contain a higher frequency of tumor-reactive cells. In practice, obtaining sufficient cells from tumor biopsies is difficult, although this approach has been used successfully in patients with melanoma.

Once harvested, T cells can be expanded either through polyclonal stimulation with activating antibodies or through exposure to specific tumor antigens, however this second approach requires the identification of relevant targets. Given the frequency of antigen loss variants in current clinical trials, the selection of appropriate targets may be challenging, potentially making polyclonal stimulation a more attractive approach.

In addition to antigen-loss variants, adoptive T cell therapies are limited by the replicative potential of cultured T cells. Several strategies, including the enforced expression of costimulatory proteins and telomerase, have been used to attempt to extend the life span of cultured T cells. IL-15 has also been considered as a possible additive to cultures in order to enhance the production of cytotoxic cells. Intriguingly, engraftment of adoptively transferred T cells appears to be enhanced in lymphodepleted hosts and strategies to combine pretreatment with lymphodepleting chemotherapy and adoptive T cell transplantation appear to increase treatment efficacy significantly.

Two alternative approaches attempt to circumvent low levels of endogenous antitumor reactivity in the peripheral blood by directly supplying T cells with the ability to recognize tumors. T cells harvested from the peripheral blood can be engineered to express T cell receptors (TCRs) that have been selected for tumor recognition. This approach has been previously tested in metastatic melanoma.

However, because TCR recognition of an antigen is MHC restricted, each engineered TCR can only be used in patients with the required MHC allele. MHC restriction can be bypassed by engineering T cells to express novel chimeric fusion proteins that link the antigen-binding domain of the B cell receptor with the signaling component of the TCR complex. These "T-bodies" can directly bind tumor antigens, leading to T cell activation, but can be used to target only cell surface overexpressed proteins while TCRs recognize peptides derived from proteins in all cell compartments.

TCR Affinity and T Cell Activity

Previous experiments in mouse models and clinical work have led to the widely accepted concept that for successful TCR gene therapy the generation of high-avidity T cells is a prerequisite. In a mouse tumor model it was demonstrated that complete eradication of solid tumors was possible only if the targeted tumor antigen was expressed at high levels so that it could be cross-presented by the surrounding stroma cells. In naturally occurring tumors, the amount of antigen detectable on tumor stroma is likely to be very low, suggesting that highly sensitive T cells are necessary to promote this bystander effect. Furthermore, high-affinity coreceptor-independent TCRs may allow the generation of both cytotoxic and helper T cells to synergize in the anti-tumor effect. The dependency of T cell activity on the affinity of the TCR to its ligand is one of the aspects currently under intensive research. Studies in this topic show, that when engineering higher affinity TCR mutants they retain their responsiveness to peptide-MHC complexes, however there is indeed a limitation to the level of affinity improvement which can be gained when responsiveness is kept. These studies, used artificial methods for the introduction of mutations, as well as predictions for the sites in which to induce mutations i.e.

CDR regions. In doing so these studies limit the overall number of mutations generated and also use a rather laborious method for their generation.

An alternative strategy to overcome T cell tolerance is based on the in-vitro affinity maturation of TCRs isolated from low avidity T cells. In this scenario, TCRs are subjected to in-vitro mutagenesis followed by selection of TCR sequences with improved binding affinity for the specific MHC/peptide combination. This affinity-maturation is achieved by using TCR display libraries expressed in mammalian cells, yeast or on the surface of a phage. This elegant strategy can be used to convert low avidity TCRs, isolated from a repertoire affected by tolerance, to high affinity receptors that are not present in the natural repertoire. The development of tetramer technology has made it easier to isolate T cells specific for particular antigens for example, CMV and it is now possible for direct infusion of these highly purified, specific CD8+ T cells from transplant donors to take place within just four hours of selection. Although T cell immunotherapy against viral targets has proven to be very successful, it is less straightforward when it comes to tumor-associated antigens (TAA)s. TAAs are inherently less immunogenic than viral antigens and cancer patients are usually immunocompromised either by the disease itself or by the treatment they are receiving. This emphasizes a need for high degrees of maturation of the TCR in its target recognition areas.

Somatic Hypermutation (SHM)

There are times when the requirements for biological function exceed the information content of the genome. B-lymphocytes of the adaptive immune system face just such a dilemma: how to extract a virtually infinite repertoire of antigen (Ag)-recognition from a finite supply of genomic information. A "one gene to one Ag" library is unfeasible, so instead, repertoire diversity is achieved through somatic alterations of the immunoglobulin (Ig) locus, which encodes the cell surface receptor responsible for antigen recognition. Ig molecules contain two light chains and two heavy chains arranged in a roughly Y-shaped configuration. The N-terminal prongs (Variable, or V region) specify the Ag-recognizing capacity, whereas the C-terminal stem (Constant, or C region) specifies the effector functions of the molecule. Somatic diversification events occur at both portions of the Ig. Primary diversification occurs in early B cell development during assembly of the V region, a process called V(D)J recombination. This involves the joining of three segments Variable (V), Diversity (D) and Joining (J) randomly selected from a germline pool of multiple gene segments. A mature B lymphocyte which has undergone V(D)J recombination is then distinct from all others at three levels: (i) the choice of V, D, and J segments, (ii) the combination of rearranged heavy and light chains and (iii) junctional insertions and deletions which occur during rearrangement. Somatic hypermutation (SHM) introduces point mutations into the V region antigen-binding pocket, creating Ig variants with enhanced affinity for a particular Ag. These mutations arise at a rate of $10^{-3}$/basepair/generation, several orders of magnitude above the rate of spontaneous mutation.

Activation Induced Cytidine Deaminase (AID)

For four decades after it was first proposed that genetic diversity of the precursors of antibody-forming cells arises from a high rate of spontaneous mutation, the identity of the mutator remained unknown. It wasn't until 1999 that Honjo and colleagues identified Activation-Induced Cytidine Deaminase (AID) as the key factor that triggers not only SHM but also CSR (Muramatsu et al., 2000; Muramatsu et al., 1999). Gene conversion was later shown to be dependent on AID, implicating AID as a fundamental mediator of the Ig diversification processes. Based on sequence homology, AID was classified into the APOBEC family of polynucleotide Cytidine deaminases, which perform hydrolytic deamination of Cytidine (C) to Uridine (U). Much like its APOBEC relatives, AID contains a canonical Cytidine Deaminase motif, with key Histidine and Cysteine residues used for zinc coordination and catalysis. The positively charged N terminus carries a putative bipartite nuclear localization signal, though its nuclear localization capacity has not been definitively shown. The C terminus, in contrast, harbors a Leucine rich nuclear export signal, which accounts for the predominantly cytoplasmic distribution of the AID protein. Noting the homology between AID and the well characterized RNA-deaminase APOBEC1, the original discoverers of AID proposed that it edited and activated the mRNA of a SHM- or CSR-catalyzing factor.

PCT Pub. No. WO 03/061363 provides methods for causing mutations in genes expressed in eukaryotic cells; the methods involve expressing AID in the cells. Also provided are cells expressing AID.

PCT Pub. No. WO 06/053021 provides methods using SHM for producing polypeptide and nucleic acid variants.

PCT Pub. No. WO 10/132092 provides fusion molecules comprising a cytidine deaminase polypeptide and a single stranded DNA binding protein. The '092 publication further provides methods of using the fusion molecules to induce mutations in target genes or polynucleotide sequences.

U.S. Pat. No. 7,569,357 provides T cell receptors (TCRs) that have higher affinity for a ligand than wild type TCRs. These high affinity TCRs are formed by mutagenizing a T cell receptor protein coding sequence to generate a variegated population of mutants of the T cell receptor protein coding sequence; transforming the T cell receptor mutant coding sequence into yeast cells; inducing expression of the T cell receptor mutant coding sequence on the surface of yeast cells; and selecting those cells expressing T cell receptor mutants that have higher affinity for the peptide/MHC ligand than the wild type T cell receptor protein.

U.S. Pat. No. 7,608,410 provides a method of increasing the affinity and/or decreasing the off-rate of a given TCR specific for a given target pMHC.

None of the background art, however, discloses or suggests increasing the affinity of a TCR to its ligand by subjecting the TCR gene to somatic hypermutation, particularly using the mutator enzyme AID. Further, none of the background art discloses or suggests that the affinity matured TCRs may be used to create anti-tumor reactive T cells.

There exists a long-felt need for more effective means for generating T cells that bear TCR with high functional avidity that have the capacity to recognize their MHC-peptide ligands on pathogenic agents, including but not limited to, tumor cells. There is a further need for methods for the rapid and effective generation of antigen specific T cells which can be used in adoptive cell transfer. Furthermore, there is a need for T cell based pharmaceutical compositions that can be used for treating a patient suffering from a disease, including but not limited to cancer.

SUMMARY OF THE INVENTION

The present invention provides methods for increasing the affinity of a T cell receptor (TCR) to its ligand. Particularly, the methods of the present increase the affinity of a TCR to its ligand by subjecting TCR genes to somatic hypermutation (SHM), directed by the mutator enzyme Activation Induced cytidine Deaminase (AID). The present invention further provides affinity maturated TCRs and T cells expressing same useful in treating cancer, e.g., by anti-tumor immunotherapy.

Effective T cell activation depends, among other factors, on the functional avidity of the peptide-MHC complex (pMHC) to the TCR, i.e., on the affinity and the number of pMHC-TCR contacts. Since the T cell repertoire is controlled by negative and positive selection in the thymus, naturally occurring TCRs have mostly low affinities, in the range of 1-100 μM. Moreover, unlike antibodies whose affinities improve over time by SHM, TCR do not undergo SHM. It is now disclosed for the first time that the affinity of a TCR to its ligand may be increased remarkably by subjecting TCR genes to SHM, directed by AID.

Thus, the present invention provides affinity maturation methods and systems for producing TCRs with high affinity to a selected antigen. The present invention further provides T cells bearing said affinity matured TCR and pharmaceutical compositions comprising same, for use in treating a disease including but not limited to cancer.

According to a first aspect, the present invention provides a method for increasing the affinity of a TCR to its ligand, the method comprising the steps of:
(i) expressing in a host cell a nucleic acid construct encoding a TCR gene or a fragment thereof,
(ii) mutating the TCR gene or fragment thereof using somatic hypermutation (SHM), and
(iii) selecting cells expressing a TCR with high (i.e., increased) affinity to the ligand.

According to one embodiment, the TCR gene encodes a TCRα chain and a TCRβ chain. In particular embodiments, the expression segments of TCRα and TCRβ are operably linked. In some embodiments, said TCR gene is a human TCR gene. In another embodiment, the fragment of a TCR gene comprises a variable domain of a TCRα chain or TCRβ chain. In yet another embodiment, said fragment of a TCR gene consists of the variable domain of a TCRα chain or TCRβ chain.

According to one embodiment, the SHM of step (ii) comprises expressing Activation Induced cytidine Deaminase (AID), or an analog thereof, in said host cell. According to another embodiment, expressing AID comprises expressing in said host cell a nucleic acid construct encoding AID. In particular embodiments, AID is human AID. In yet another particular embodiment, AID is encoded by the nucleic acid sequence as set forth in SEQ ID NO:3. In yet another embodiment, AID is encoded by an nucleic acid sequence analog of SEQ ID NO:3.

According to another embodiment, AID is expressed in a controlled manner. According to another embodiment, expressing AID comprises transiently expressing AID in said host cell.

According to another embodiment, the nucleic acid construct encoding AID comprises an inducible promoter. According to a particular embodiment, the inducible promoter is a Tet-on promoter. In one embodiment, the Tet-on promoter is induced by Tetracycline. In another embodiment, Tet-on promoter is induced by Doxycycline.

According to another embodiment, transiently expressing AID comprises expressing AID in said host cell using electroporation.

Typically, the host cell must express a CD3 anchor in order to express the TCR on its surface. The CD3 anchor is a complex of four different protein chains CD3δ, CD3γ, CD3ε and CD3ξ. Thus, according to this embodiment, the method further comprises expressing CD3 in the host cell. In a particular embodiment, the method comprises expressing in said host cell a nucleic acid construct encoding the four CD3 chains (i.e., CD3δ, CD3γ, CD3ε and CD3ξ).

According to yet another particular embodiment, the nucleic acid construct encoding a TCR gene of the invention further comprises said four CD3 chains. According to another embodiment, the TCR and CD3 are operably linked.

Typically, the host cell of the invention takes advantage of the natural repair, transcription and replication mechanism in said cells that is essential for somatic hypermutation (SHM). According to one embodiment, the host cell does not express endogenous TCRs. In a particular embodiment, the host cell is a cell other than a T cell. Non limiting examples of host cells that may be used in the methods of the present invention include 293HEK (which stably expresses Tet repressor protein), HeLa, U2OS and NIH-3T3. According to a particular embodiment the host cell is 293HEK.

According to another embodiment, the step of mutating TCR using AID and selecting cells expressing affinity maturated TCRs (i.e., steps (ii) and (iii)) are repeated, in order to optimize TCR affinity. In one embodiment, said steps are repeated at least twice. In another embodiment, said steps are repeated at least three times.

According to another embodiment, the ligand (e.g., the antigen which binds to the TCR) is a peptide-MHC complex.

According to another embodiment, the peptide is a tumor antigen. According to another embodiment, the antigen is a tumor associated antigen (TAA). According to another embodiment, the TAA is selected from antigens associated with hematological malignancies and solid tumors. According to another embodiment, the solid tumors are selected from the group consisting of colon carcinoma, breast carcinoma, prostate carcinoma, renal cell carcinoma (RCC), lung carcinoma, sarcoma and melanoma. According to a particular embodiment, the solid tumor is melanoma.

According to another embodiment, the peptide comprises the amino acid sequence KVPRNQDWL (SEQ ID NO:5) or a derivative thereof. According to another embodiment, the peptide consists of the amino acid sequence KVPRNQDWL (SEQ ID NO:5).

According to some embodiments, the peptide is an antigen associated with a pathogen selected from the group consisting of viruses, bacteria, protozoa, parasites. In another embodiment, the antigen is associated with a particular autoantibody.

Selecting cells expressing a TCR with high affinity to a ligand (e.g. affinity maturated TCRs) in step (iii) of the method of the invention comprises, in another embodiment, using tetramer staining. In another embodiment, said step further comprises sorting and/or selecting said cell using Fluorescence-Activated Cell Sorting (FACS). The tetramer staining assay is known in the art as assay useful in testing TCR-MHC binding capability (previously described, for instance in Ogg and McMichael, 1998).

According to another embodiment the TCR affinity maturation methods of the present invention are preformed in vitro. According to said method, the TCR genes are cloned into an expression vector, such as a retroviral expression vector. Thereafter, the TCR genes are mutated by AID and nuclear extract from a hypermutating cell line, (e.g., a Ramos cell line) to produce a library of differently mutated vectors. In some embodiments, said library is amplified by transformation into bacteria, and plasmids comprising mutated TCR are extracted. Thereafter, the library is transfected into CD3 expressing cells (e.g., 293HEK cells using retroviruses). Thereafter, the cells are analyzed for affinity matured TCR by tetramer staining and are sorted and selected by FACS (as described above).

According to another aspect the present invention provides an isolated nucleic acid sequence encoding a TCR with an increased affinity to a ligand (i.e., an affinity matured TCR), obtained by the methods of the present invention. According to another aspect the present invention provides an expression vector comprising the nucleic acid sequence encoding a TCR of the present invention. According to another embodiment, there is provided a method for preparing a T cell comprising an affinity matured TCR, the method comprising expressing the expression vector (encoding an affinity matured TCR) in a T cell. In one embodiment, the T cell is an autologous T cell. In another embodiment, the T cell is originated (e.g. derived) from an HLA identical allogeneic donor.

According to another aspect the present invention provides a TCR having increased affinity for a selected ligand, wherein the TCR comprises mutations induced by Activation Induced cytidine Deaminase (AID) or analog thereof. In a specific embodiment, AID has the nucleic acid sequence as set forth in SEQ ID NO:3. In some embodiments, said TCR is produced according to the methods of the present invention. In one embodiment, the TCR (having increased affinity) exhibits a dissociation constant lower than 50 nanomolar for a selected ligand. The TCR of the invention is, in some embodiments, non-naturally occurring TCR.

According to another aspect, the present invention provides an isolated T cell comprising (e.g., expressing on its surface) TCRs having increased affinity for a selected ligand, wherein the TCR comprises mutations induced by AID or analog thereof. In a specific embodiment, AID has the nucleic acid sequence as set forth in SEQ ID NO:3. In some embodiments, said TCR is produced according to the methods of the present invention.

In some embodiments of the invention, the T cell is selected from a naïve lymphocyte, a cytotoxic T lymphocyte (CTL) and a regulatory T cell. In another embodiment, the T cell is a CTL. In another embodiment, the T cell is a CD8+ T cell. In another embodiment, the T cell is a CD4+ T cell. In another embodiment, the TCR (having increased affinity) exhibits a dissociation constant lower than 50 nanomolar for a selected ligand. In one embodiment, the T cell is an autologous T cell. In another embodiment, the T cell is derived from a HLA-identical allogeneic donor.

In particular embodiments, the T cells of the invention may be used in adoptive cell therapy for treatment of a disease including but not limited to cancer or an infectious disease. According to some embodiments, the adoptive cell therapy comprises the steps of: (i) obtaining T cells, wherein said T cells are selected from autologous T cells or T cells derived from a HLA-identical allogeneic donor; (ii) cloning the T cell of step (i) to express affinity matured TCRs (according to the method of the invention); (iii) introducing the T cells expressing the high affinity TCR to a subject in need of said therapy.

According to another aspect the present invention provides a pharmaceutical composition comprising a T cell expressing on its surface an affinity matured TCR, and a pharmaceutically acceptable carrier.

According to some embodiments, the present invention provides pharmaceutical composition comprising a T cell expressing an affinity matured TCR for use in adoptive T cell therapy.

According to another aspect the present invention provides a method for treating cancer in a subject comprising administering to said subject a pharmaceutically effective amount of the pharmaceutical composition comprising a T cell comprising an affinity matured TCR, and a pharmaceutically acceptable carrier.

According to one embodiment, the cancer is selected from the group consisting of prostate cancer, breast cancer, skin cancer, colon cancer, lung cancer, pancreatic cancer, head and neck cancer, kidney cancer, ovarian cancer, cervical cancer, bone cancer, liver cancer, thyroid cancer, brain cancer, lymphoma, myeloma and leukemia.

According to another embodiment, the cancer is a solid tumor. According to particular embodiments, the solid tumor is selected from the group consisting of: prostate cancer, breast cancer, skin cancer, colon cancer, lung cancer, pancreatic cancer, head and neck cancer, kidney cancer, ovarian cancer, cervical cancer, bone cancer, liver cancer, thyroid cancer and brain cancer. According to a particular embodiment, the cancer is melanoma.

According to certain embodiments, the cancer is a hematopoietic malignancy. According to particular embodiments, the hematopoietic malignancy is selected from the group consisting of: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to another aspect the present invention provides a pharmaceutical composition comprising a T cell comprising an affinity matured TCR (obtained according to the present invention), and a pharmaceutically acceptable carrier, for treating cancer in a subject in need thereof.

According to additional embodiments, the T cells expressing affinity matured TCRs and pharmaceutical composition comprising same, may be used for treating any other disease or disorder wherein the use of reactive T cells may be advantageous. For instance, the compositions of the present invention can be used for the treatment of bacterial, viral or parasitic infections, particularly chronic infections, by engineering and selecting TCRs that bind with a high affinity antigens associated with a bacteria, virus or parasite (e.g., from Epstein Barr virus, herpes virus, human immunodeficiency virus).

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE SEVERAL VIEWS OF THE DRAWING(S)

Figure 4:
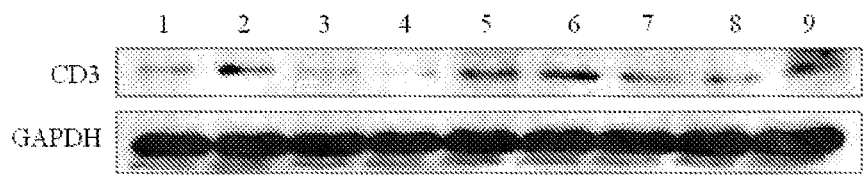

FIG. 4 is a Western blot analysis of six different 293TREx cell lines that were infected with CD3 packaging viruses and selected for Puromycin resistance. 293TREx cell line was used as a negative control (line 1) and mouse splenocytes were used as a positive control (line 9). Lines 2, 3, 4, 5, 6, 7, 8 show 293TREx cell lines with CD3 line 2, 4, 6, 7, 8 and 9, respectively.

Figure 5:
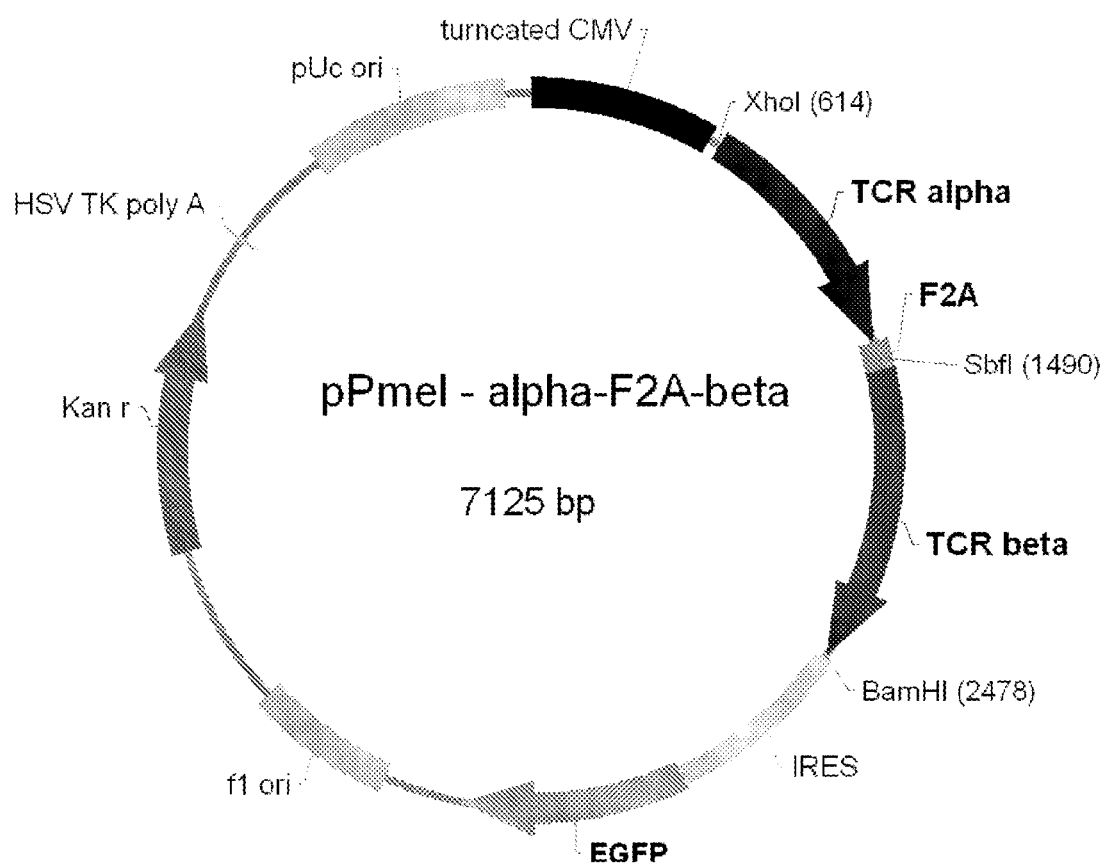

FIG. 5 depicts the plasmid for polycistronic mammalian expression of TCRα and TCRβ genes. TCRα and TCRβ expression are controlled by a CMV promoter Both TCRα and TCRβ chains are expressed together as polycistronic chains with a F2A sequence between them. EGFP serves as an indicator for successful transduction. EGFP expression is controlled by an IRES sequence.

Figure 6A:
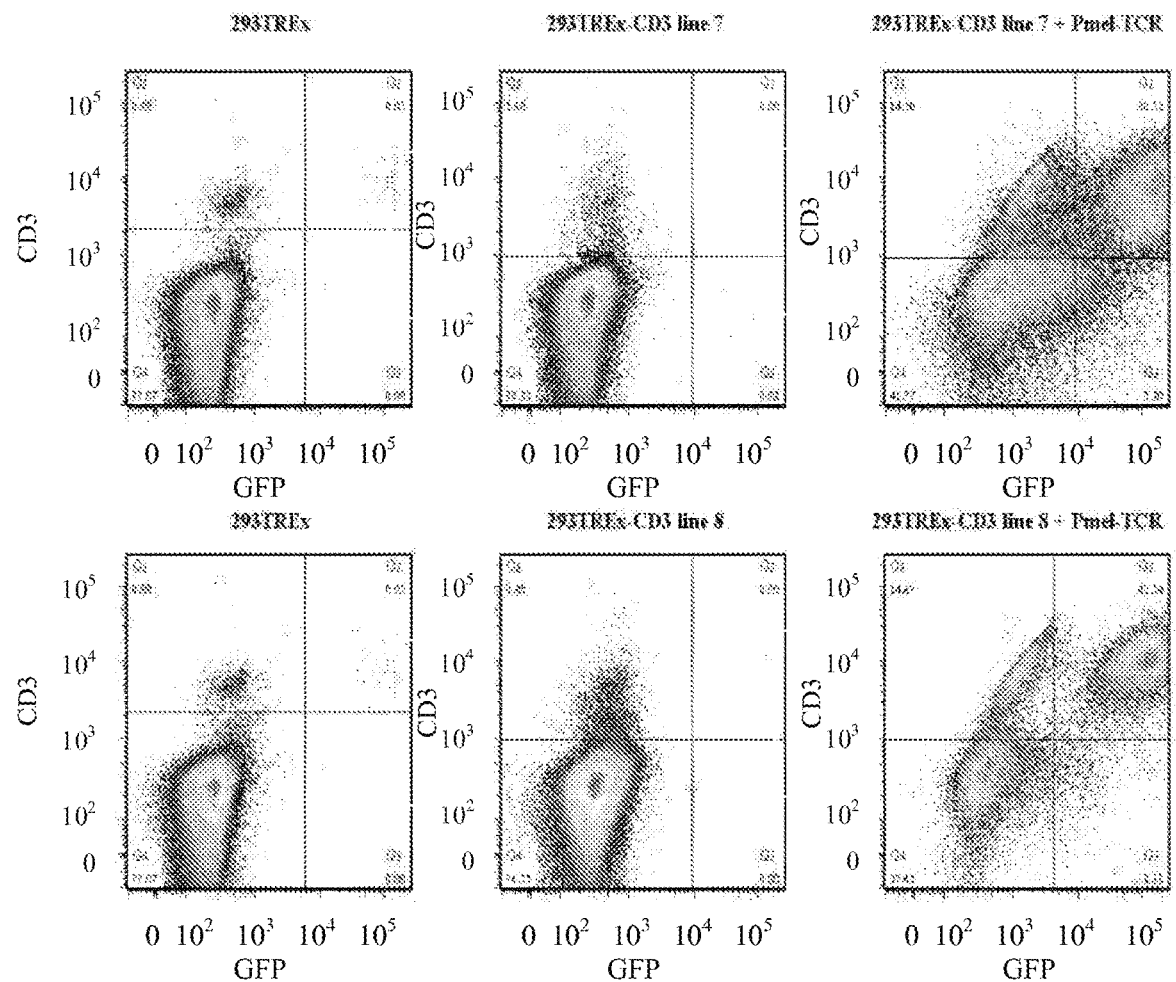

FIG. 6A is a FACS result of 293TREx and two 293TREx-CD3 cell lines (7 and 8) that were, or were not stably transfected with Pmel-TCR expression vector and stained with APC-CD3s antibody. FIG. 6B is a graphic representation of FIG. 6A. The top panel depicts the results of the 293TREx-CD3 cell line 7, and the bottom panel depicts the results of the 293TREx-CD3 cell line 8, (intensity units are shown in the x axis: 0, $10^2$, $10^3$, $10^4$ and $10^5$; percent of max is shown in the y axis as: 20, 40, 60, 80 and 100).

FIG. 7 depicts 293TREx-CD3 cell stably expressing Pmel-TCR, stained with APC-CD3s antibody and observed in confocal microscopy. The double positive expression of CD3 and TCR can be seen by the GFP inside the cell (indicating TCR vector expression) and the APC-CD3s staining of the cell surface (red dots).

Figure 8A:
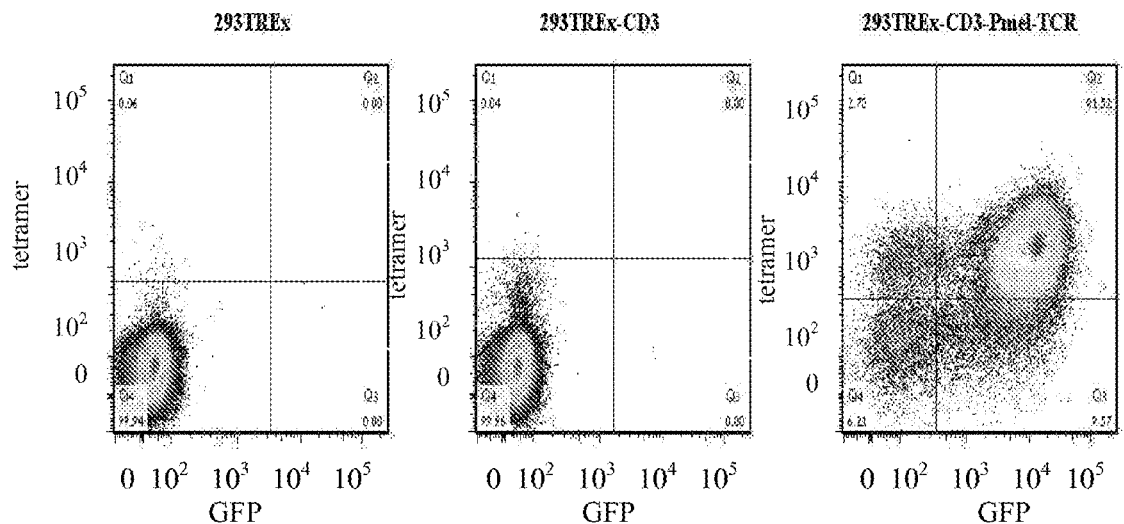
Figure 8B:
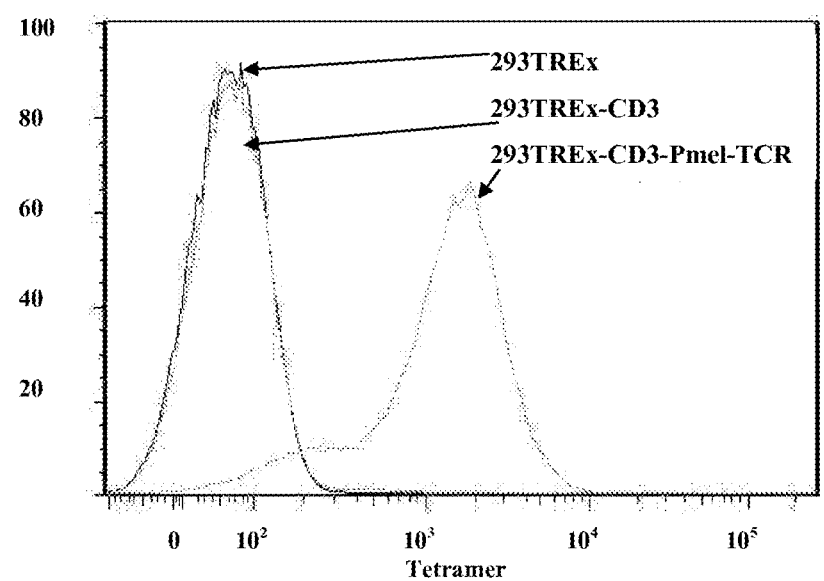

FIG. 8A is a FACS analysis of 293TREx, 293TREx-CD3 and 293TREx-CD3-Pmel-TCR cell lines that were stained with APC-Tetramer. FIG. 8B is graphic representation of FIG. 8A (intensity units are shown in the x axis: 0, $10^2$, $10^3$, $10^4$ and $10^5$; percent of max is shown in the y axis as: 20, 40, 60, 80 and 100).

Figure 9:
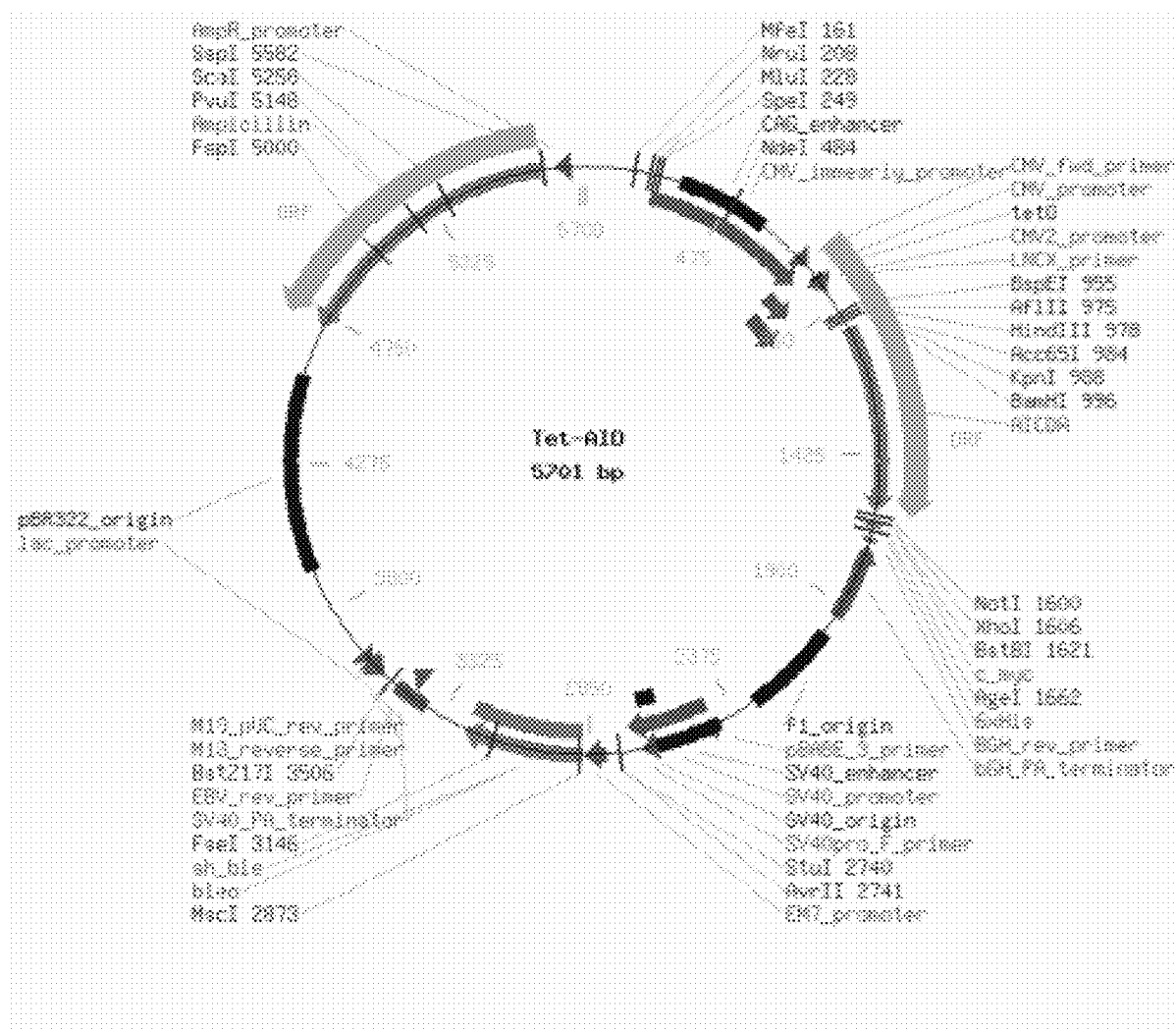

FIG. 9 depicts the Tet-AID expression vector map.

Figure 10:
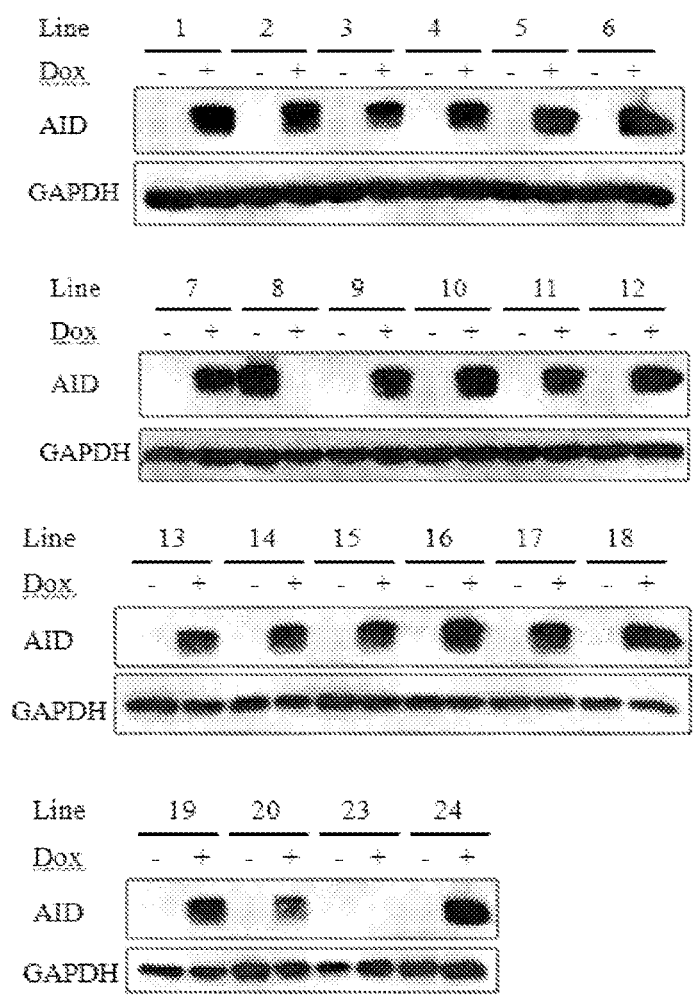

FIG. 10 is a Western blot analysis for AID and GPADH (as control) detection in the presence of Doxycycline. 293TREx-CD3-Pmel-TCR-Tet-AID cell lines were or were not treated with 1 μg/ml Doxycycline (Dox) for 24H before protein extraction.

FIG. 11 is a FACS analysis of tetramer stained 4P cell lines. The depicted cell lines (from the top left corner) are 293TREx, 4P.1, 4P.2, 4P.3, 4P.4, 4P.5-4P.7 (second line, left to right), 4P.9-4P.12 (third line, left to right), 4P.13-4P.16 (fourth line, left to right), 4P.17-4P.20 (fifth line, left to right), 4P.24 (sixth line). X axis shows the intensity of GFP-TCR vector, y axis shows the intensity of tetramer staining.

FIG. 12 is a FACS analysis of Tetramer stained 293TREx-CD3-Pmel-TCR-TR-Tet-AID (named 4P) cell lines 72 H after treatment with or without AID induction by Doxycycline. The depicted cell lines (from the top left corner) are 4P.2, 4P.2 (Dox), 4P.11 (Dox), 4P.11; second line: 4P.4, 4P.4 (Dox), 4P.14 (Dox), 4P.14; third line: 4P.6, 4P.6 (Dox), 4P.16 (Dox), 4P.16; fourth line: 4P.9, 4P.9 (Dox), 4P.17, 4P.17 (Dox); fifth line: 4P.10, 4P.10 (Dox), 4P.18, 4P.18 (Dox).

Figure 13:
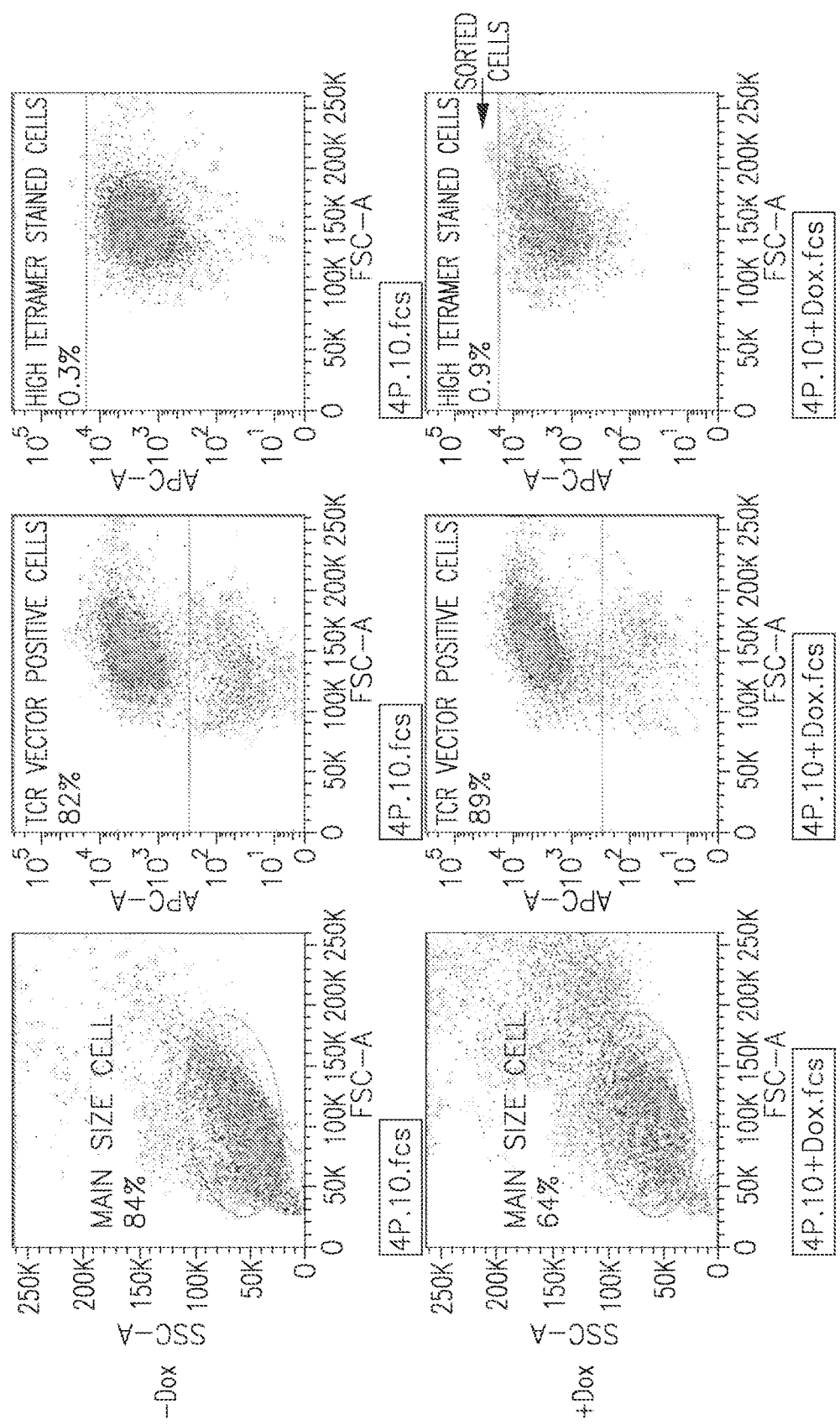

FIG. 13 shows gating procedure and sorting parameters for FACS sorting of 4P.10 and 4P.17 cell lines, 72H after AID induction (+Dox) or without AID induction as control (−Dox).

Figure 14:
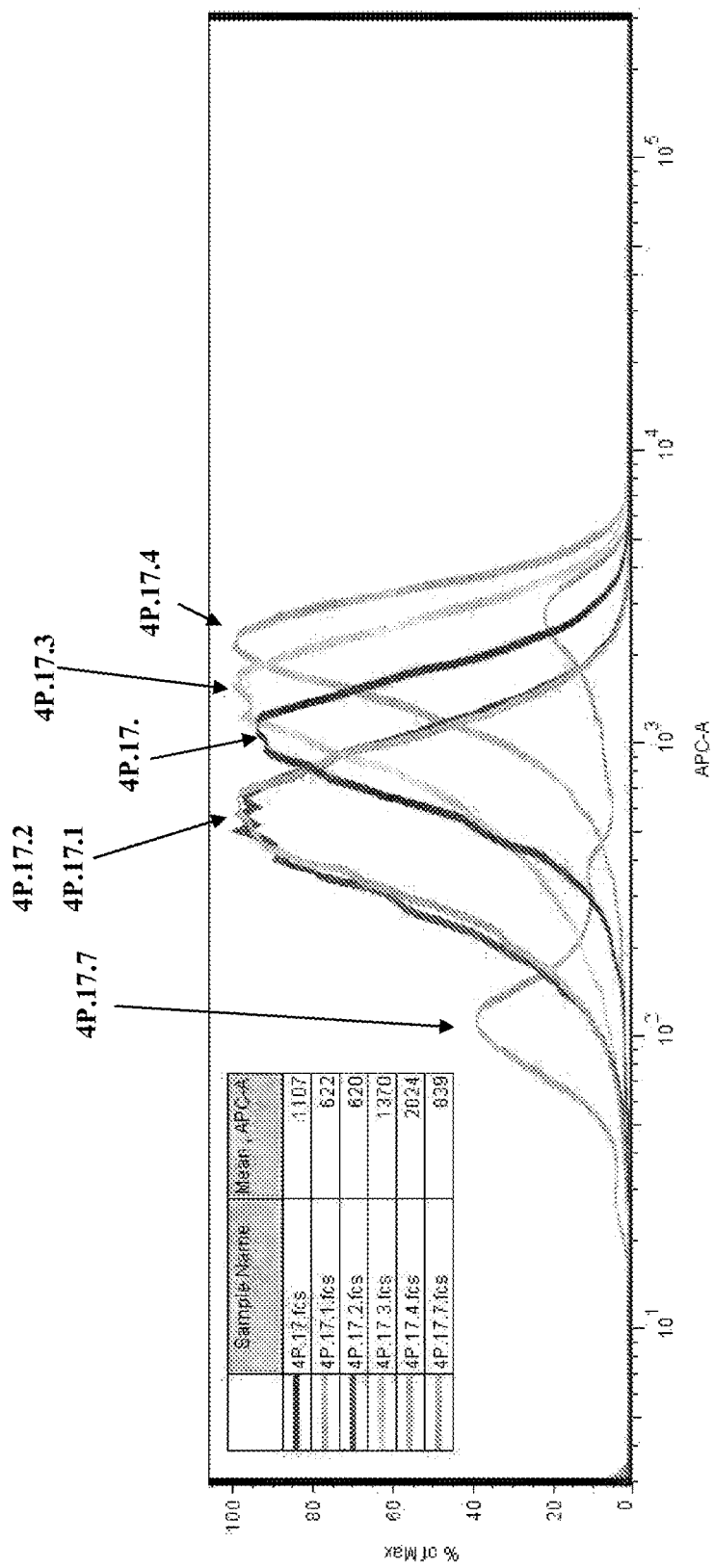

FIG. 14 shows FACS analysis of Tetramer stained 4P.17 sorted colonies.

Figure 15A:
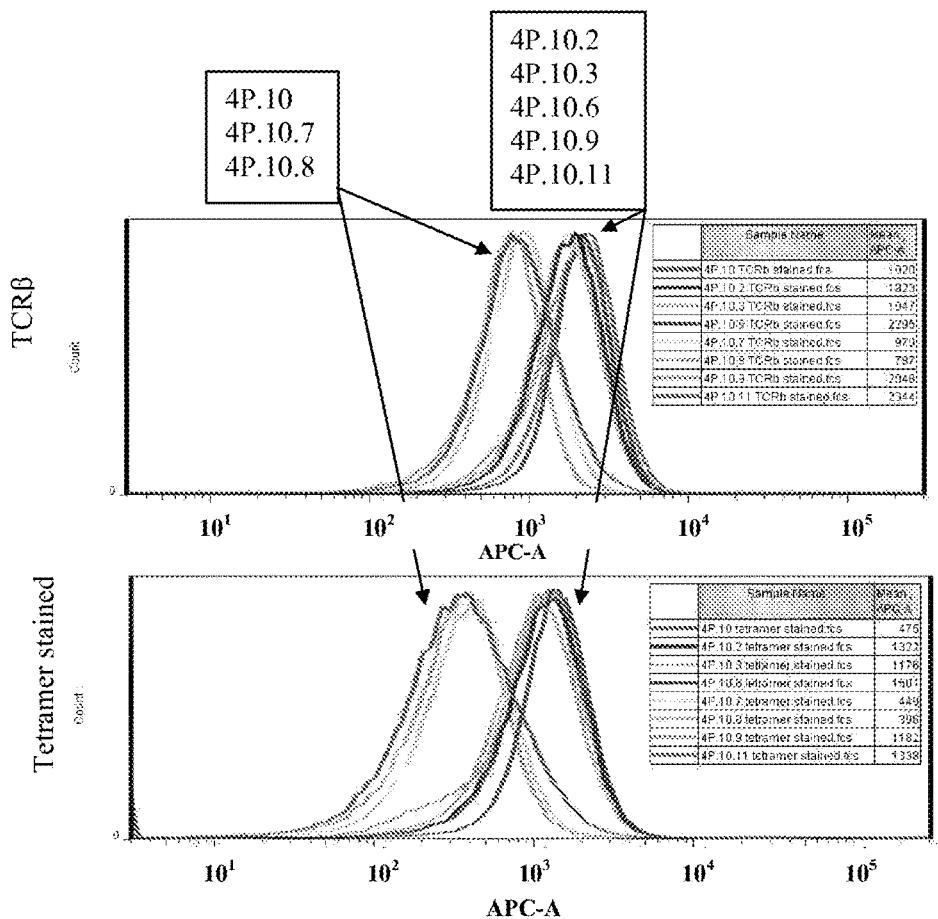
Figure 15B:
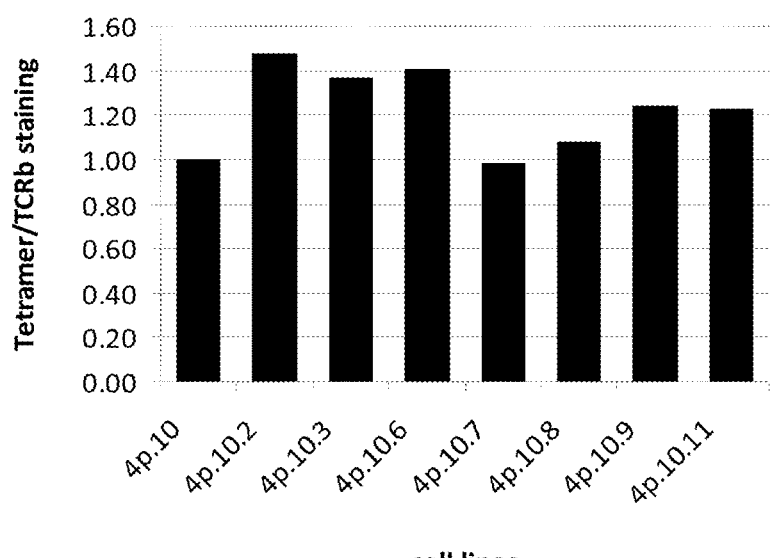
Figure 15C:
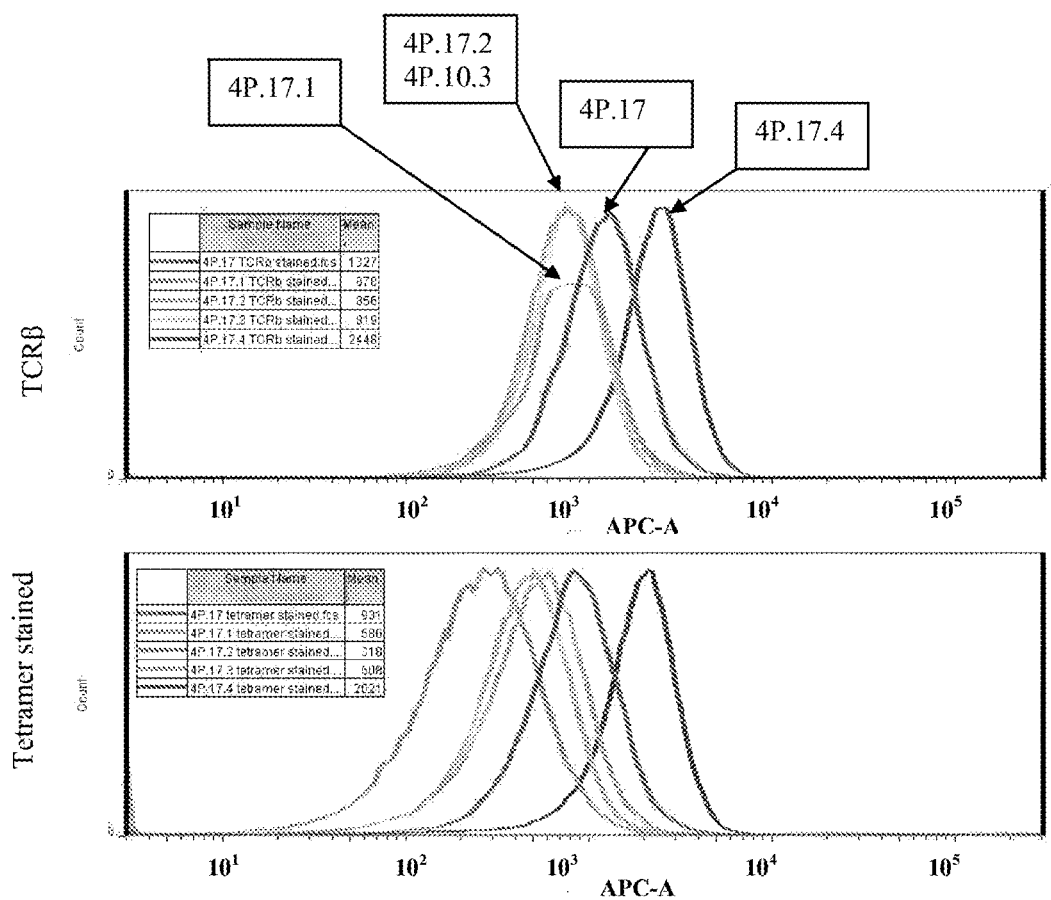
Figure 15D:
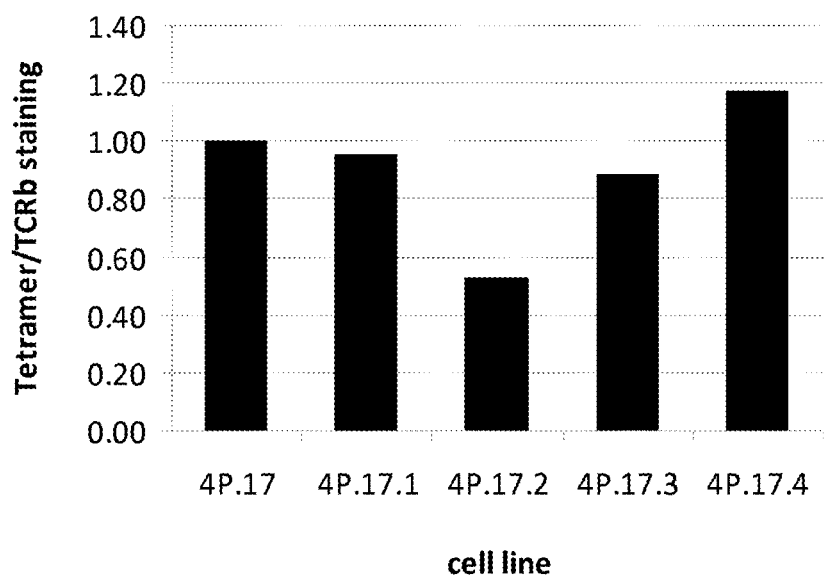

FIGS. 15A-15D show FACS analysis of tetramer or TCRβ stained cell lines 4P.10.x and 4P.17.x (FIGS. 15A and 15C, respectively) and a graph depicting statistical analysis of the division of tetramer (FIGS. 15B and 15D). The peak order depicted in FIG. 15C is from left to right: 4P.17.2, 4P.17.3, 4P.17.1, 4P.17 and 4P.17.4.

Figure 16:
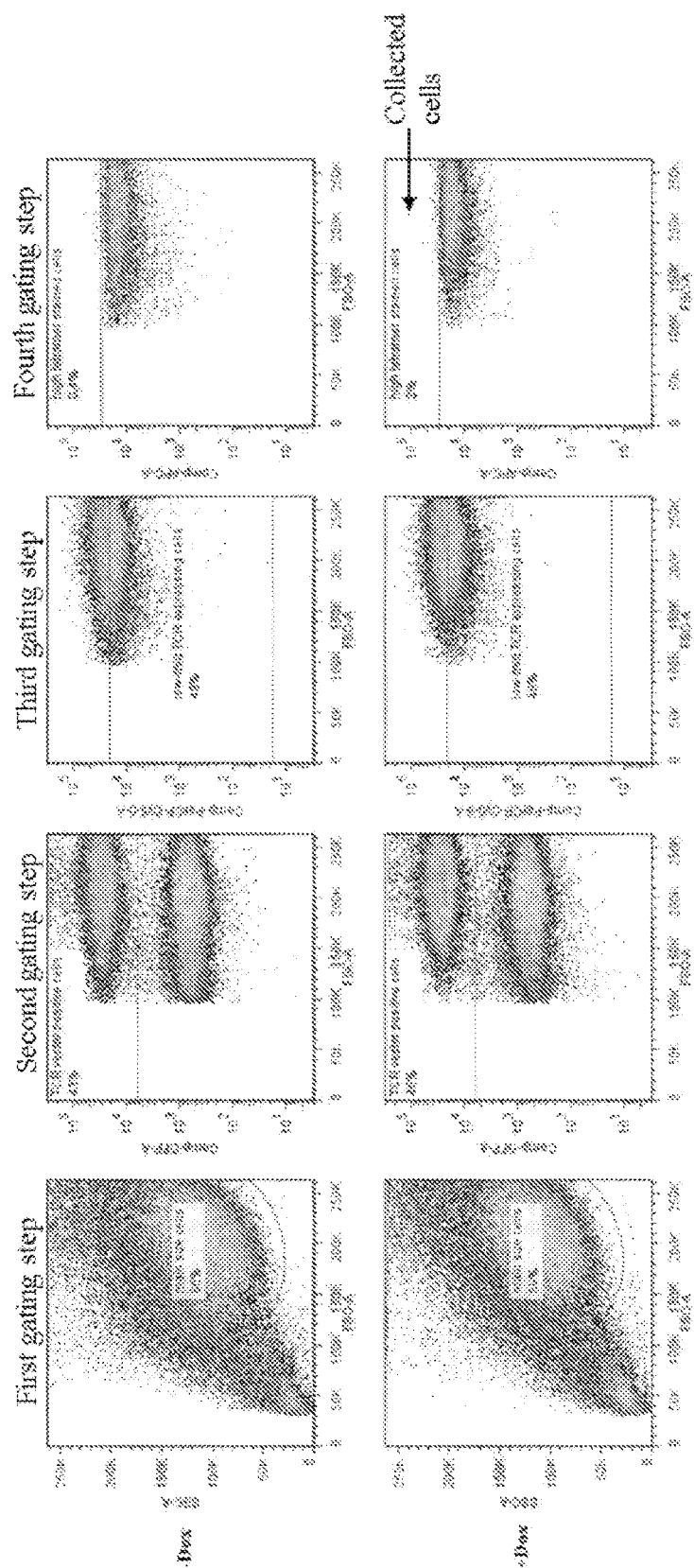

FIG. 16 depicts the gating steps for first cycle of sorting high affinity 4P.17 cells 72H after induction of AID.

Figure 17A:
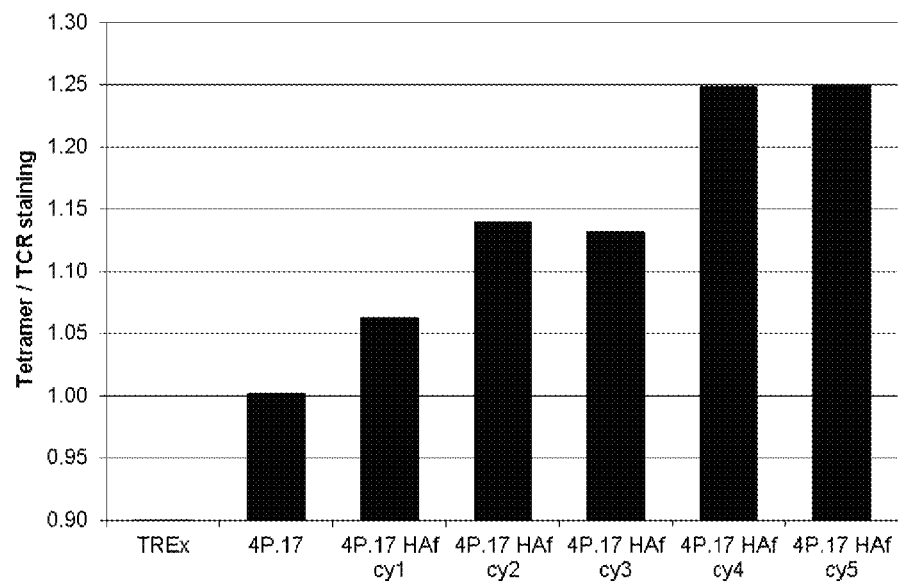
Figure 17B:
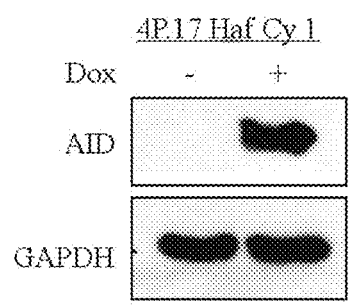

FIG. 17A shows FACS analysis of Tetramer/TCR staining of cells from 5 different enrichment cycles of sorted high affinity 4P.17 cells. FIG. 17B shows Western blot analysis of protein extracts (AID and GAPDH) from a representative cycle of induction of AID by Dox (+) or without Dox (−)

Figure 18:
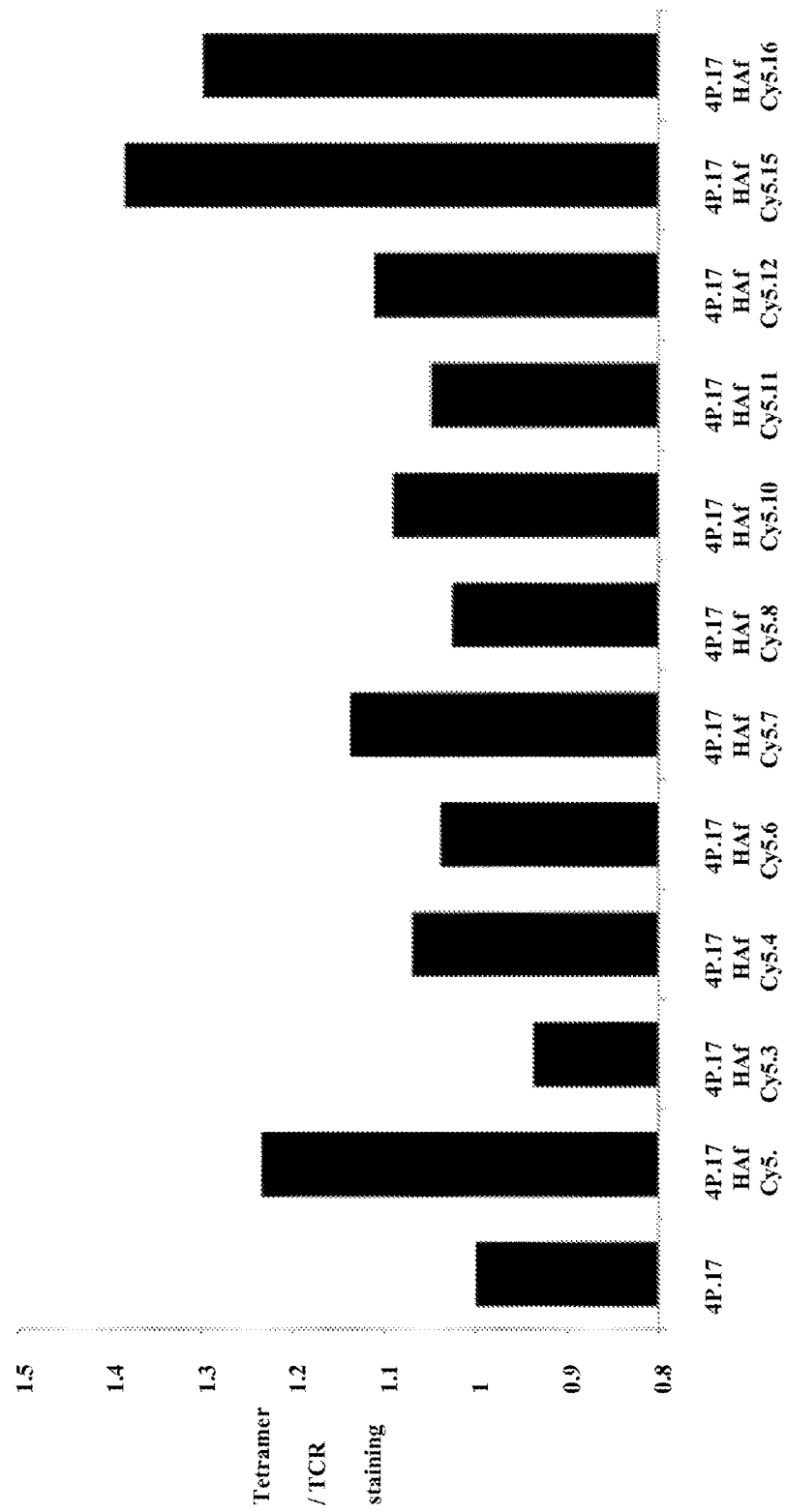

FIG. 18 shows FACS analysis of Tetramer/TCR staining of cells from several different colonies that were obtained by limiting dilutions of 4P.17 HAf Cy 5 cell line.

Figure 19:
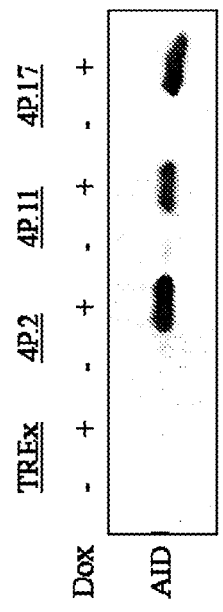

FIG. 19 shows western blot analysis of protein extracts from 4P cell lines cultured with (+) or without (−) Dox.

Figure 20:
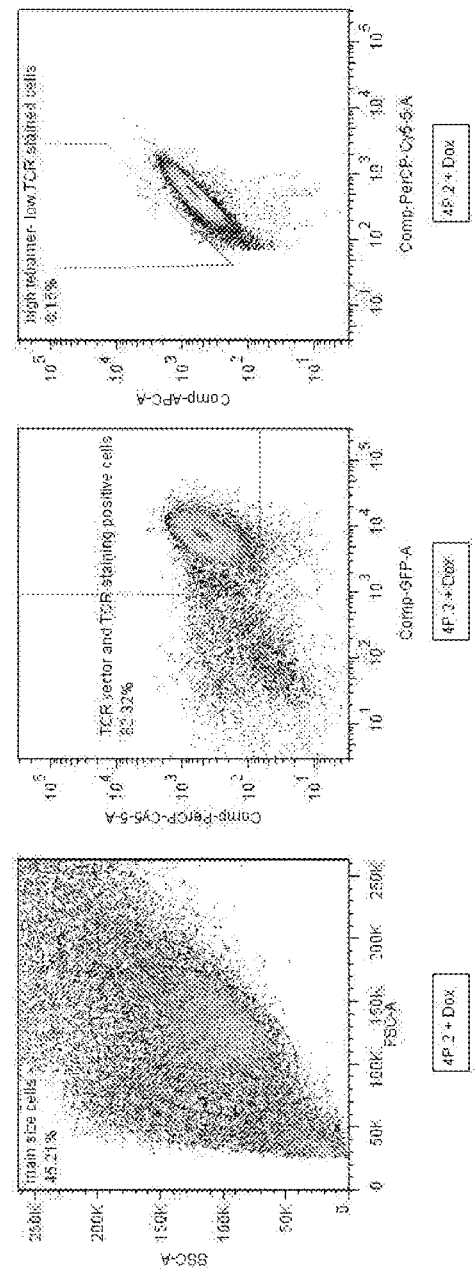
Figure 21A:
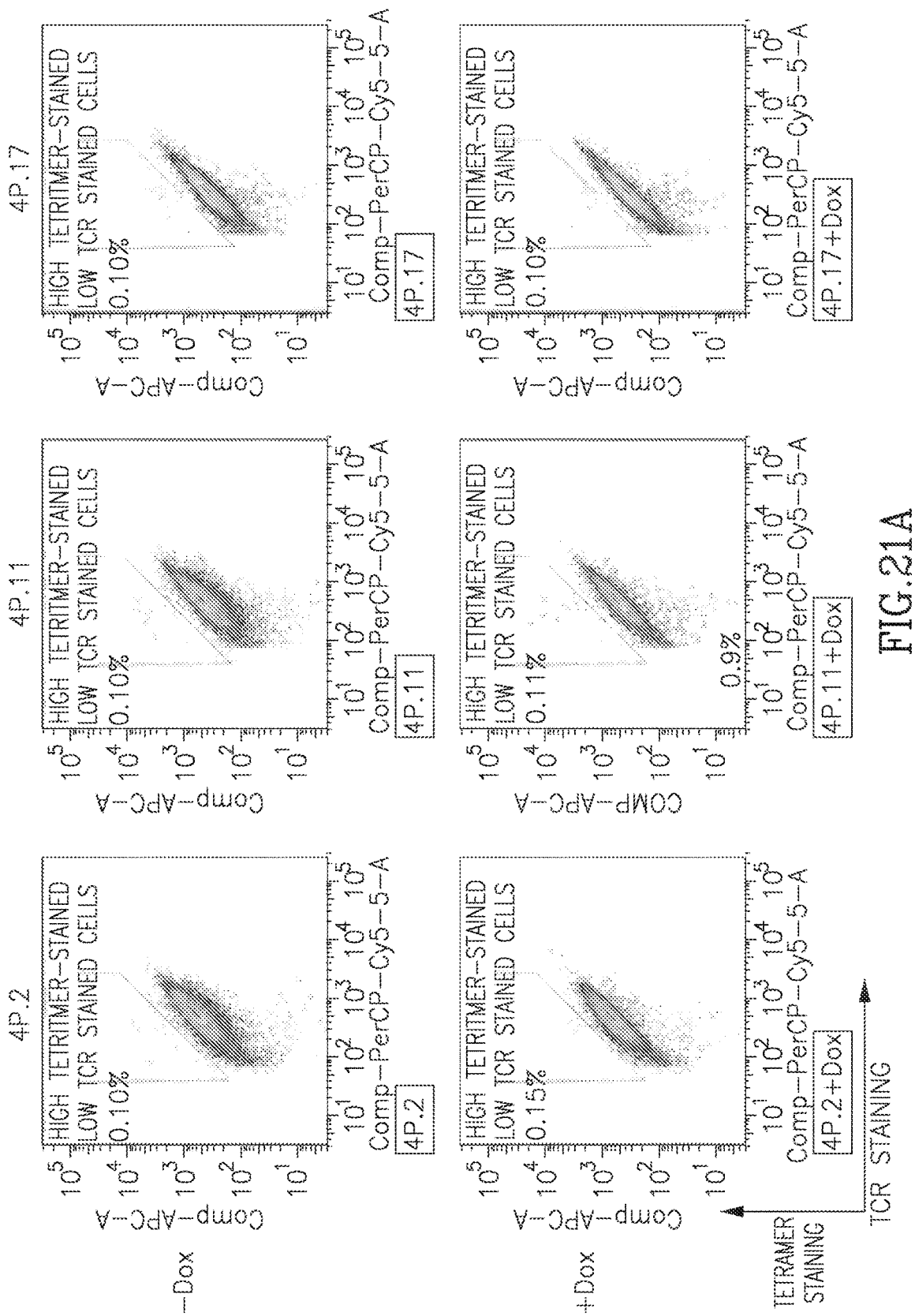
Figure 21B:
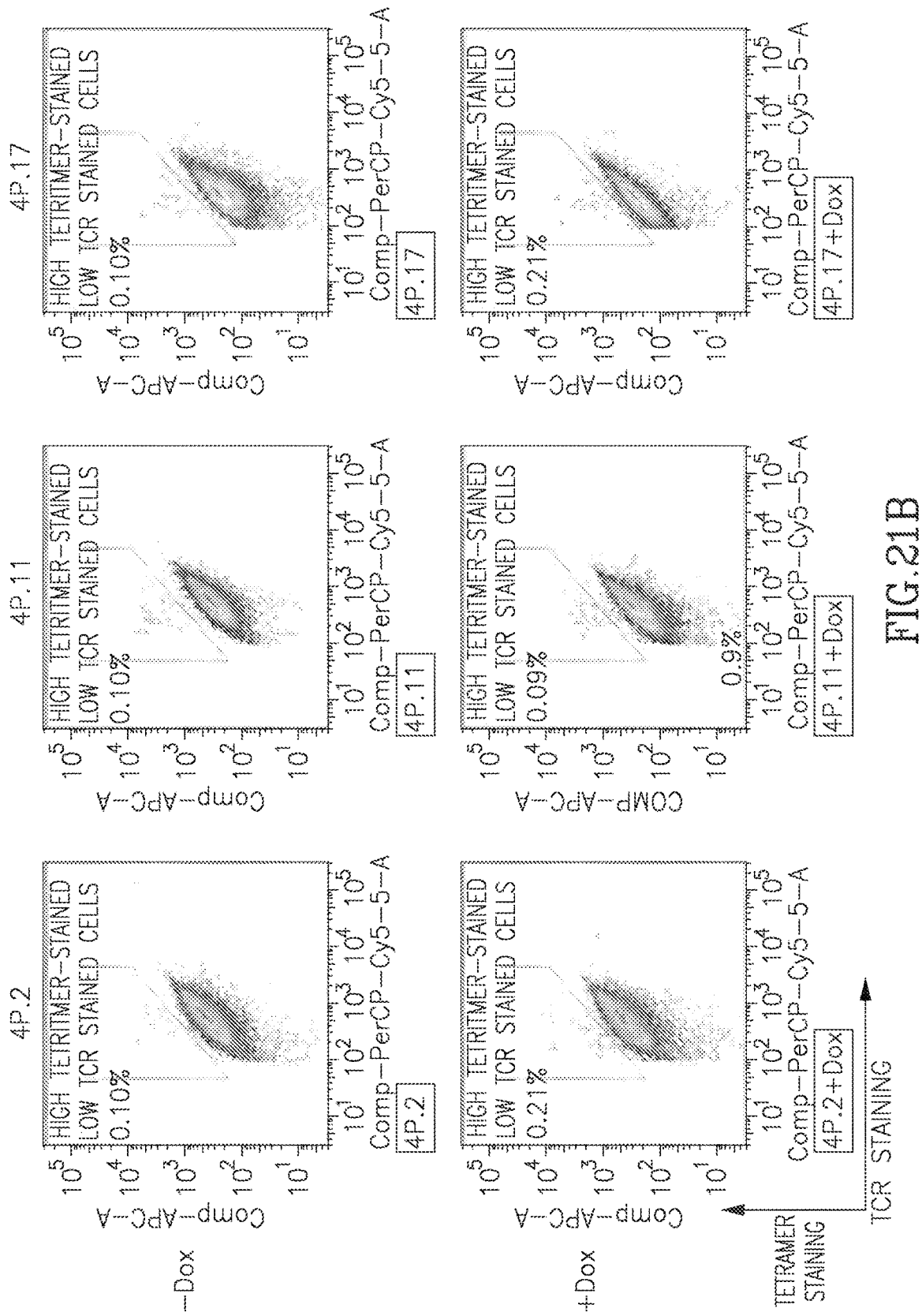
Figure 21C:
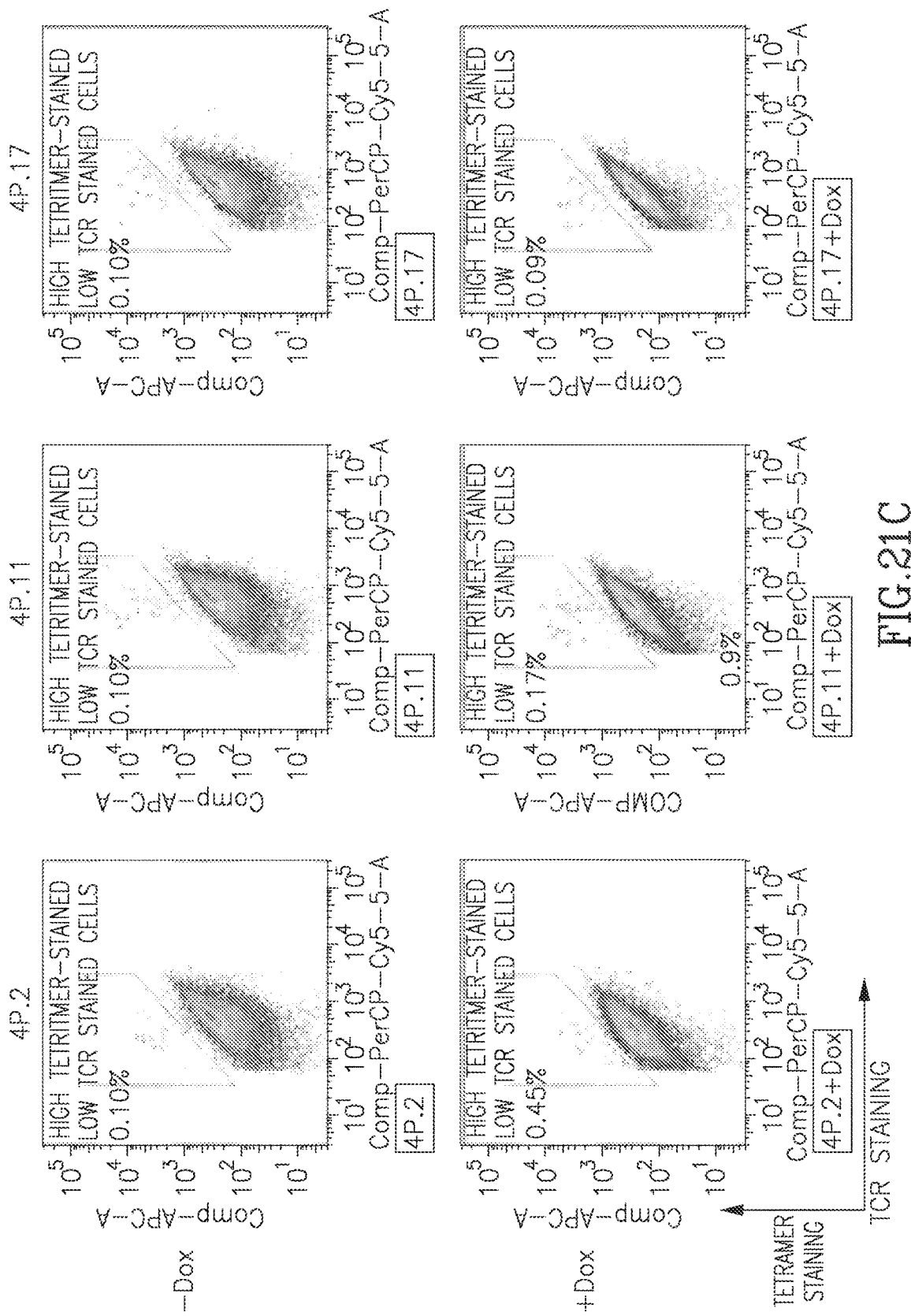
Figure 21D:
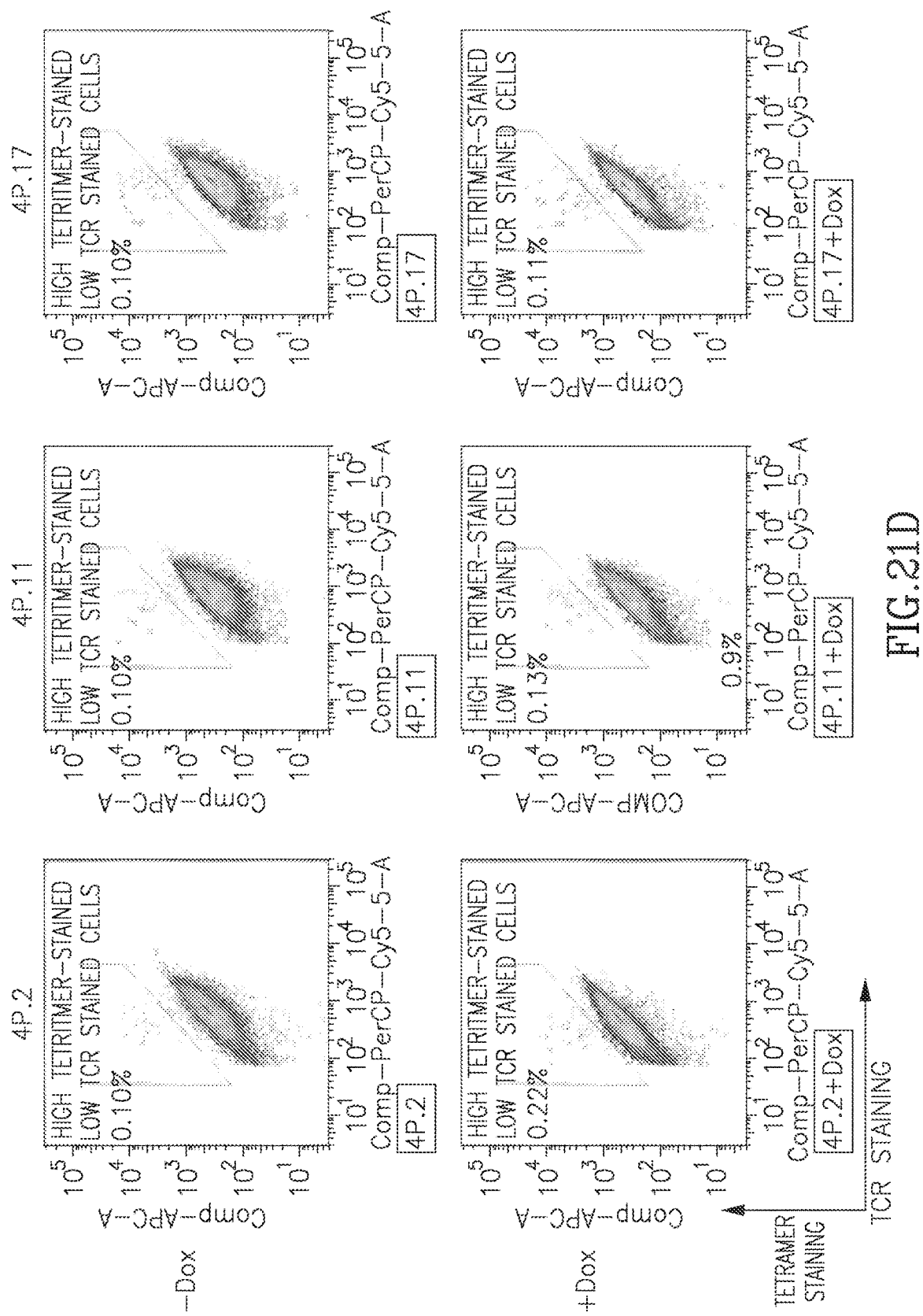
Figure 21E:
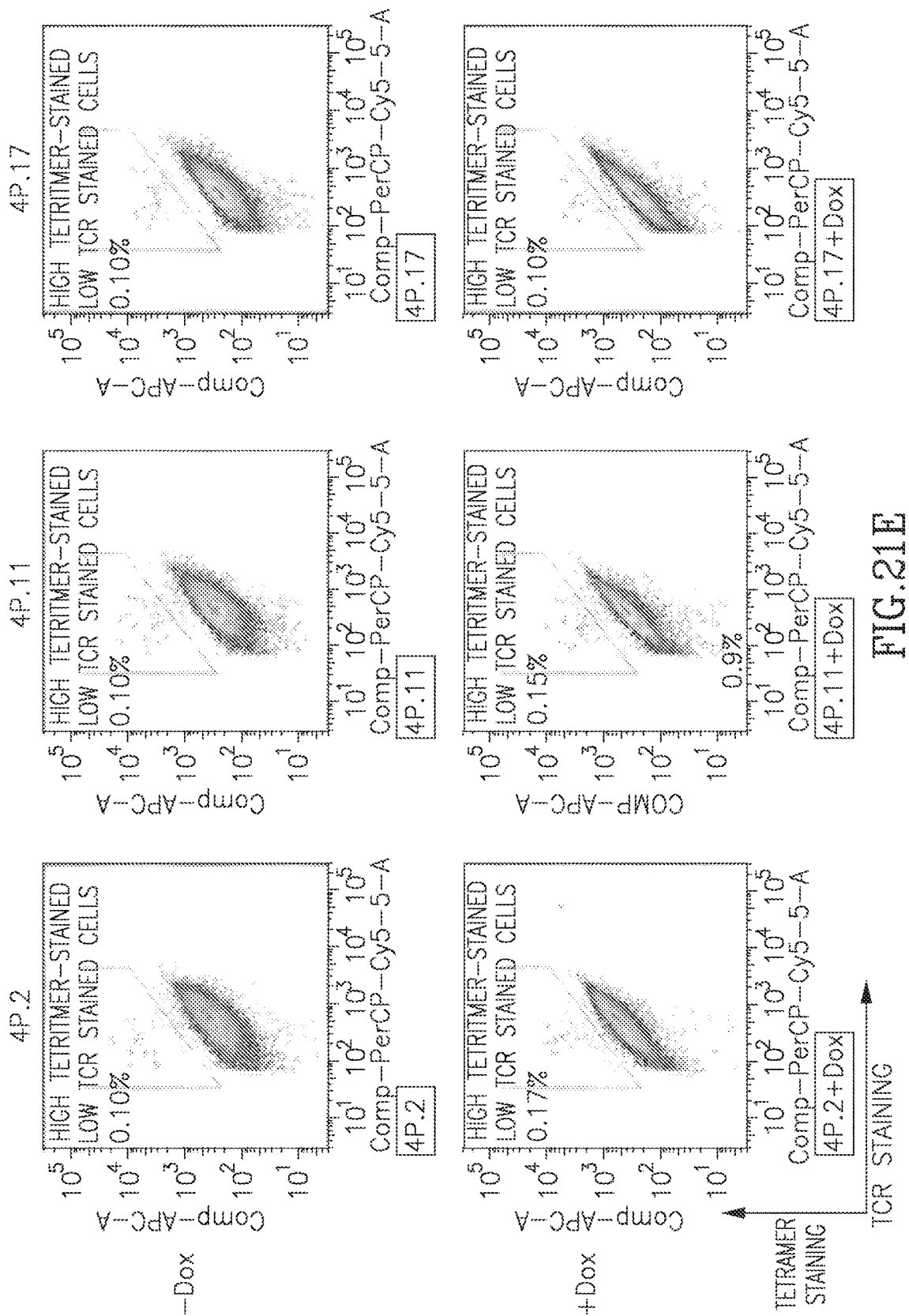

FIG. 20 depicts gating steps for sorting of high affinity cells after long AID induction.

FIGS. 21A-21E show differences in cell affinity between AID induced or un-induced 4P cell lines after 2 (FIG. 21A), 3 (FIG. 21B), 5 (FIG. 21C), 6 (FIG. 21D) or 7 (FIG. 21E) weeks of induction.

Figure 22A:
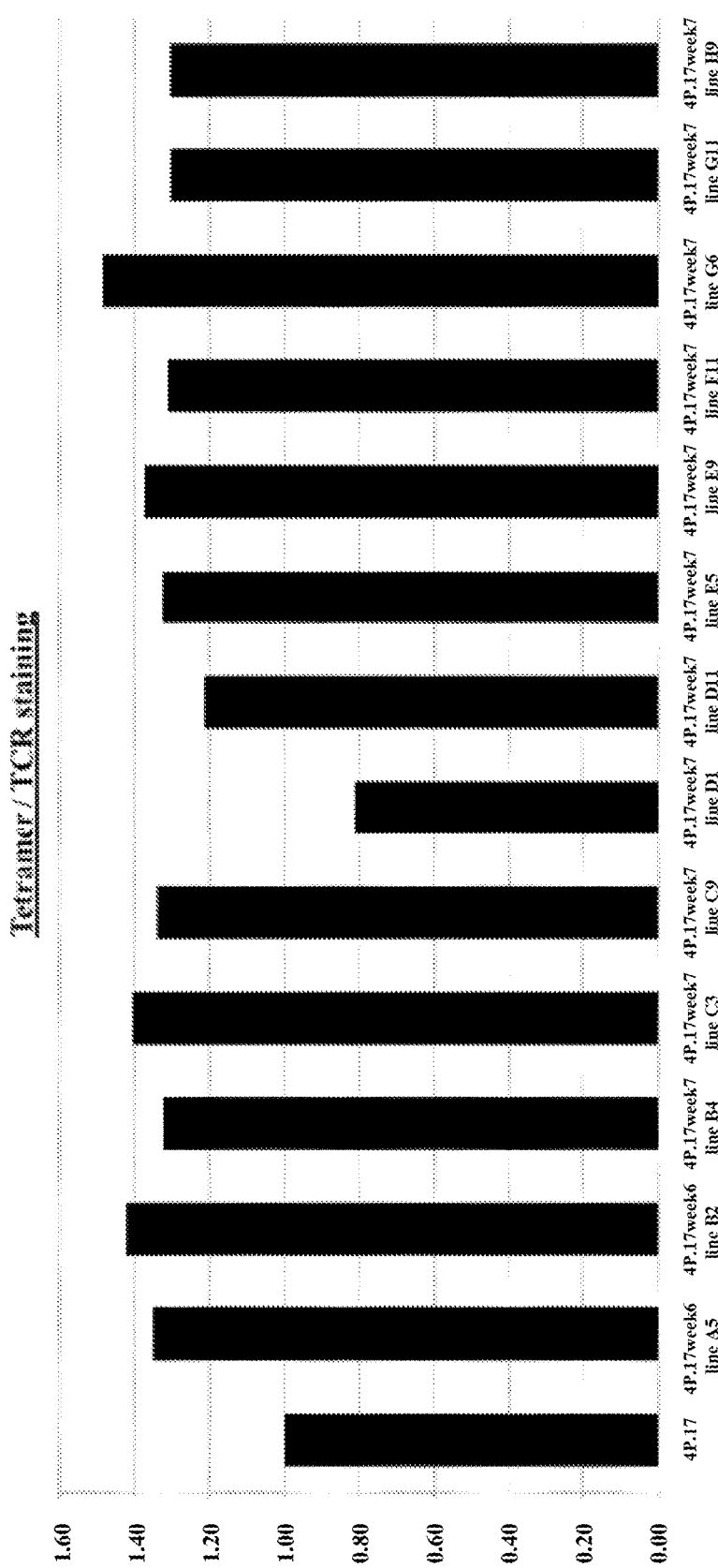
Figure 22B:
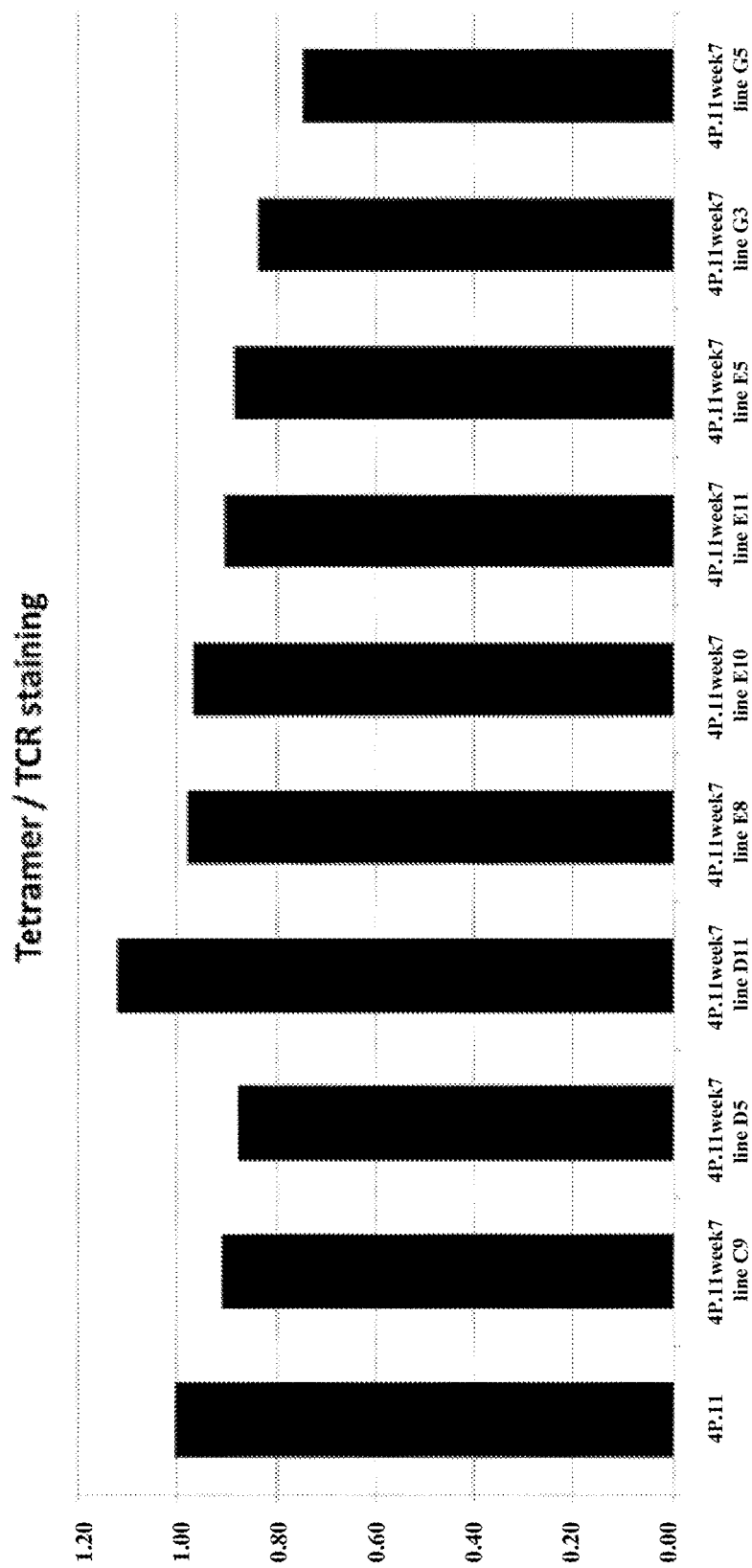

FIGS. 22A-22B are a graphic representation of Tetramer/TCR staining of different colonies that were cultured from cells sorted for high TCR affinity after 6 or 7 weeks of AID induction. The original cell lines are 4P.17 (FIG. 22A) and 4P.11 (FIG. 22B).

Figure 23:
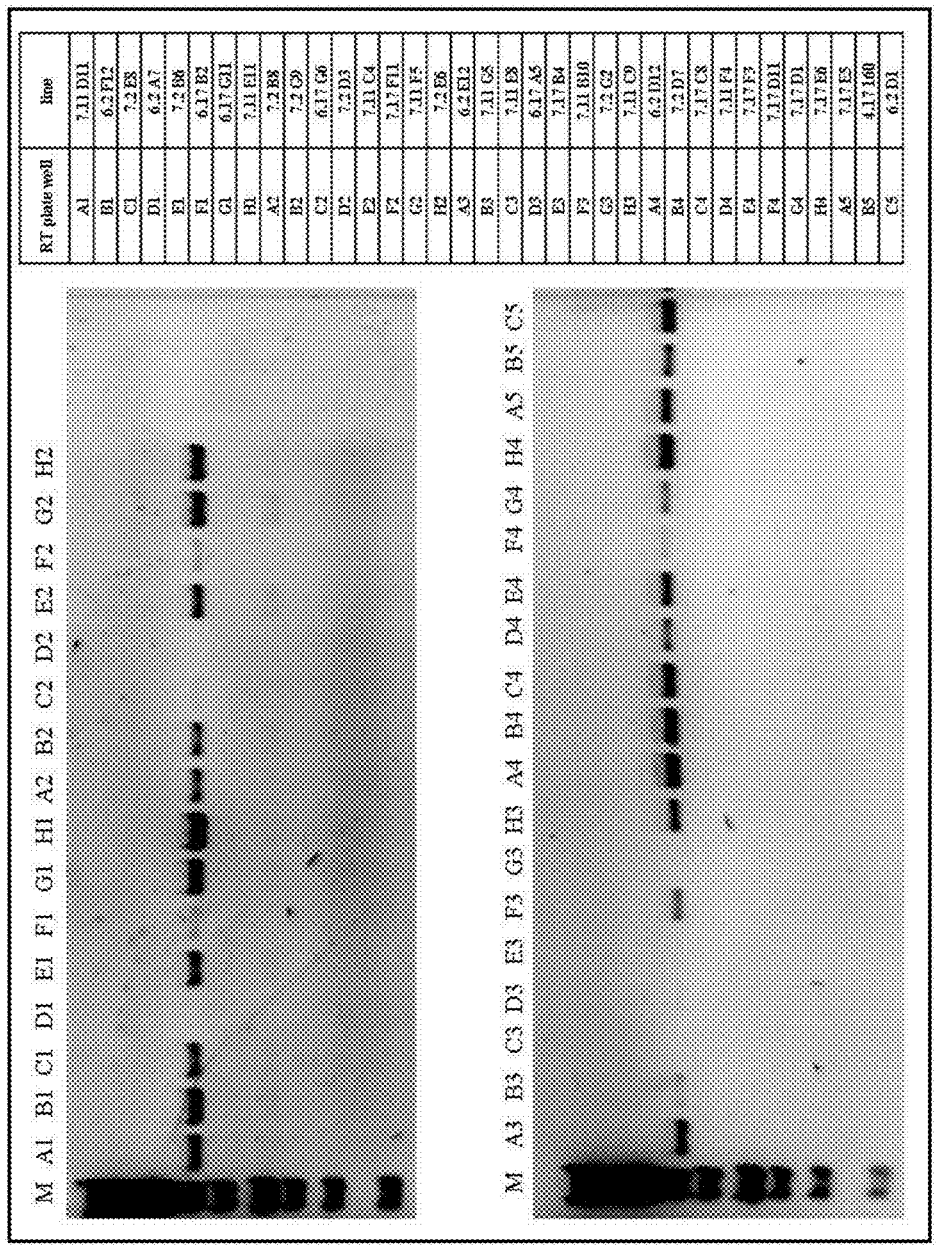

FIG. 23 shows agarose gel run of TCR segment amplified by PCR from first strand cDNA synthetized from RNA extracted from different sorted colonies.

Figure 24:
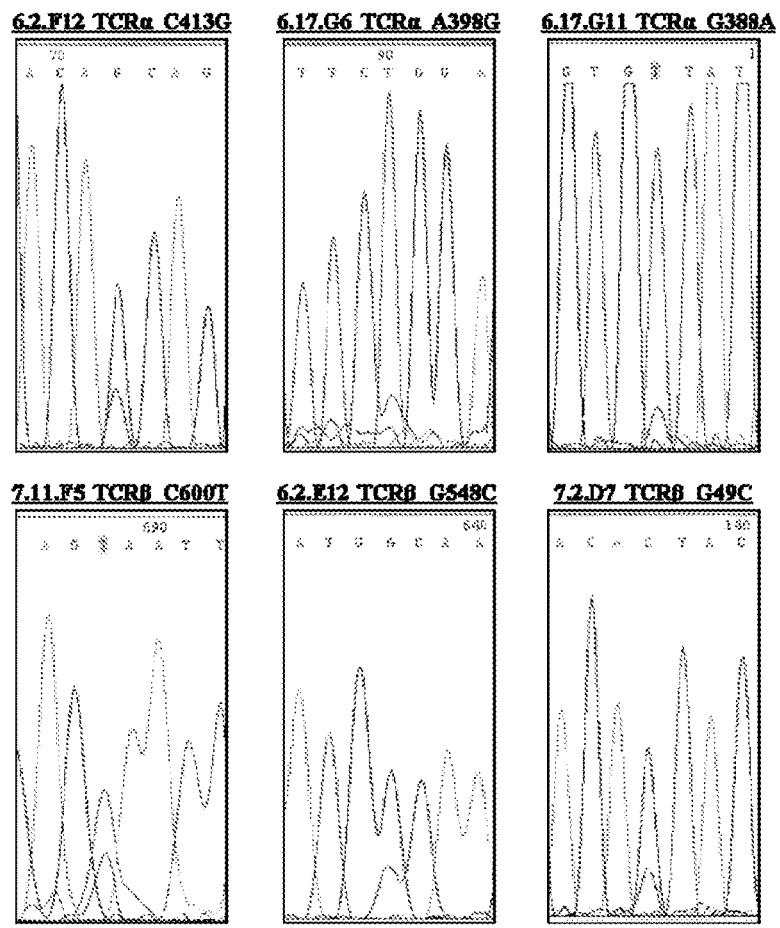

FIG. 24 depicts sequencing chromatographs of some of the mutations found in sequencing of the different colonies.

FIG. 25 depicts the mRNA cds sequence of mouse CD3 delta (SEQ ID NO: 16), CD3 epsilon (SEQ ID NO: 16), CD3 gamma (SEQ ID NO: 16), and CD3 zeta (SEQ ID NO: 16) used in the experiments.

Figure 26:
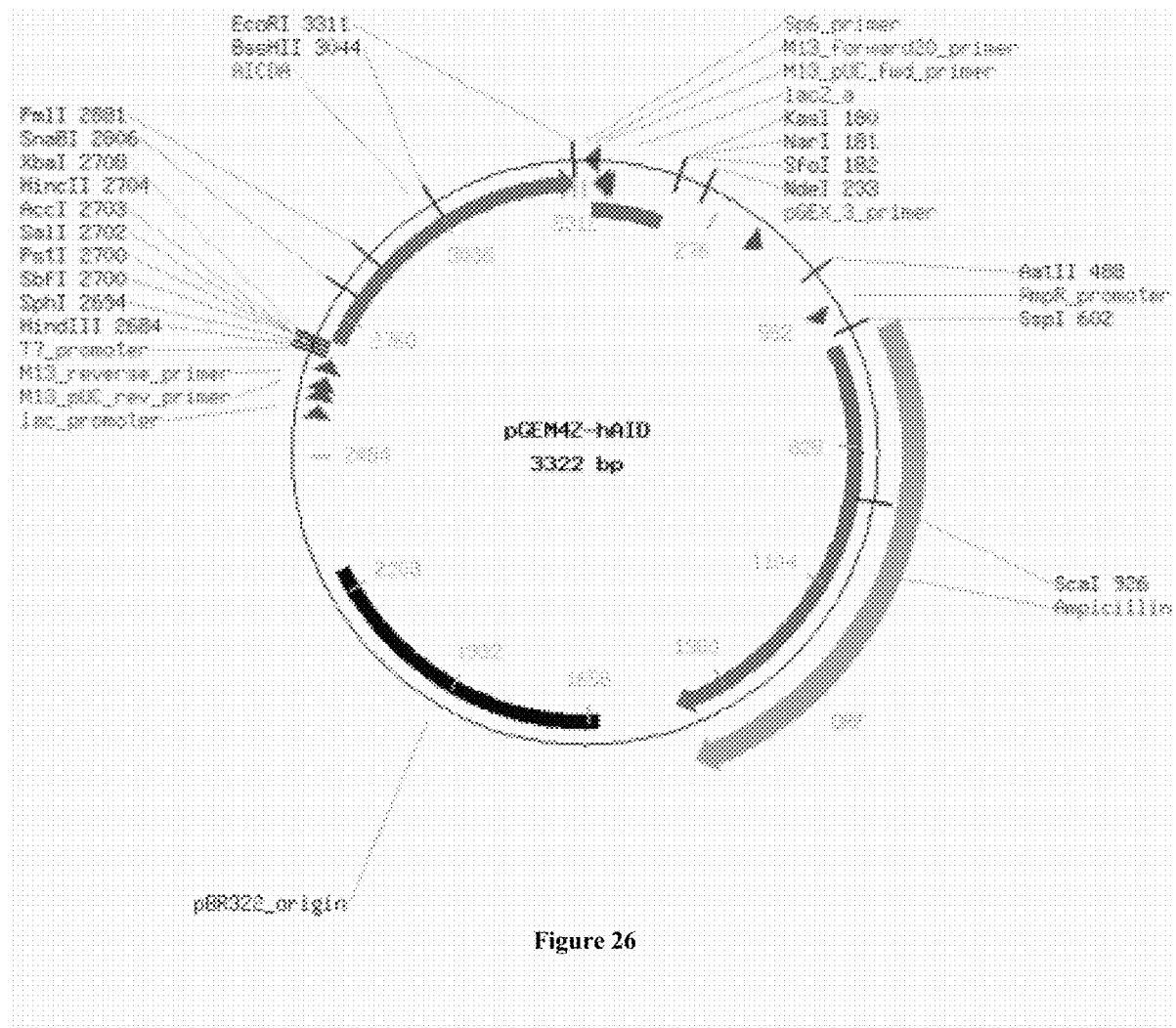

FIG. 26 depicts the pGEM4z-hAID vector for in-vitro transcription of hAID-mRNA.

Figure 27:
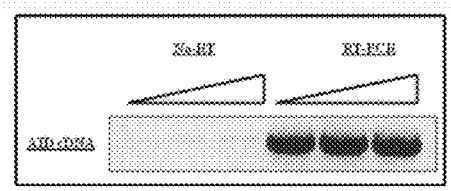

FIG. 27 depicts RT-PCR of AID-mRNA transcription of pGEM4z-hAID vector with Epicenter in-vitro expression system.

Figure 28:
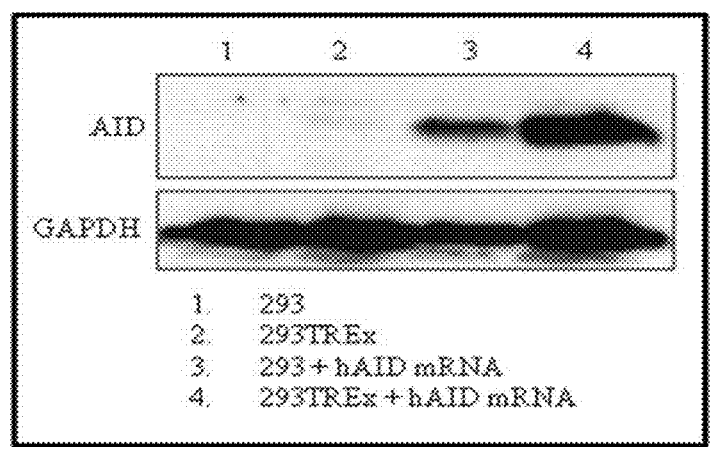

FIG. 28 is a Western blot analysis of 293HEK and 293TREx cells that were electroporeted with, or without AID-mRNA. Line 1 shows 283 cells, line 2 shows the 293TREx cells, line 3 shows the 293+hAID+mRNA cells, and line 4 shows 293TREx+hAID mRNA cells.

Figure 29:
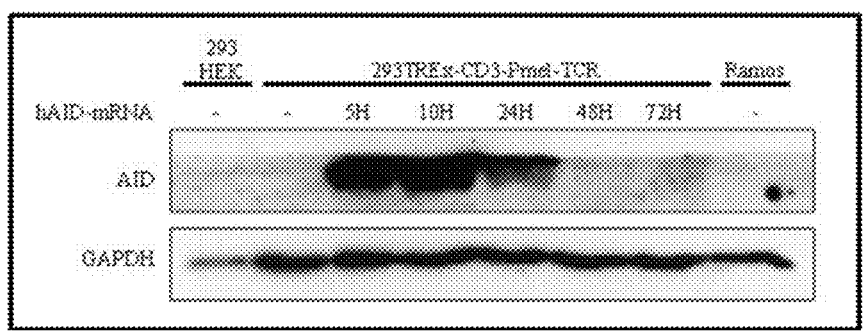

FIG. 29 is a Western blot analysis of 293TREx-CD3-Pmel-TCR that were, or were not electroporated with AID-mRNA. The samples were collected at different time points post electroporation. 293HEK cells were used as a negative control.

Figure 30:
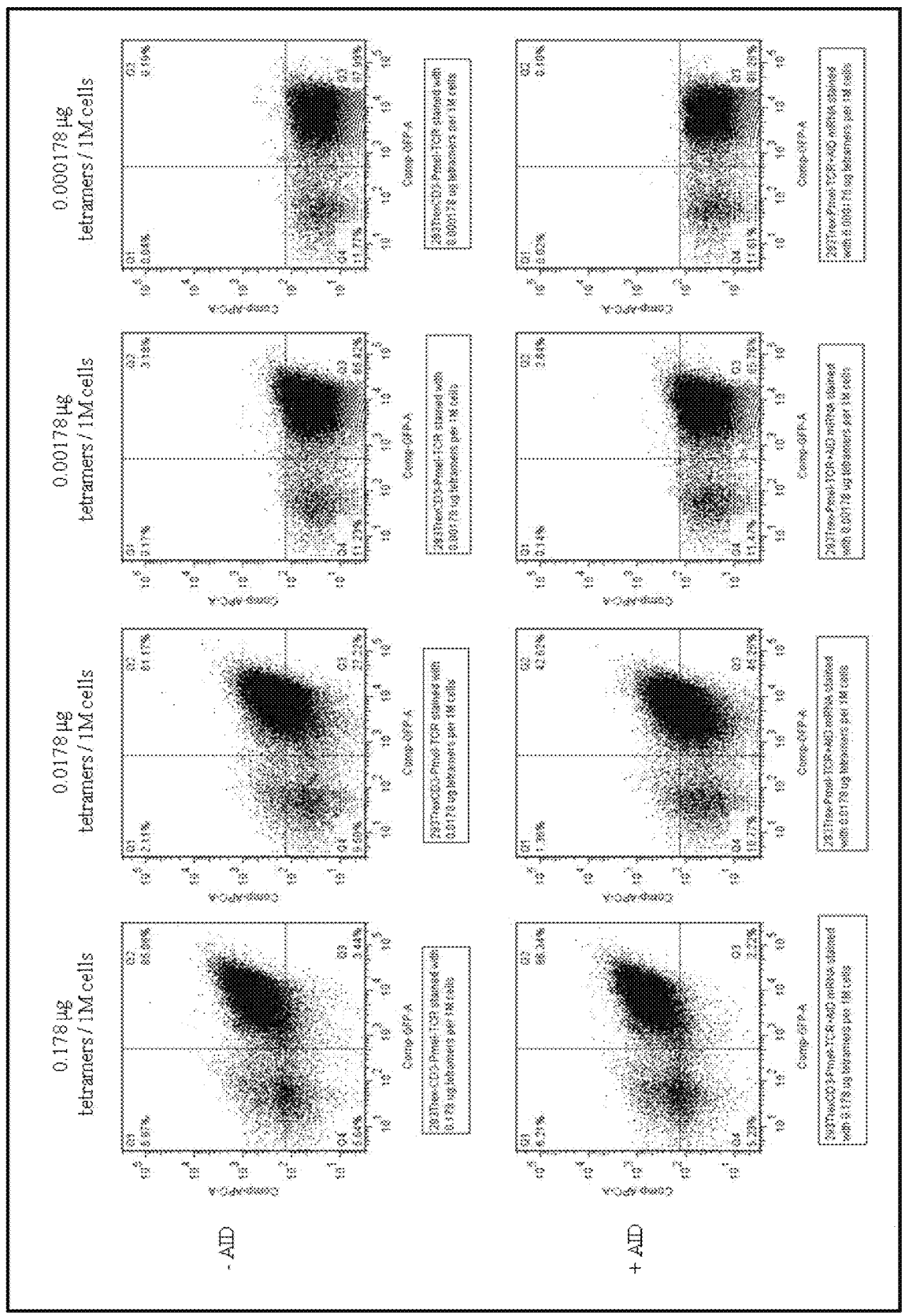

FIG. 30 shows FACS analysis of 293TREx-CD3-Pmel-TCR cells electroporeted with or without AID mRNA, stained with several decimal dilutions of tetramers.

Figure 31:
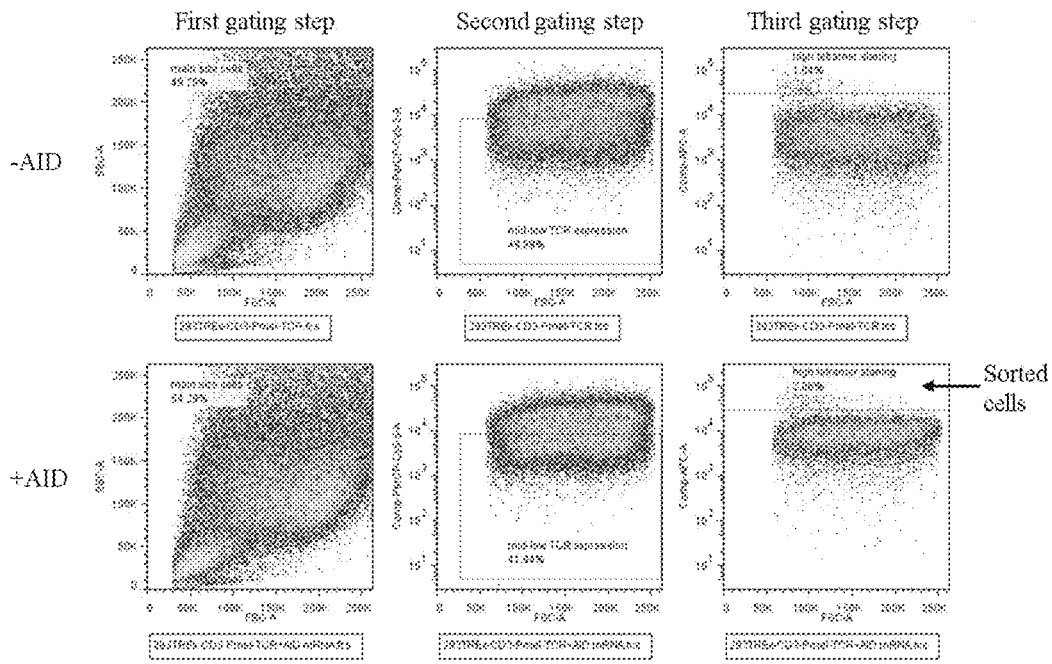

FIG. 31 shows gating steps for sorting 293TREx-CD3-Pmel-TCR cells 72H after electroporation with AID mRNA. The cells were stained with tetramers and TCR antibody. Sorted cells are marked with an arrow.

Figure 32:
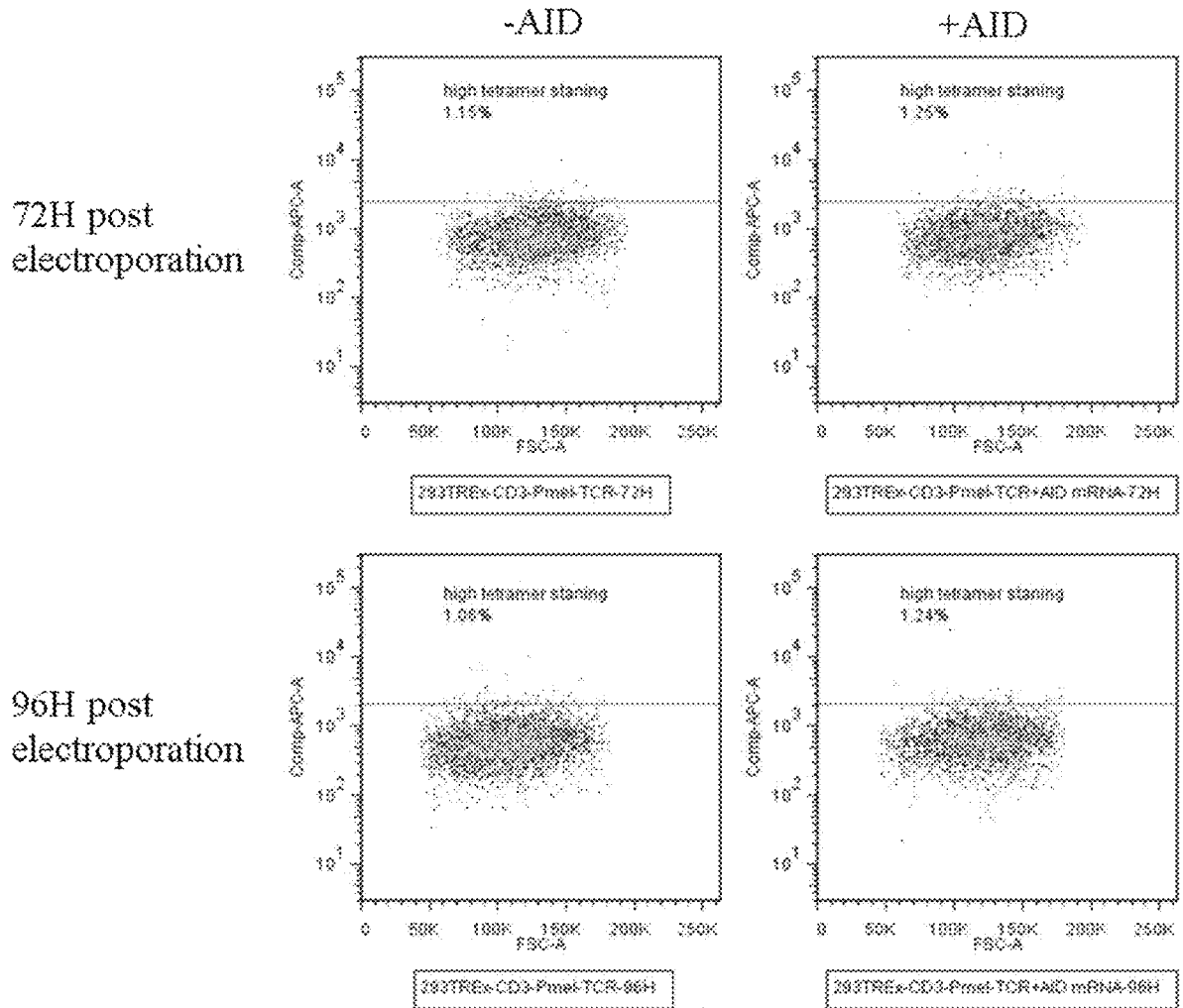

FIG. 32 depicts FACS analysis of 293TREx-CD3-Pmel-TCR cells that were electroporated with or without AID mRNA. The analysis is done 72 or 96 H after electroporation.

Figure 33:
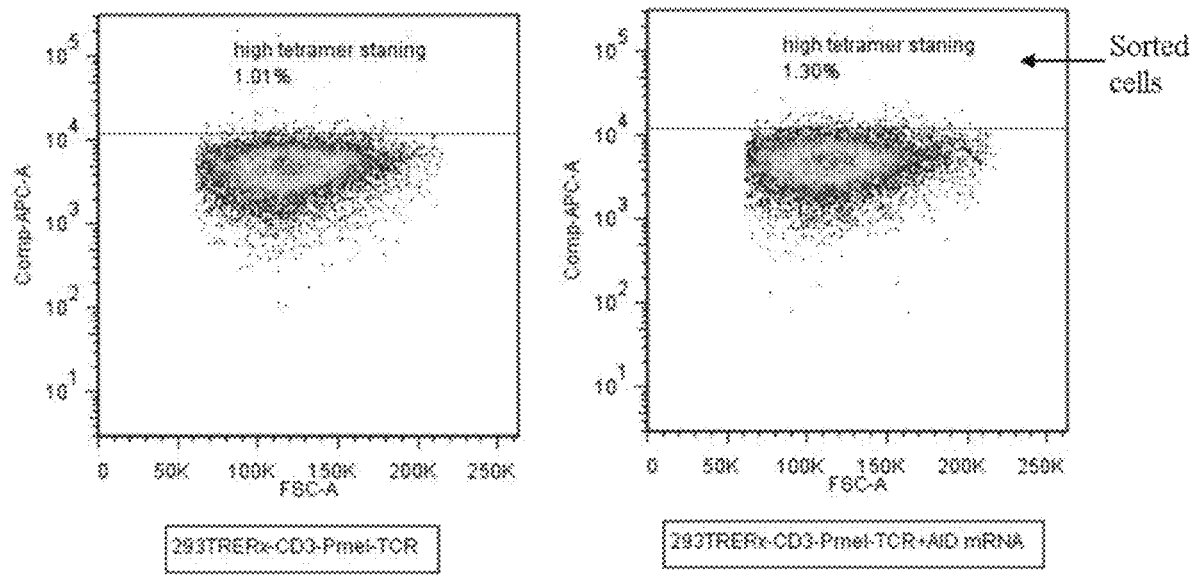

FIG. 33 depicts FACS analysis of 293TREx-CD3-Pmel-TCR cells that were electroporated with or without AID mRNA. The analysis is done 72H after electroporation.

Figure 34:
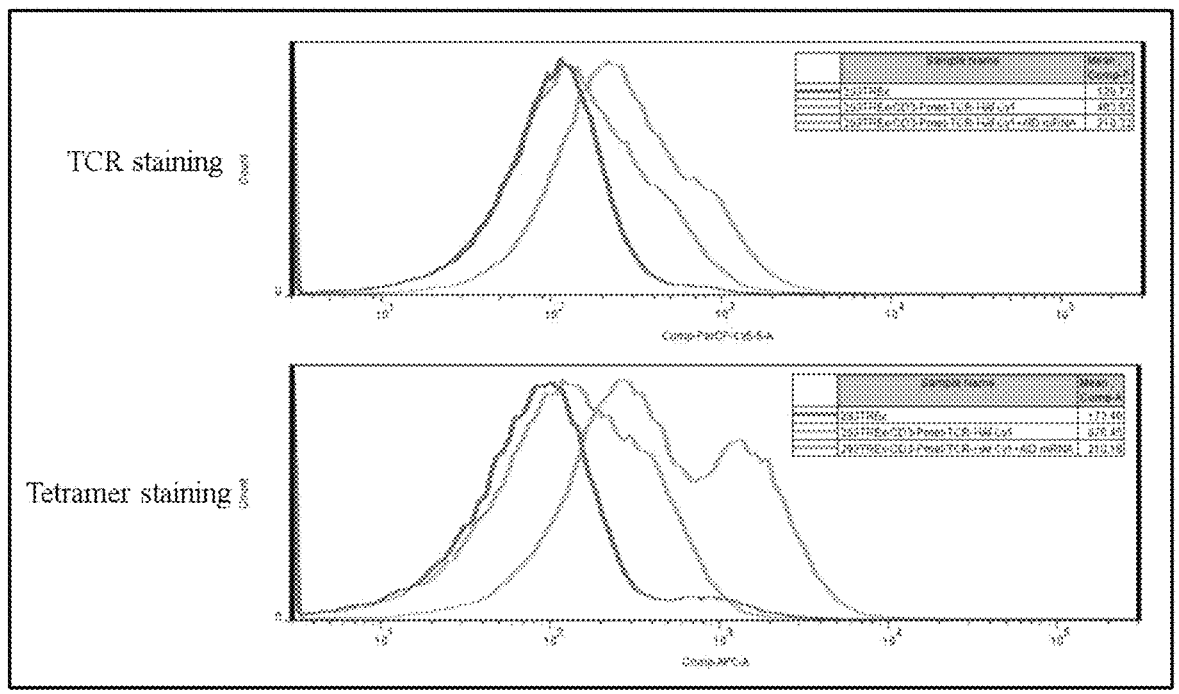

FIG. 34 depicts FACS analysis of 293TREx-CD3-Pmel-TCR-HAf Cy1 electroporated with AID mRNA and stained by tetramers and TCR antibody.

Figure 35:
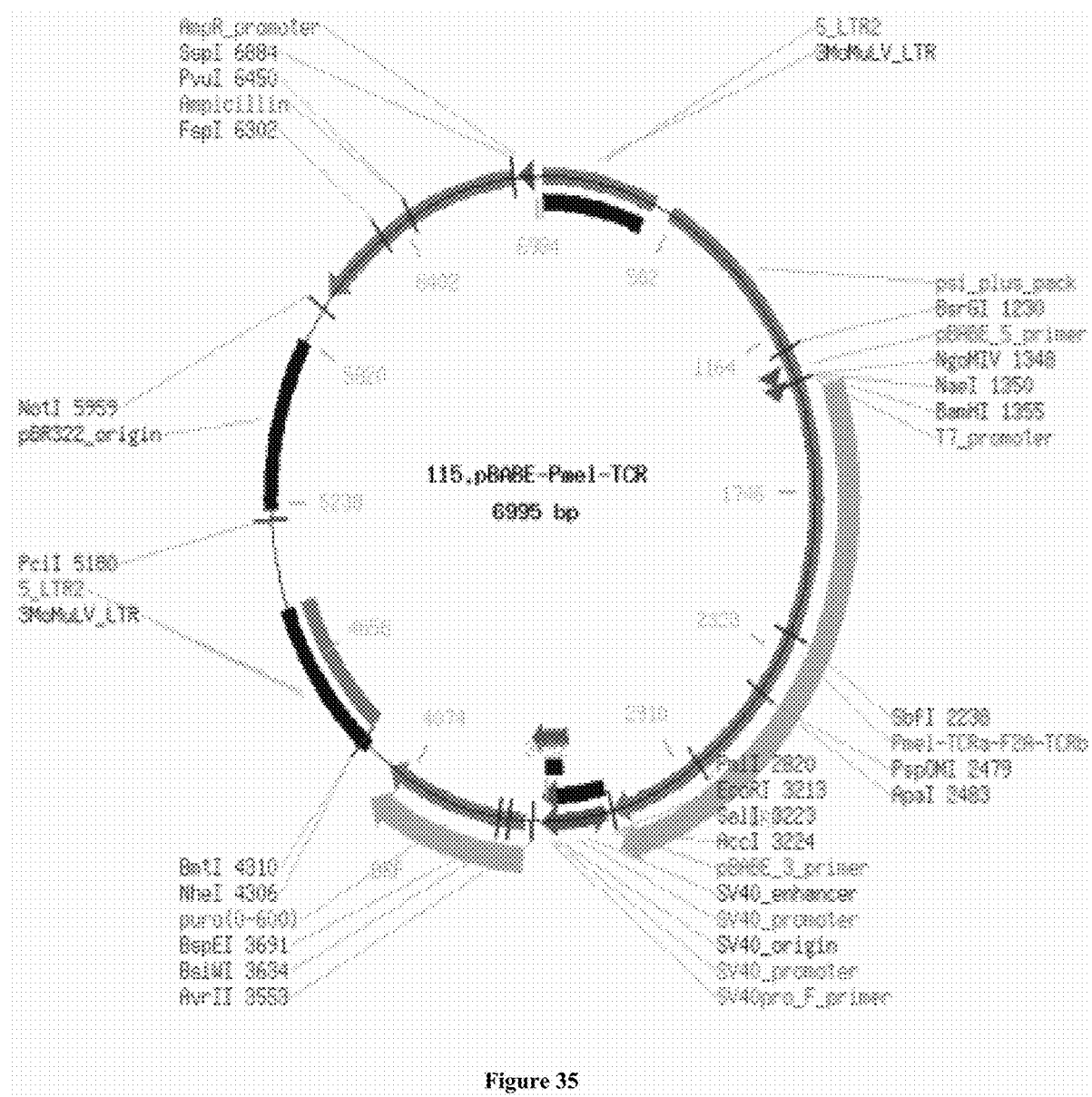

FIG. 35 depicts the pBABE-Pmel-TCR expression vector map.

Figure 36:
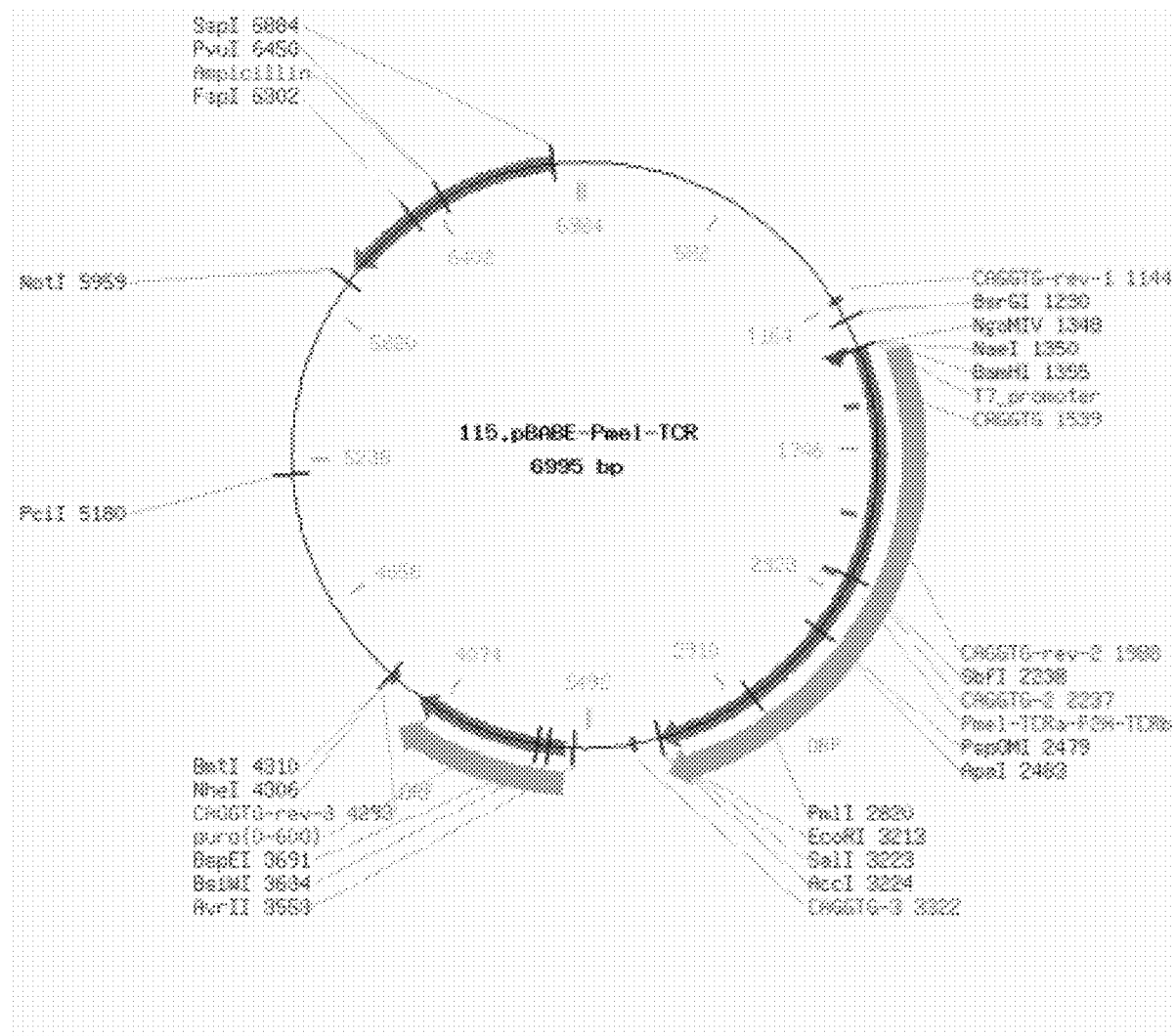

FIG. 36 is a Fuzznuc analysis of pBABE-Pmel-TCR showing six CAGGTG motifs.

Figure 37:
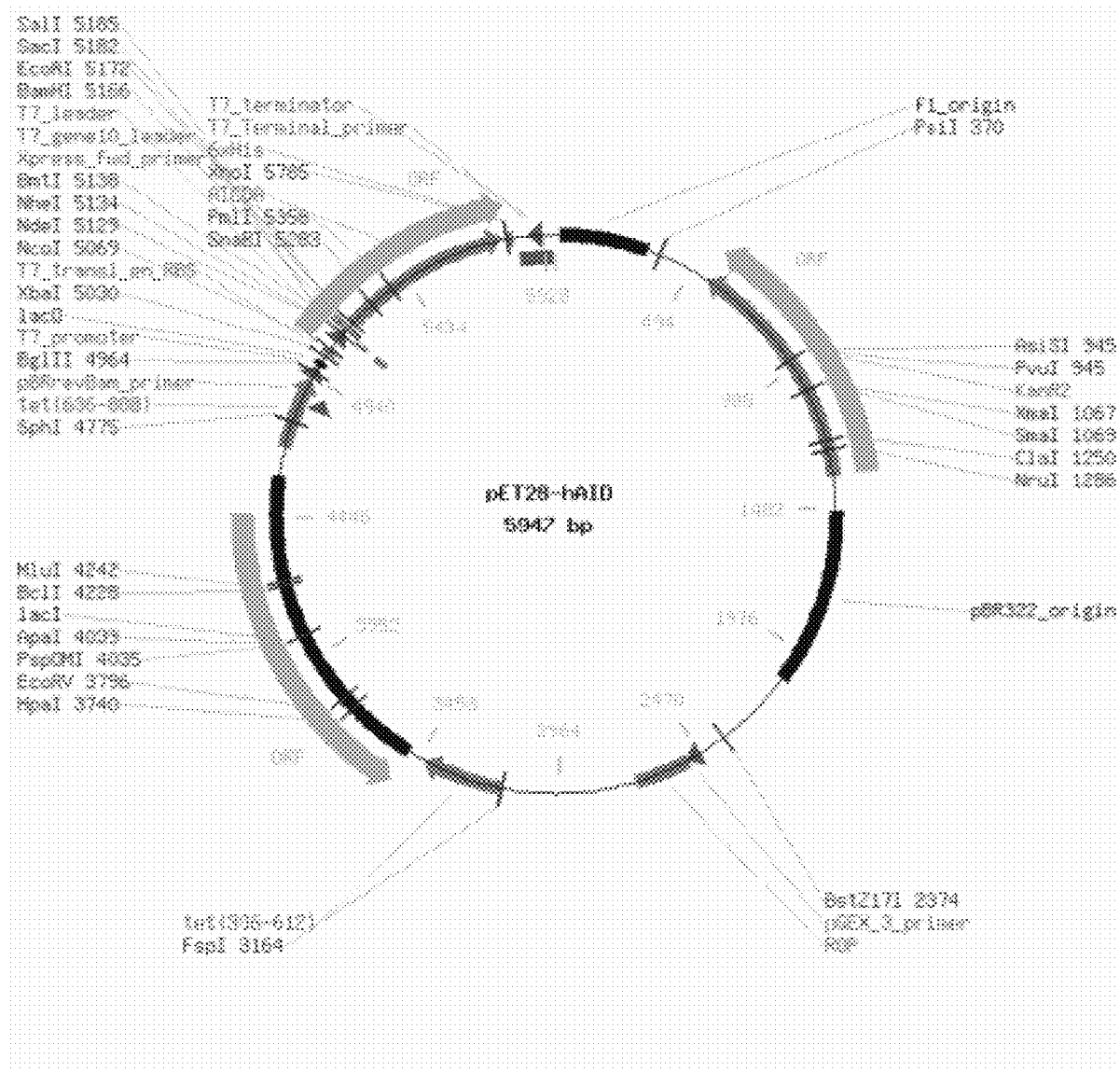

FIG. 37 depicts the pET28-hAID vector.

Figure 38A:
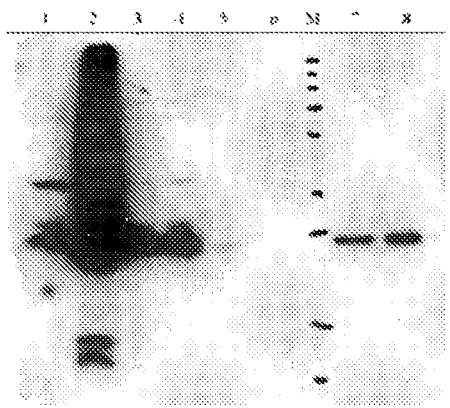
Figure 38B:
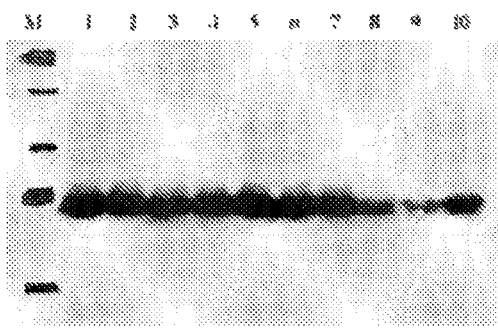
Figure 38C:
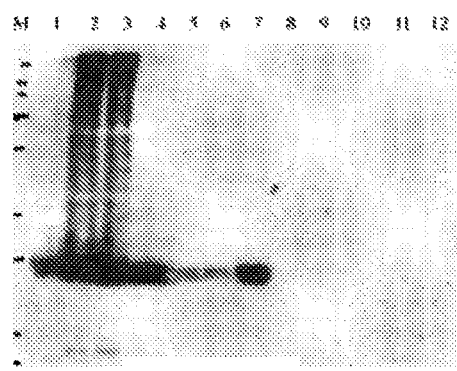

FIGS. 38A-38C show Western blot analysis for detecting recombinant AID production and purification from Rosetta bacteria. FIG. 38A. at 37° C. with 1 mM IPTG (lines: 1—bacteria before addition of IPTG; 2—bacteria after 3 H of incubation with IPTG; 3—clarified sample before binding to beads; 4—clarified sample after binding to beads; 5—first wash; 6—second wash; M-protein size marker; 7—Elution 1; 8—Elution 2). FIG. 38B. at 16° C. with different concentrations of IPTG (lines: 1-1 mM IPTG; 2-500 µM IPTG; 3-1001 µM IPTG; 4-50 µM IPTG; 5-10 µM IPTG; 6-5 µM IPTG; 7-1 µM IPTG; 8-500 nM IPTG; 9-100 nM IPTG; 10-500 nM IPTG).

FIG. 38C. at 16° C. and 1 µM of IPTG (lines: 1—bacteria before addition of IPTG; 2—bacteria after night incubation with 1 µM IPTG; 3—clarified sample before binding to beads; 4—clarified sample after binding to beads; 5—first wash; 6—second wash; 7—Elution 1; 8—other elutions).

Figure 39:
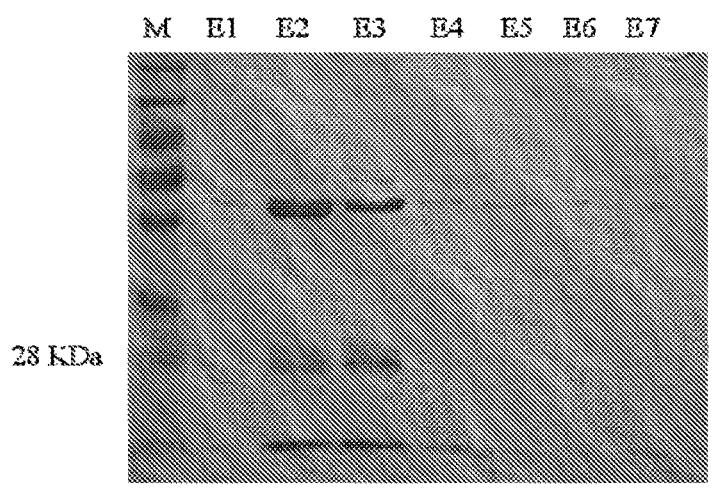

FIG. 39 depicts coomassie staining of SDS-PAGE resolution of eluted recombinant AID.

Figure 40A:
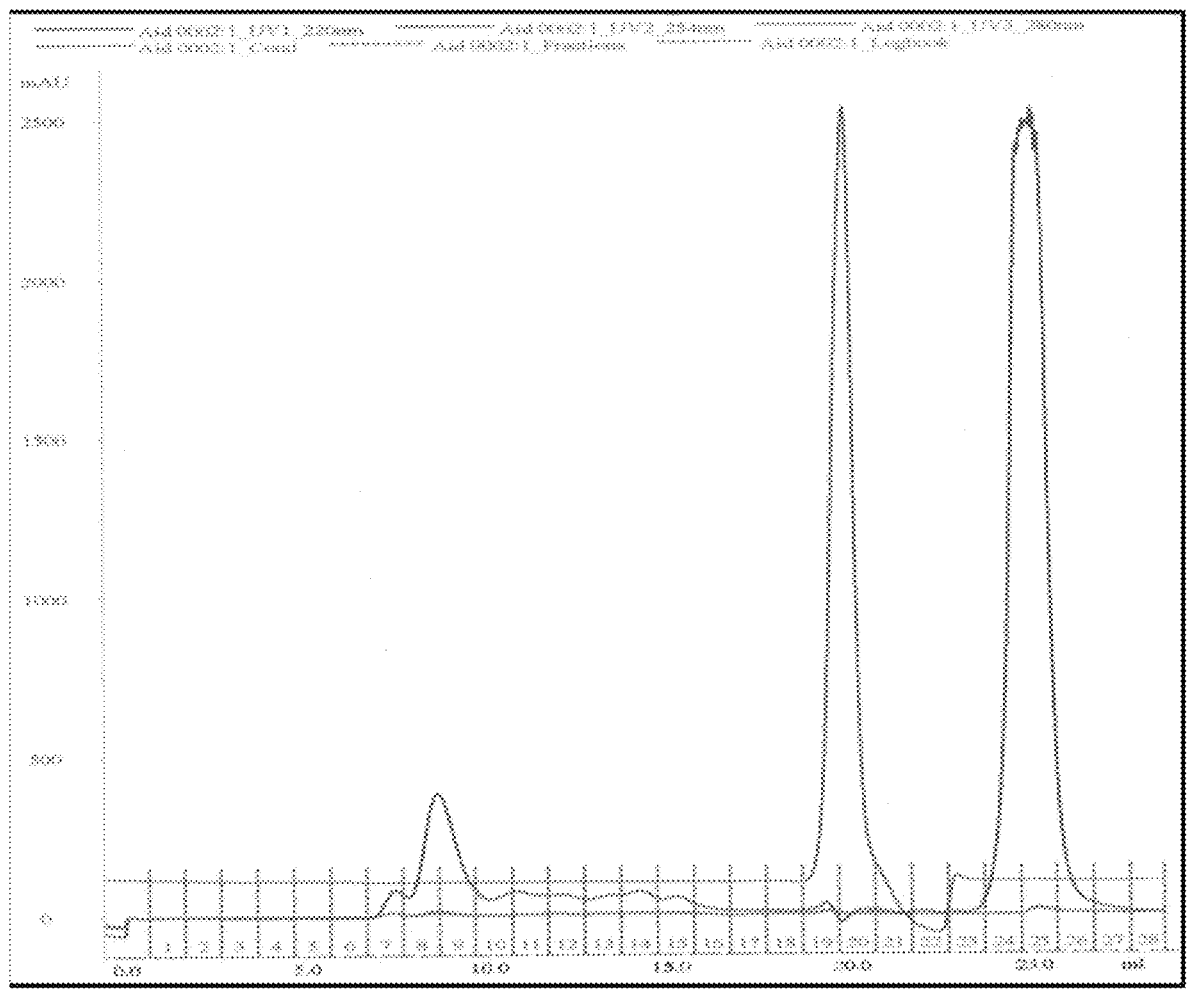
Figure 40B:
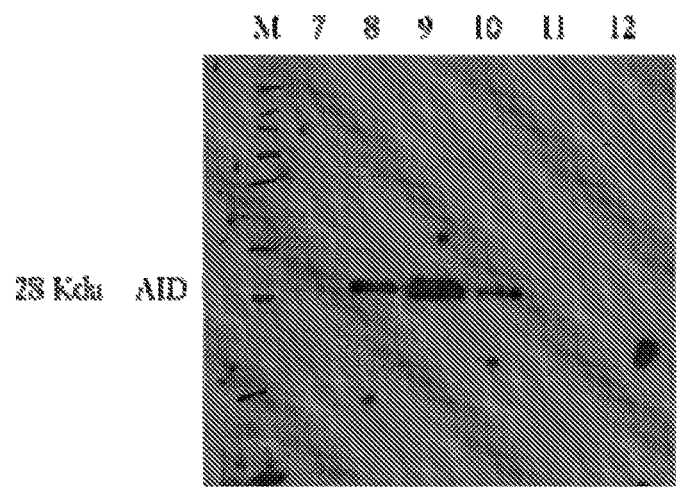
Figure 40C:
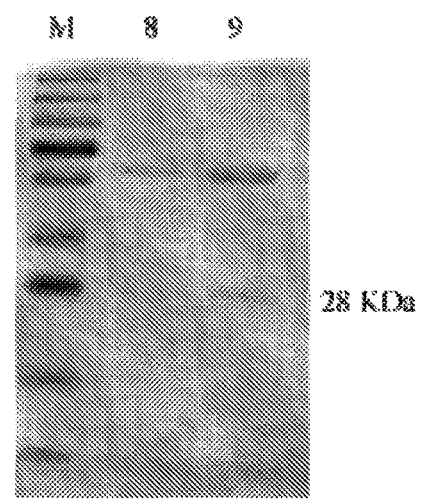

FIG. 40A shows FPLC purification of relevant elution of recombinant AID, relevant pick can be seen in fractions 7-15. FIG. 40B. Fractions 7-12 were analyzed by western blot, AID can be detected in fractions 8-10. FIG. 40C. Fractions 8-9 were further analyzed by Coomassie staining.

DESCRIPTION OF SPECIFIC EMBODIMENTS OF THE INVENTION

The present invention provides affinity maturation systems and methods for increasing the affinity of a T cell receptor (TCR) to its ligand. Particularly, the methods of the present increase the affinity of a TCR to its ligand by subjecting TCR genes to somatic hypermutation (SHM), directed by the mutator enzyme Activation Induced cytidine Deaminase (AID). The present invention further provides affinity maturated TCRs (in cell-bound or in soluble form) and pharmaceutical compositions comprising same useful in treating cancer, e.g., by anti-tumor immunotherapy.

Effective T cell activation depends, among other factors, on the functional avidity of the peptide-MHC complex (pMHC) to the TCR, i.e. on the affinity and the number of pMHC-TCR contacts. Since the T cell repertoire is controlled by negative and positive selection in the thymus, naturally occurring TCRs have mostly low affinities, in the range of 1-100 µM. Moreover, unlike antibodies whose affinities improve over time by SHM, TCR do not undergo SHM.

As exemplified herein below the affinity of a TCR to its ligand may be increased remarkably by subjecting TCR genes to SHM, directed by AID. The human AID has, in one embodiment, the mRNA sequence as set forth in SEQ ID NO: 3 (GI 224451012), and correspondingly, an amino acid sequences as set forth in SEQ ID NO:4 (GI 10190700). In some embodiments, a homolog, an analog, a fragment or derivative of human AID is used in the methods of the invention.

According to some embodiments, the present invention provides a method for increasing the affinity of a TCR to its ligand, the method comprising the steps of:
(i) expressing in a host cell a nucleic acid construct encoding a TCR gene or fragment thereof,
(ii) mutating the TCR gene or fragment thereof using SHM, and
(iii) selecting cells expressing a TCR with high affinity to a ligand.

In another embodiment, the TCR gene encodes a TCRα chain and a TCRβ chain. In one embodiment, the TCR gene is a human TCR gene. In a particular embodiment, the TCR gene of step (i) has a low affinity to the ligand.

The term "low affinity", as used herein refers to an affinity in the range of about 1-100 µM. It is apparent to those skilled in the art that TCR sequences vary and are dependent according to their reactivity to a specific antigen, presented in a peptide-MHC complex. For instance, in the examples herein below, SEQ ID NO:1 and SEQ ID NO:2 represent the TCRα and TCRβ chains which are specific for the H2-D MHC-I presenting the gp100 antigen. Thus, the TCR gene of step (i) is a TCR having a low affinity to the ligand (e.g., cancer antigens) for which the affinity maturated TCR are requested.

The term "affinity maturated" as used herein refers to a TCR that is derived from a reference TCR, e.g., by mutation, binds to the same antigen as the reference TCR; and has a higher affinity for the antigen than that of the reference TCR.

Typically, the affinity maturated TCR binds to the same epitope as the initial reference antibody.

An "affinity maturation system" of the invention refers to a system for engineering and selecting affinity naturated TCRs (i.e., TCRs with improved affinity to a ligand relative to a starting TCR). As described herein, the affinity maturation system of the invention subject TCR genes to somatic hypermutation using the mutator enzyme AID.

The term "increasing the affinity of a TCR to its ligand", as used herein refers to increasing TCR's affinity to its ligand by at least 140%, at least 150%, at least 160%, at least 180%, at least 190% or at least 200% as compared to the affinity of the reference TCR to the same ligand (i.e., prior to subjecting the methods of the present invention).

In some embodiments, the affinity maturated TCRs of the invention exhibit a dissociation constant lower than 100 nanomolar for a selected ligand. In another embodiment, the affinity maturated TCRs of the invention exhibit a dissociation constant lower than 90 nanomolar for a selected ligand. In another embodiment, the affinity maturated TCRs of the invention exhibit a dissociation constant lower than 80 nanomolar for a selected ligand. In another embodiment, the affinity maturated TCRs of the invention exhibit a dissociation constant lower than 70 nanomolar for a selected ligand. In another embodiment, the affinity maturated TCRs of the invention exhibit a dissociation constant lower than 60 nanomolar for a selected ligand. In yet another embodiment, the affinity maturated TCRs of the invention exhibit a dissociation constant lower than 50 nanomolar for a selected ligand.

Affinity Maturation Systems and Methods

Figure 1:
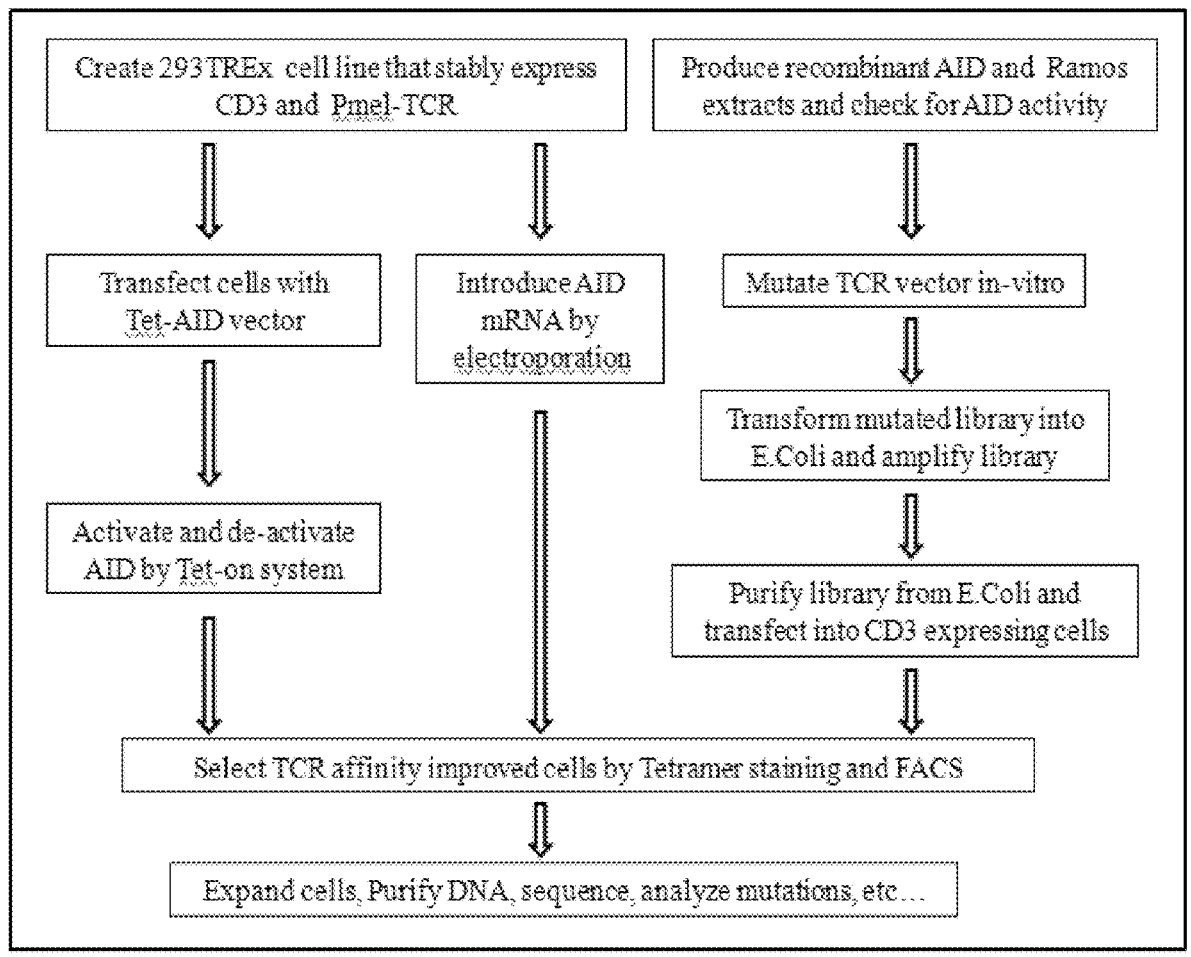
FIG. 1 is a diagram depicting the affinity maturation system design layout.

The affinity maturation system for the TCR can be performed by at least three diverse and parallel approaches (as depicted in FIG. 1):
1. Ex-vivo affinity maturation system, using Tet-regulated expression of AID.
2. Ex-vivo affinity maturation system, using controlled expression of AID by mRNA electroporesis.
3. In-vitro affinity maturation system, using extracts from cells that are in SHM and recombinant AID.

In the first and second approaches, the affinity maturation system is designed to take place in live cells. This is done in order to take advantage of the natural repair, transcription and replication mechanisms in the cells that are essential for SHM to have effect. For instance, 293HEK cell lines may be used for several reasons; first, this cell line does not express any of the TCR chains, this avoids problems of cross paring between exogenous and endogenous chains. Second, the 293HEK cells are very convenient cells to culture, transfect and modify.

The first step is to construct a cell line (e.g., 293HEK) that will stably express, properly fold and present the TCR on its cell membrane. The next step will be to induce AID expression in the cells. After AID expression, the cells will be analyzed for affinity maturation by tetramer staining and then sorted by FACS. The AID expression must be transient and controlled. If the AID expression is not stopped before the affinity maturation analysis, the TCR might continue to mutate after analysis and sorting.

The transient expression of AID is achieved in the first and second approaches by two different ways. In the first approach, the transient expression of AID is controlled with a Tet-on system. The TCR construct is build in 293TREx cells. These cells are constantly expressing Tet repressor protein. In this approach, AID expression is repressed by the Tet repressor protein until Tetracycline (or its analog Doxycycline) is introduced into the medium. In the second approach the transient expression of AID is achieved by electroporation of AID-mRNA into the cells, the mRNA will be translated in the cells and degraded after a relatively short time.

In the third approach, the mutagenesis reaction takes place in-vitro. The TCR genes are cloned into a retroviral expression vector. This vector will be mutated in-vitro by recombinant AID and nuclear extracts from a hypermutating cell line called Ramos. The result of the mutation reaction will be a library of differently mutated vectors. The vector library will be amplified by transformation into bacteria, grown in liquid media and the plasmids will be extracted. After amplification the library will be packaged into retroviruses and infected into 293HEK cells. The infected cells will be analyzed for affinity matured TCR by tetramer staining and sorted by FACS.

The activity of T cells is regulated by antigen, presented to a T cell in the context of a major histocompatibility complex (MHC) molecule. The T cell receptor (TCR) then binds to the MHC-peptide complex. Once antigen is complexed to MHC, the MHC-antigen complex is bound by a specific TCR on a T cell, thereby altering the activity of that T cell. The TCR complex is thus an attractive target for immunomodulation.

TCRs are members of the immunoglobulin superfamily and usually consist of two subunits, namely the α- and β-subunits. These possess one N-terminal immunoglobulin (Ig)-variable (V) domain, one Ig-constant (C) domain, a transmembrane/cell membrane-spanning region, and a short cytoplasmic tail at the C-terminal end. The variable domains of both the TCR α-chain and β-chain have three hypervariable or complementarity determining regions (CDRs), whereas the variable region of the 1-chain has an additional area of hypervariability (HV4) that does not normally contact antigen and therefore is not considered a CDR.

The TCR complex of the majority of the mature T cells is a TCRcαβ heterodimer associated to the γ, δ, ε and ζ chains of CD3. This complex is stabilized by interactions between the transmembrane domain of the TCR chains and CD3 subunits. The interaction of the TCR with a peptide presented by MHC induces a conformational change in the TCR that triggers CD3 phosphorylation.

In some embodiments, the CD3 is a human CD3. In some embodiments, the CD3 chain comprises at least one CD3 chain selected from SEQ ID NO: 20 to SEQ ID NO:23. In one embodiment, the human CD3 epsilon chain (NM_000733) is set forth in SEQ ID NO: 20. In another embodiment, the human CD3 gamma chain (NG_007566) is set forth in SEQ ID NO: 21. In another embodiment, the human CD3 delta chain (NG_009891) is set forth in SEQ ID NO: 22. In another embodiment, the human CD3 zeta chain is set forth in SEQ ID NO: 22.

In some embodiments, the CD3 is a murine CD3. In some embodiments, the CD3 chain comprises at least one CD3 chain selected from SEQ ID NO: 16 to SEQ ID NO:19.

In one embodiment, the murine CD3 delta chain (gi 227498960) is set forth in SEQ ID NO: 16. In another embodiment, the murine CD3 epsilon chain (gi 158508719) is set forth in SEQ ID NO: 17. In another embodiment, the murine CD3 gamma chain (gi 160333908) is set forth in SEQ ID NO: 18. In another embodiment, the murine CD3 zeta (gb J04967.1) chain is set forth in SEQ ID NO: 19.

As used herein, "T cell receptor" or "TCR" refers to a surface protein of T cell that allows the T cell to recognize an antigen including an epitope thereof. A TCR functions to recognize an antigenic determinant and to initiate an immune response. A TCR also allows a T cell to recognize an infected cell. The term "B-cell" as used herein is defined as a cell derived from the bone marrow and/or spleen. B cells can develop into plasma cells which produce antibodies.

Effective T cell activation depends, inter alia, on the functional avidity of the "peptide-MHC complex" or pMHC to the TCR, and particularly on the affinity and the number of pMHC-TCR contacts. According to some embodiments of the present invention, it is required to determine the capability of the TCR to bind the MHC-class I molecule presenting an antigen, thereby select TCRs with improved affinity. Preferably, testing the binding capability of a TCR is performed using a tetramer staining assay.

The tetramer staining assay is designed for testing TCR-MHC binding (Ogg and McMichael, 1998). Briefly, the tetramer is a complex of four monomers. Each monomer formed from a MHC-class I molecule (e.g., H-2D$^b$) presenting an antigen (e.g., the human gp100 peptide KVPRNQDWL as used in the examples below). The skilled artisan will understand that said staining assay may be designed using other oligomers (instead of said tetramer), for instance, pentamers, hexamers, hepatmers, octamers nonamer or decamers. Preferably, the MHC-I molecule is conjugated to a biotin molecule. The tetramers are assembled by linking four biotin conjugated monomers to one molecule of APC-conjugated Streptavidin. The TCR expressing cells are then stained with the tetramers and analyzed (e.g., for TCR antigen binding) by FACS.

The term "antigen" or "Ag" as used herein is defined as a molecule that provokes an immune response. This immune response may involve either antibody production, or the activation of specific immuno logically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another.

An "antigen presenting cell" (APC) is a cell that is capable of activating T cells, and includes, but is not limited to, monocytes/macrophages, B cells and dendritic cells (DCs). The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

The term "major histocompatibility complex" or "MHC" as used herein is defined as a specific cluster of genes, many of which encode evolutionarily related cell surface proteins involved in antigen presentation, which are among the most important determinants of histocompatibility. Class I MHC, or MHC-I, function mainly in antigen presentation to CD8 T lymphocytes. Class II MHC or MHC-II function mainly in antigen presentation to CD4 T lymphocytes. The MHC genes, which are also referred to as the HLA (human leukocyte antigen) complex, are located on chromosome 6 in humans.

The term "nucleic acid" as used herein refers to a polynucleotide of DNA or RNA of genomic or synthetic origin, which may be single- or double-stranded, and represent the sense or antisense strand. The term should also be understood to include, as equivalents, homologs of either RNA or DNA made from nucleotide analogs, and, as applicable to the embodiment being described.

An "isolated nucleic acid" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

As used herein "polynucleotide" or "oligonucleotide" sequences refer to polymers of deoxyribonucleotides, ribonucleotides, and modified forms thereof in the form of a separate fragment or as a component of a larger construct, in a single strand or in a double strand form. The polynucleotides to be used in the invention include sense and antisense oligonucleotide or polynucleotide sequences of DNA or RNA as appropriate to the goals of the therapy practiced according to the invention. The DNA or RNA molecules may be complementary DNA (cDNA), genomic DNA, synthesized DNA or a hybrid thereof or an RNA molecule such as mRNA. Accordingly, as used herein, the terms "DNA construct", "gene construct", "nucleic acid construct", "polynucleotide" and "oligonucleotide" are meant to refer to both DNA and RNA molecules. The term "oligonucleotide" refers to a polymer having not more than 50 nucleotides while the term "polynucleotide" refers to a polymer having more than 50 nucleotides. The term "nucleotide sequence" refers to both oligonucleotide sequence and polynucleotide sequence. The terms nucleotide sequence, oligonucleotide sequence and polynucleotide sequence are used in the invention interchangeably.

The term "gene" as used herein refers to a DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Nucleotide sequences for use in the invention can be obtained using hybridization methods well known in the art. DNA and RNA sequences may also be synthesized using automated nucleic acid synthesis equipment well known in the art. Use of the well-known polymerase chain reaction (PCR) is particularly preferred for generating mixtures of nucleotide sequences. Genomic nucleic acids may be prepared by means well known in the art such as the protocols described in Ausubel, et al., Current Protocols in Molecular Biology, Chapters 2 and 4 (Wiley Interscience, 1989). cDNA can be synthesized according to means well known in the art (see, e.g., Maniatis, et al., Molecular Cloning; A Laboratory Manual (Cold Spring Harbor Lab, New York, 1982).

A polynucleotide sequence can be deduced from the genetic code of a protein, however, the degeneracy of the code must be taken into account. Polynucleotides of the invention include sequences, which are degenerate as a result of the genetic code, which sequences may be readily determined by those of ordinary skill in the art.

As used herein, the term "gene construct" or "nucleic acid construct" refers to a DNA or RNA molecule that comprises a polynucleotide sequence which encodes a target protein and which may include initiation and termination signals operably linked to regulatory elements including a promoter and polyadenylation signal capable of directing expression in the cells of a subject. Thus, a gene construct contains the necessary regulatory elements operably linked to the polynucleotide sequence that encodes a target protein (e.g., TCRα and TCRβ chains, CD3 and AID), such that when present in a cell of the individual, the polynucleotide sequence will be expressed.

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. Selectable markers include, for example, sequences conferring antibiotic resistance markers, which may be used to obtain successful transformants by selection, such as ampicillin, tetracycline and kanamycin resistance sequences, or supply critical nutrients not available from complex media. Suitable expression vectors may be plasmids derived, for example, from pBR322 or various pUC plasmids, which are commercially available. Other expression vectors may be derived from bacteriophage, phagemid, or cosmid expression vectors, all of which are described in sections 1.12-1.20 of Sambrook et al., (Molecular Cloning: A Laboratory Manual. 3$^{rd}$ edn., 2001, Cold Spring Harbor Laboratory Press). Isolated plasmids and DNA fragments are cleaved, tailored, and ligated together in a specific order to generate the desired vectors, as is well known in the art (see, for example, Sambrook et al., ibid).

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a peptide or protein if transcription and translation of mRNA corresponding to that gene produces the peptide or protein in a cell or other biological system. Both the coding strand, the nucleotide sequence of which is identical to the mRNA sequence, and the non-coding strand, used as the template for transcription of a gene or cDNA, can be referred to as encoding the peptide or protein or other product of that gene or cDNA.

The regulatory elements necessary for gene expression of a DNA molecule include: a promoter, an initiation codon, a stop codon, and a polyadenylation signal. In addition, enhancers are often required for gene expression. It is necessary that these elements be operably linked to the polynucleotide sequence that encodes the target protein such that the polynucleotide sequence can be expressed in the cells of a subject and thus the target protein can be produced.

Initiation codons and stop codons are generally considered to be part of a polynucleotide sequence that encodes the target protein. However, it is necessary that these elements are functional in the subject to which the polynucleotide is administered.

Examples of promoters useful to practice the present invention include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV), promoters from human genes such as human actin, human myosin, human hemoglobin, human muscle creatine and human metalothionein and tissue-specific promoters such as involucrin, keratin 5, and keratin 14. Suitable protocols for use of promoters in construction of gene constructs are well known in the art (see, for example, Current Protocols in Molecular Biology, Chapter 1 (Wiley Interscience, 1989)) and are exemplified herein below.

In some embodiments, the expression of a specific gene, particularly AID, is controlled. Controlling gene expression is known in the art and has been reported for instance in Clackson, 1979 Curr. Opin. in Chem. Biol., 1997, 1:21 O-21 8; or in Saez et al. Curr. Opin. in Biotech., 1997, 8:608-616. In one embodiment, the expression of AID is transient, using e.g., an inducible promoter. An "inducible" promoter is a nucleotide sequence which, when operably linked with a polynucleotide which encodes or specifies a gene product, causes the gene product to be produced in a cell substantially only when an inducer which corresponds to the promoter is present in the cell. In one exemplary embodiment, the inducible promoter for the transient expression of AID is the Tet-on promoter. As is known in the art, the Tet-on promoter is induced by Tetracycline or Doxycycline.

Inducible mammalian promoters are known to those of skill in the art (see, e.g. Bitter et al. (1987) Methods in Enzymology 153: 516-544). Inducible promoters can be activated by external signals or agents. An inducible promoter is active when the inducer is present. The inducer may directly activate a promoter or inactivate a repressor of that promoter. For example, inducible systems endogenous to mammalian cells include promoters induced by heavy-metals (Brinster et al. Nature (1982) 296:39-42; Mayo et al. Cell (1982) 29:99-108; and Searle et al. Molecular and Cellular Biology (1985) 5:1480-1489), steroid hormones (Hynes et al. Proc. Natl. Acad. Sci. USA (1981) 78:2038-2042; Lee et al. Nature (1981) 294:228-232; and Klock et al. Nature (1987) 329:734-736), heat shock (Nouer, Heat Shock Response. Boca Raton, Fla., Ed. CRC, 1991) (reviewed in Mullick, A. and B. Massie Encyclopedia of Cell Technology pp. 1 140-1 164, 2000)) are well characterized. PCT publication WO2002/088346 discloses a cumate-inducible promoter. Additional inducible promoters are known in the art, and include, but are not limited to inflammation and hypoxia induced promoters.

Prokaryotic and insect inducible promoter systems have been adapted for regulated expression in mammalian cells. See, for example, Gossen et al. (1993) TIBS 18:471-475 and No et al. (1996) Proc. Natl. Acad. Sci. USA 93:3346-3351). The insect ecdysone-inducible promoter is tightly regulated with no detectable background expression in the absence of inducer. Ecdysone is suitable for use in vivo because it is a naturally occurring lipophilic steroid that can penetrate tissues, is inert in mammals and exhibits rapid clearance kinetics (No et al). Gupta et al. (PNAS (2004) 101: 1927-1932) discloses retroviral delivery of an ecdysone-inducible gene expression system under the control of a modified RNA polymerase Ill-specific U6 promoter.

The prokaryotic repressors from the lac and tet operons have been incorporated in eukaryotic inducible expression systems. Repression of expression is mediated by the repressor bound to operator sites placed downstream of the minimal promoter in the absence of inducer and repression is relieved on the addition of the inducer. (Brown et al. (1987) Cell 49:603-612; Hu and Davidson (1987) Cell 48:555-566; Blau and Rossi, Proc. Natl. Acad. Sci. USA (1999) 96:797-799; and Gossen et al. (1995) Science 268:1766-1769).

Methods for construction of expression cassettes containing an inducible promoter operatively linked to a coding sequence of any polypeptide are known to those of skill in the art, as are methods for introducing such expression cassettes and vectors containing such expression cassette into homing cells.

In addition to the regulatory elements required for DNA expression, other elements may also be included in the gene construct. Such additional elements include enhancers. The enhancer may be selected from the group including, but not limited to, human actin, human myosin, human hemoglobin, human muscle creatine and viral enhancers such as those from CMV, RSV and EBV.

Gene constructs can be provided with mammalian origin of replication in order to maintain the construct extrachromosomally and produce multiple copies of the construct in the cell. For instance, plasmids pCEP4 and pREP4 from Invitrogen (San Diego, Calif.) contain the Epstein Barr virus origin of replication and nuclear antigen EBNA-1 coding region, which produces high copy episomal replication without integration. Other plasmids known in the art may be used so long as the gene constructs express the target protein encoded by the polynucleotide sequence.

In order to be a functional gene construct, the regulatory elements must be operably linked to the polynucleotide sequence that encodes the target protein. Accordingly, it is necessary for the initiation and termination codons to be in frame with the coding sequence.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "homolog" refers to an oligonucleotide or polynucleotide or nucleic acid comprising at least one altered nucleotide base (nucleobase) by a nucleotide base substitution, addition, deletion, or chemical modification, as compared with the native oligonucleotide or polynucleotide or nucleic acid. In general, homologs typically will share at least 50% nucleotide identity to the native sequences of the present invention, in some instances the homologs will share at least 60% nucleotide identity, at least 70%, 80%, 90%, and in still other instances the homologs will share at least 95% nucleotide identity. The homology can be calculated using various, publicly available software tools developed by NCBI (Bethesda, Md.) that can be obtained through the internet. Exemplary tools include the BLAST system. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention. It is to be appreciated that the homologs of the present invention should exert similar or even higher activity than that exerted by the native or disclosed polynucleotide.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating LEDGF polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The expression vectors are introduced into the cells in a manner such that they are capable of expressing the isolated nucleic acid encoding the polypeptides of the present invention contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772:95-104, the contents of which are hereby incorporated by reference in their entirety), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640, the contents of which are hereby incorporated by reference in their entirety), papilloma virus vectors, picornavirus vectors, polyoma virus vectors, retroviral vectors, SV40 viral vectors, vaccinia virus vectors, and other vectors. Additionally, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated nucleic acid are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the nucleic acid of interest is introduced into the cells by any means appropriate for the transfer of DNA into cells. Many such methods are well known in the art (e.g., Sambrook et al., supra; see also Watson et al., 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion.

Cells, into which the nucleic acid has been transferred under the control of an inducible promoter if necessary, can be used as transient transformants. Such cells themselves may then be transferred into a subject for therapeutic benefit therein. Alternatively, particularly in the case of cells to which the vector has been added in vitro, the cells can first be subjected to several rounds of clonal selection (facilitated usually by the use of a selectable marker sequence in the vector) to select for stable transformants. Such stable transformants are then transferred to a subject, preferably a human, for therapeutic benefit therein.

Within the cells, the nucleic acid encoding the affinity maturated TCR of the present invention is expressed. Successful expression of the nucleic acid can be assessed using standard molecular biology techniques (e.g., Northern hybridization, Western blotting, immunoprecipitation, enzyme immunoassay, etc.).

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

In some embodiments, the methods of the present invention are performed by expressing the mutator gene Activation Induced cytidine Deaminase (AID) or analog thereof, with a TCR gene. The term "analog" includes any peptide having an amino acid sequence substantially identical to one of the sequences specifically shown herein (e.g., AID) in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another. Each possibility represents a separate embodiment of the present invention.

Pharmaceutical Compositions

The present invention provides a pharmaceutical composition comprising as an active ingredient a T cell expressing a TCR with a high affinity to a selected ligand (e.g., a TAA), and a pharmaceutically acceptable carrier. In other embodiments, the present invention provides a pharmaceutical composition comprising as an active ingredient a TCR with a high affinity to a selected ligand, and a pharmaceutically acceptable carrier.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. Preferred uses of the pharmaceutical compositions of the invention by injection are subcutaneous injection, intravenous injection, and intramuscular injection. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences by E. W. Martin, the contents of which are hereby incorporated by reference herein. Such compositions will contain a therapeutically effective amount of T cells of the present invention, together with a suitable amount of carrier so as to provide the form for proper administration to the subject.

The amount of the T cells of the present invention, which will be effective in the treatment of a particular disorder or condition (e.g., cancer) will depend on the nature of the disorder or condition and on the particular T cell expressing the affinity matured TCR, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the severity and responsiveness of the condition to be treated, dosing can also be a single administration of a slow release composition, with course of treatment lasting from several days to several weeks or until cure is effected or diminution of the disease state is achieved.

It is further understood that the compositions of the invention can be formulated or administered together with additional active ingredients as required to treat the condition of the patient.

The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For topical application, the compositions of the present invention can be formulated with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

The compositions of the present invention can be delivered in a controlled release system. Thus, an infusion pump can be used to administer the compositions such as the one that is used, for example, for delivering insulin or chemotherapy to specific organs or tumors. In yet another embodi-

Use of Affinity Maturated TCRs

In some aspects, the present invention provides methods for treating cancer in a subject comprising administering to said subject a pharmaceutically effective amount of a pharmaceutical composition comprising a an affinity maturated TCRs or a T cell expressing affinity maturated TCRs.

In additional aspects, the present invention provides pharmaceutical compositions comprising an affinity maturated TCRs or a T cell expressing same, for use in treating a disease or disorder such as cancer.

In yet another embodiment, the present invention provides use of an affinity maturated TCR or T cell expressing same, for the preparation of a medicament for treating a disease or disorder such as cancer.

The affinity of TCR's for a specific antigen makes them valuable for several therapeutic approaches, e.g., immunotherapy and particularly adoptive immunotherapy. As used herein "immunotherapy" refers to lymphocyte dependent immunotherapy (e.g., by tumor infiltrating lymphocytes). For example, cancer patients, such as melanoma patients, can be effectively treated by using adoptive cell therapy (ACT).

In order to extend the capacity to use adoptive cell therapy (ACT) to treat patients with more rapidly growing tumors, it is a goal to transfer enriched, antigen-specific effector T cells (both CD4 T helper cells and cytotoxic T lymphocytes) that have been selected for their ligand specificities to effectively attack tumor cells while avoiding serious attack of normal tissues. These cells may be rapidly expanded to large numbers ex vivo and then used for ACT. Alternatively, the TCR of such ligand-specific T cells can be cloned and expressed as TCR-transgenes in activated lymphocytes, using either recipient peripheral blood lymphocytes or activated T cell clones with defined specificities that grow well and do not have the capacity to attack normal host tissues.

Methods of using T cell populations for adoptive cell therapy in treatment of human subjects are known to those skilled in the art. T cell populations prepared according to the methods described herein can be used in such methods. For example, adoptive cell therapy using tumor-infiltrating lymphocytes, with MART-I antigen specific T cells have been tested in the clinic (Powell et al., Blood 105:241-250, 2005). Patients with renal cell carcinoma have been vaccinated with irradiated autologous tumor cells. Harvested cells were secondarily activated with anti-CD3 monoclonal antibody and IL-2, then readministered to the patients (Chang et al., J. Clinical Oncology 21:884-890, 2003.) In some embodiments, the present invention provides a method of preparing a T cell population for use in adoptive immunotherapy comprising T cells engineered to express an affinity maturated TCR, that recognize the target antigen; expanding these cells in culture; and reintroducing said cells back into the patient. (Hughes et al., Hum Gene Ther 16(4):457, 2005; Roszkowski et al., Cancer Res 65(4): 1570, 2005; Cooper et al., Blood 101: 1637, 2003; Alajez et al., Blood 105:4583, 2005). In one embodiment, the T cell population is autologous.

The term "cancer antigen" as used herein refers to any molecule (e.g., protein, peptide, lipid, carbohydrate, etc.) expressed by a tumor cell or cancer cell, such that the antigen is associated with the tumor or cancer. The cancer antigen can additionally be expressed by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor.

According to some embodiments, the cancer antigen is associated with an cancer selected from the group consisting of melanoma, non-Hodgkin's lymphoma, Hodgkin's disease, leukemia, plasmocytoma, sarcoma, glioma, thymoma, cancer of the thyroid, breast cancer, prostate cancer, colorectal cancer, kidney cancer, bladder cancer renal cell carcinoma, pancreatic cancer, esophageal cancer, brain cancer, pancreatic cancer, lung cancer, ovarian cancer, cervical cancer, multiple myeloma, hepatoma, acute lymphoblastic leukemia (ALL), acute myelogenous leukemia (AML), chronic myelogenous leukemia (CML), and chronic lymphocytic leukemia (CLL). In a preferred embodiment, the cancer antigen is a melanoma antigen.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "tumor-associated antigen" (TAA) refers to molecules that are associated with or detectably expressed by premalignant or malignant cells or cell populations. The tumor-associated antigen may also be expressed in certain normal cells or tissues during at least part of the normal cellular life cycle; however, the tumor-associated antigens as referred herein are expressed at higher levels in the tumor cells. In certain embodiments, the tumor-associated antigens are expressed at least from about 5 to about 100-folds higher in tumor cells relative to the levels in corresponding normal cells.

It will be appreciated that the subject may be treated by any other anti-cancer treatment (e.g. chemotherapy, radiation therapy, etc.) in combination with or prior to administration of the compositions of the invention.

According to additional embodiments, the T cells expressing affinity maturated TCRs and pharmaceutical composition comprising same, may be used for treating any other disease or disorder wherein the use of reactive T cells may be advantageous. For instance, the compositions of the present invention can be used for the treatment of bacterial, viral or parasitic infections, particularly chronic infections, by engineering and selecting TCRs that bind with a high affinity antigens associated with a bacteria, virus or parasite (e.g., from Epstein Barr virus, herpes virus, human immunodeficiency virus).

EXAMPLES

Materials and Methods

Plasmid Cloning

Plasmids were cloned by using New England Biolab restriction enzymes. Inserts were multiplied by PCR reactions from cDNA or from source plasmids. Restriction sites were added to the PCR primers in order to allow linking the insert segments to the target plasmids. Backbone plasmids, restriction endonuclease and primers that were used to clone the plasmids are described in Table 3.

Retroviral DNA Infection

Retroviral packaging of vectors was produced in Phoenix Ampho cells. Cells were co-transfected with packed vector, pCL-Ampho and Gag-Pol expression vectors. Medium containing packaging viruses were collected 48H and again 72H post transfection, filtered with 0.4 µM filters and kept at −80° C. Target cells were infected with packaging retroviruses in 2 cycles, in every cycle the cells were incubated for 12H with 1 ml of fresh medium and 1 ml of virus containing medium in the presence of 4 µg/ml of Polybrene. After 12H, the medium was replaced with fresh medium for an additional 12H of recovery.

RNA Electroporation

RNA electroporation was done using BTX electroporator, in 4 mm gap cuvette, 5 million cells suspended in 250 µl of Optimem (Gibco). Electroporation was done by a single pulse of 500 volts for 800 µs. Cells were immediately transferred into fresh and pre-wormed complete medium and seeded into culture dishes.

TABLE 3 backbone plasmids, restriction endonuclease and primers used for cloning the vectors

| Vector name | Backbone plasmid | Restriction site | | Insert source | | PCR primer used to amplify insert | SEQ ID NO: |
|---|---|---|---|---|---|---|---|
| pCDNA-AID | pCDNA3 | 5' | BamH I | Tet-AID vector | 5' | CGGGATCCATGGACA GCCTCTTGATG | 6 |
| | | 3' | Ecor I | | 3' | GCGAATTCTCAAAGT CCCAAAGTACG | 7 |
| pBABE-CD3 | pBABE-Puro | 5' | Ecor I | pMIGII-CD3δγεξ WT vector | 5' | CGGAATTCGCCAGGA TGGAACACAGC | 8 |
| | | 3' | Sal I | | 3' | ATGTCGACTTAGCGA GGGGCCAGGGT | 9 |
| pGEM4z-hAID | pGEM4z-eGFP | 5' | Xba I | Tet-AID vector | 5' | CGCGCTCTAGAATGG ACAGCCTCTTGATG | 10 |
| | | 3' | Not I | | 3' | ATAGTTTAGCGGCCG CTCAAAGTCCCAAAG TACG | 11 |
| pBABE-Pmel-TCR | pBABE-puro | 5' | BamH I | Pmel-TCR vector | 5' | CGGGATCCTAATACG ACTCACTATAGGGAT GAAATCCTTGAGTGTT | 12 |
| | | 3' | Sal I | | 3' | ACGCGTCGACTCATG AATTCTTTCTTTT | 13 |
| pET28-hAID | pET28b+ | 5' | Sal I | Tet-AID vector | 5' | CGGTCGACATGGACA GCCTCTTGATG | 14 |
| | | 3' | Xho I | | 3' | GCCTCGAGAAGTCCC AAAGTACG | 15 |

Tissue Culture

All cells were cultured with DMEM supplemented with 10% FCS, 1% L-Glutamine and 0.1% Gentamicin. For cells that were used in the Tetracycline expression system a Tetracycline-screened FCS was used.

Bacteria Culture

All cloned plasmids were transformed to a competent DH5a strain E. coli bacteria. Transformation was made by incubating the plasmids with the bacteria for 15 minutes on ice, incubating the bacteria at 42° C. for 2 min, 1 min on ice, addition of 1 ml LB, incubation at 37° C. with rotation for 1H, centrifuge for 5 min at 3000 g at room temperature, seed on LB-Agar plates supplemented with the appropriate antibiotics.

DNA Transfection

DNA transfections were done by using a BES method. In all transfections 10 µg DNA vectors were inserted into the transfection mix. Cells were incubated with the transfection mix for 6H and then the medium was replaced with fresh medium.

Western Blot Analysis

Western blot analysis was done according to standard protocols, antibodies used for the analysis are detailed in Table 4.

TABLE 4

List of used antibodies

| Antibody | Manufacture | Concentration used in 5% skim milk |
|---|---|---|
| Rabbit anti hAID | Abcam | 1/200 |
| Mouse anti GAPDH | Jackson ImmunoResearch | 1/1000 |
| Goat anti mouse-HRP conjugated | Jackson ImmunoResearch | 1/10000 |

TABLE 4-continued

List of used antibodies

| Antibody | Manufacture | Concentration used in 5% skim milk |
|---|---|---|
| Goat anti Rabbit-HRP conjugated | Jackson ImmunoResearch | 1/10000 |

FACS Analysis and Sorting

FACS analysis was done in a BD LSR II machine. Files were analyzed by FlowJo software. Cell staining was done according to standard protocols using commercial antibodies and according to the manufacture instructions. Staining antibodies are described in Table 5.

TABLE 5

List of antibodies used for FACS analysis

| Antibody | Manufacture |
|---|---|
| APC-anti CD3 epsilon | eBiosience |
| APC-anti mTCRβ | eBiosience |
| FITC-anti CD8 | eBiosience |
| PerCp-Cy5.5-anti CD4 | eBiosience |
| FITC-anti mTCR-Vβ13 | eBiosience |

Tetramer Staining

Monomers of H2D$^b$ mouse MHC class I molecules loaded with the human gp100 peptide KVPRNQDWL were ordered from the NIH tetramer facility. Monomers were conjugated to APC-Streptavidin (eBiosience) by incubation on ice. Cells were stained with tetramers for 1H in concentrations of 0.178 µg tetramers for 1 million cells in total volume of 50 µl of PBS supplemented with 0.5% BSA and 0.1% of Na-Azide.

Selecting Research Models

The work was performed on MHC class I peptides where the MHC groove is constrained on both ends and the TCR contact areas are better defined. The peptide we selected is the H-2D$^b$ restricted human gp100$_{25-33}$ (hgp100) immunodominant epitope, peptide (KVPRNQDWL; SEQ ID NO: 5) derived from B16 melanoma. The mouse homolog gp100/pmel-1$_{25-33}$ peptide differs in the first three amino acids (EGSRNQDWL; SEQ ID NO: 24). The hgp100 peptide has been shown to stabilize H-2D$^b$ at a 100-fold lower concentration than the mgp100 peptide and to be recognized by CD8$^+$ T cells at 1,000-fold lower concentration than the mgp100 peptide (Overwijk et al., 1998).

The T cell receptor a and R gene segment that recognizes the gp100 are the Pmel-TCR from Pmel-1 mice developed by Overwijk and his colleges in 2003 and were previously described in depth (Overwijk et al., 2003).

Example 1

Ex-Vivo Affinity Maturation System, Using Tet-Regulated Expression of AID, in 293TREx Cells In this affinity maturation system, 293TREx cells that stably express CD3 and the Pmel-TCR are created. In this system, controlled AID activity is induced by Tet-on induction.

Creating 293TREx Cells that Stably Express CD3

Figure 2:
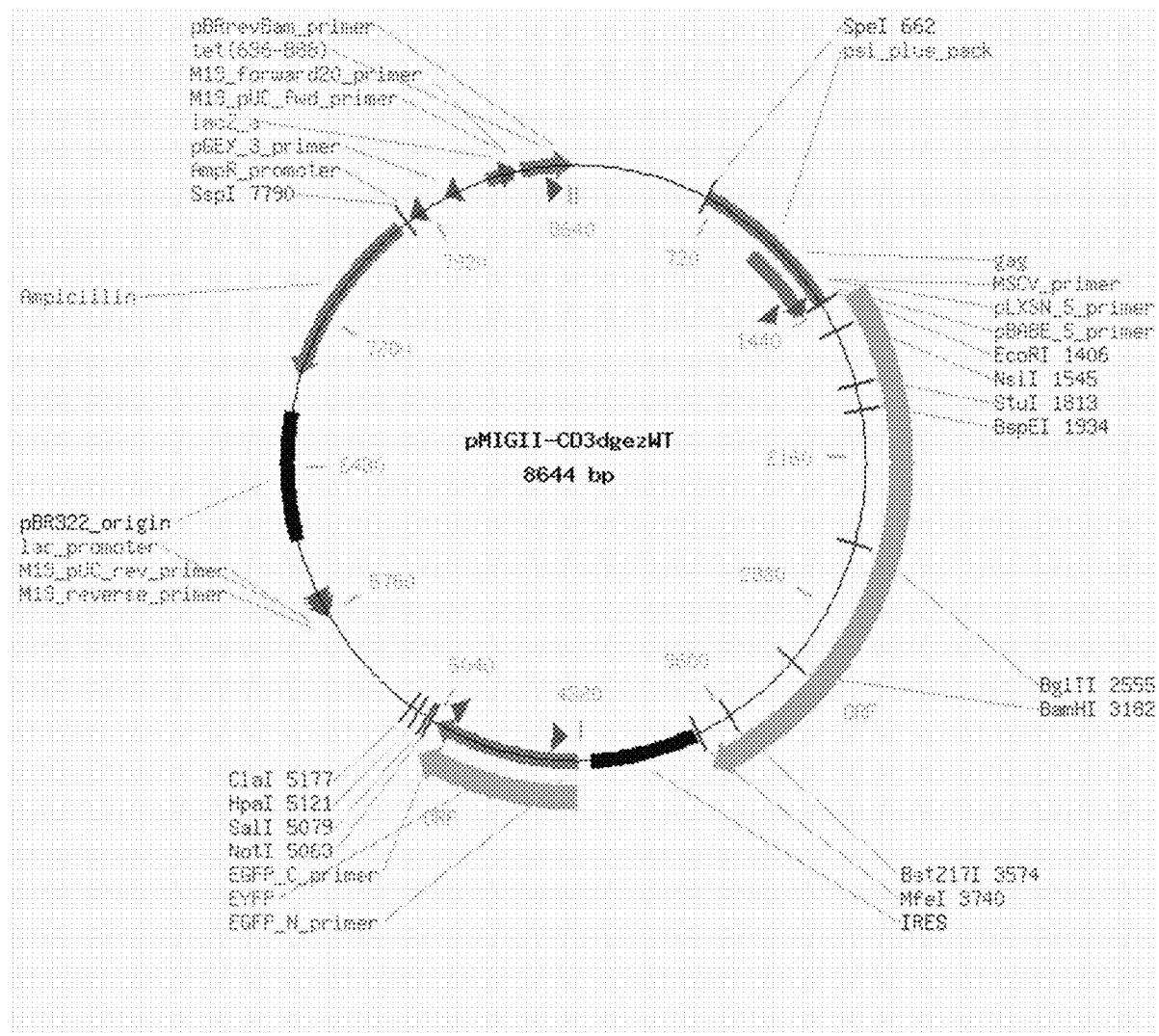
FIG. 2 depicts the pMIGII-CD3δγεξWT vector

In order to express the TCR on the cell surface of 293TREx cells it is essential to express the CD3 encore first. The CD3 encore is a complex of four different protein chains CD3δ, CD3γ, CD3ε and CD3ξ. An expression vector for all four CD3 chains as vector pMIGII-CD3δγεξWT was previously described (Szymczak et al., 2004). Briefly, the pMIGII-CD3δγεξWT contains one open reading frame for the expression of all four CD3δγεξ chains with F2A, T2A and P2A segments between the four chains respectively. A map of this vector can be seen in FIG. 2.

Figure 3:
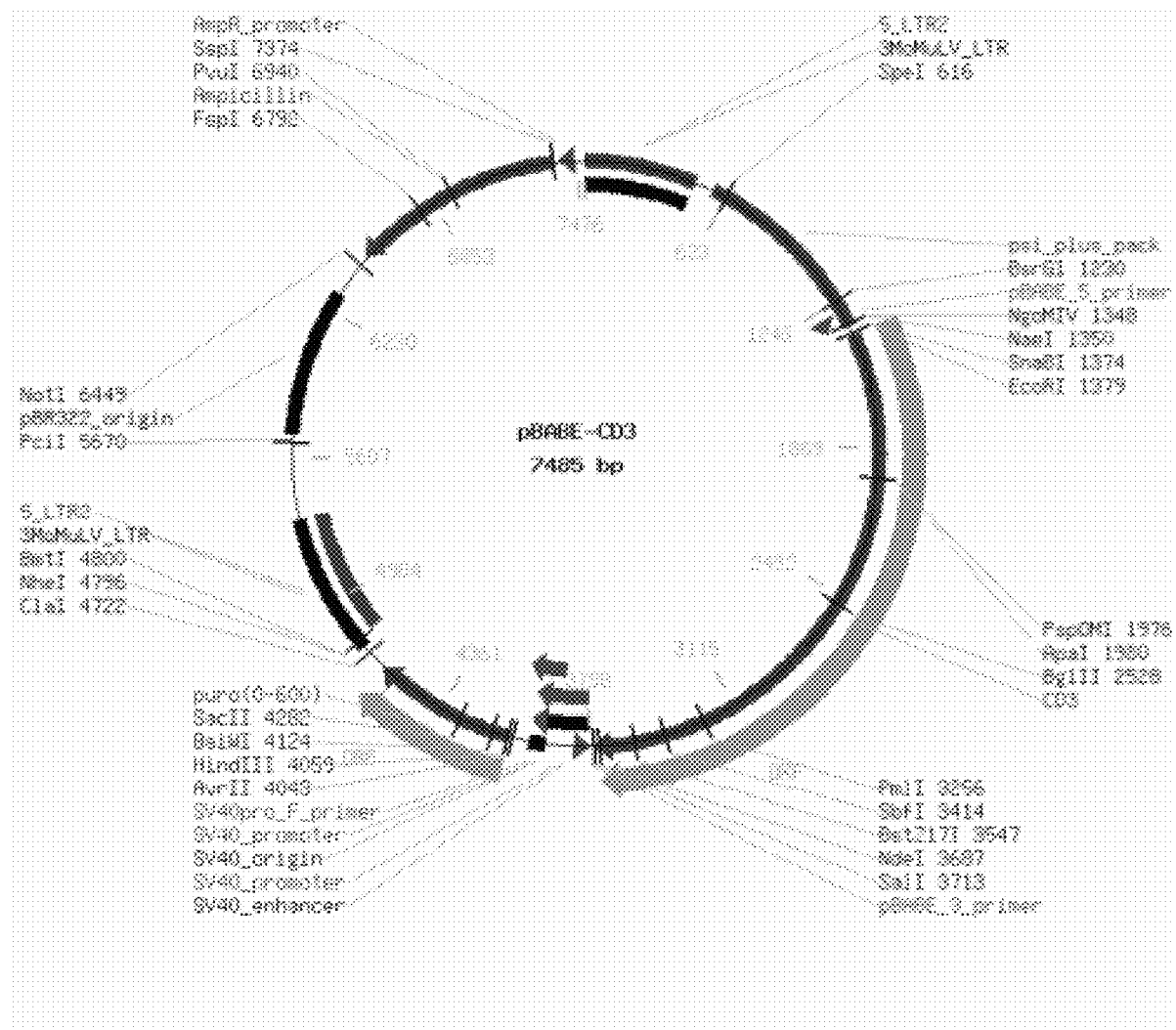
FIG. 3 depicts the pBABE-CD3 vector map.

The use of F2A, T2A and P2A segments in this vector creates a system allowing expression of all four CD3 chains at the same copy number. This system is based on the foot-and-mouth disease virus 2A peptide sequence and was previously described (Fang et al., 2005). This vector also contains a GFP expression segment but no antibiotic resistant gene for selection in mammalian cells. For this reason, the CD3 expression cassette was transferred to a pBABE-puro vector. As can be seen in FIG. 3, the pBABE-CD3 vector can be packed for retroviral infections and contains a Puromycin resistant segment.

After cloning, the pBABE-puro-CD3 vector was packaged into retroviruses by transfecting the plasmids into Phoenix Ampho cells and collecting the viruses 48H and 72H post transfection. 293TREx cells were infected with these viruses in two cycles and in the presence of Polybrene. 48H post infection Puromycin was added to the cells and selection was done by culturing the cells with Puromycin for two weeks. After selection, limiting dilutions of the cells were performed in 96 well plates in order to isolate separate single cell colonies. The colonies were later checked for CD3 expression by western blot analysis with a specific antibody against CD3ε. As can be seen in FIG. 4, some of the cell lines express high levels of CD3ε while other cell lines do not. Two cell lines were chosen to continue this work, line number 7 and line number 8. The CD3 complex is stabilized and presented on the cell membrane only if the TCR is expressed. For this reason, the presence of the CD3 on the cell membrane by FACS could not be verified before expressing the TCR.

Creating 293TREx-CD3 Cell Lines that Stably Express Pmel-TCR

After succeeding in creating the CD3 expressing 293TREx cell lines, the next step was to transfect these cells with Pmel-TCR expression vector. The Pmel-TCR expression vector was previously cloned in the inventors' lab. Briefly, the Pmel-TCR vector is a plasmid containing both expression segments of Pmel-TCRα and TCRβ chains. The two chains are linked with a F2A segment in order to allow the TCRα and TCRs segments to be expressed in the same copy number. In addition to the TCRα-F2A-TCRβ expression segment, the Pmel-TCR expression vector contains an EGFP expression segment and a Neomycin resistant segment for selection in mammalian cells. A map of this expression vector can be seen in FIG. 5.

Two 293TREx-CD3 cell lines (number 7 and 8) were transfected with the Pmel-TCR vector using BES method. 48H post transfection the cell lines were selected for positive transfected cells by double selection of Puromycin and G418 resistance. After two weeks of selection, the cells were observed by florescence microscopy, checked for EGFP expression and analyzed by FACS for CD3 expression after staining with relevant antibodies. As can be seen in FIGS. 6A and 6B, 293TREx cells do not present CD3 on their cell membrane. 293TREx-CD3 also have no CD3 present on their cell membrane. Even though these cells were transfected with pBABE-CD3 and exhibited expression of the CD3 protein chains (as was established by western blot), the CD3 is not presented on the cell membrane until TCR is co-expressed. On the other hand, the 293TREx-CD3-Pmel-TCR cells (lines 7 and 8) express the CD3 complex nicely assembled and stabilized on the cell membrane. The statistics for double positive cells was 38.5% in line 7 and 43.5% in line 8. Further work was continued with cell line number 8, due to a higher double positive percentage of cells and the fact that in line 8 there is a better segregation between different groups, making this line suitable for FACS sorting.

In addition to the FACS analysis, some of the 293TREx-CD3-Pmel-TCR stained cells were collected, fixed and subsequently observed by confocal microscopy in order to detect the CD3-TCR complexes. As can be seen in FIG. 7 the complexes are evident on the cell surface (circled in FIG. 7).

FACS Sorting of 293TREx-CD3-Pmel-TCR Cells

From the FACS analysis, it seems that in 30-40 percent of cells both CD3 and Pmel-TCR are expressed, folded and assembled correctly on the cell surface. Cells were further sorted by FACS-sorting in order to have a homogeneous and well assembled CD3+ TCR cell line. The cells were sorted using FACSaria after staining with CD3 antibody and collecting only double positive, $CD3^+$ and $GFP^+$ cells.

Tetramer Staining of 293TREx-CD3-Pmel-TCR Sorted Cells

After testing the expression and presence of the CD3-TCR complex on the cell surface it is essential to determine the capability of the TCR to bind the MHC-class I molecule presenting the gp100 peptide. In order to test binding capability of the TCR a tetramer staining assay was performed. The tetramer staining assay is designed for testing TCR-MHC binding and was previously described (Ogg and McMichael, 1998). Briefly, the tetramer is a complex of four monomers. Each monomer formed from a mouse MHC-class I molecule, $H-2D^b$, presenting the human gp100 peptide KVPRNQDWL. The $H-2D^b$ molecule is conjugated to a biotin molecule. The tetramers are assembled by linking four biotin conjugated monomers to one molecule of APC-conjugated Streptavidin. The 293TREx-CD3-Pmel-TCR cells were stained with the tetramers and analyzed by FACS.

As can be seen in FIGS. 8A and 8B, 293TREx cells do not stain with the tetramers, nor do 293TREx-CD3 cells. However, the majority (81.5%) of 293TREx-CD3-Pmel-TCR are stained with the tetramers. These findings indicate that the 293TREx-CD3-Pmel-TCR cells present a well folded T cell receptor that is able to bind a specific MHC-peptide and that the FACS sorting improved the percentage of double positive cells in this cell line.

Stable Transfection of 293TREx-CD3-Pmel-TCR Cells with Tet-AID Vector

In order to induce and control AID expression in the 293TREx-CD3-Pmel-TCR cells, cells were stably transfected with the Tet-AID vector. The Tet-AID expression vector was cloned previously in the inventor's lab. Briefly, the Tet-AID vector was constructed by cloning the human AID gene, downstream of two Tetracycline Repressor Elements (TRE) in the pCDNA4/TO/myc-His-C plasmid. The 293TREx cell line is a commercial cell line that stably expresses the pCDNA6/TR expression vector, this means there is a permanent expression of Tet Repressor (TR) in these cells. After transfection of the Tet-AID vector to the 293TREx cell line, in the absence of Tetracycline, the TR protein binds the TRE on the Tet-AID vector and represses AID expression. Once Tetracycline (or analog Doxycycline) is added to the culture medium, the Tetracycline binds the TR protein and the TR-TRE bond is dismantled, allowing the AID gene to be expressed. In the Tet-AID vector, in addition to the TRE elements and the AID gene, there is a Zeocin resistance segment for selection of positive transfected cells. A map of Tet-AID vector can be seen in FIG. 9.

48H after the transfection of 293TREx-CD3-Pmel-TCR cells with the Tet-AID vector the cells were selected with Zeocin for two weeks. After selection, single cell colonies were established by limiting dilutions seeding 0.5 cells per well in 96 well plates. After colony establishment, 22 colonies were checked for correct expression of AID after Doxycycline induction by adding 10 μg/ml of Doxycycline to the medium and protein analysis by western blot 24H post induction.

As can be seen in FIG. 10, AID expression is repressed and in most of the cell lines and it is induced upon addition of Doxycycline. The well induced cell lines are lines number 1, 2, 3, 4, 5, 6, 7, 9, 10, 11, 12, 13, 14, 15, 16, 17, 18, 19, 20 and 24. The selected 293TREx-CD3-Pmel-TCR cell lines express all 4 constructs, CD3, Pmel-TCR, Tet repressor and Tet-AID and therefore are positive for all 4 selection antibiotics, Puromycine, G418, Blasticidine and Zeocyne. These cell lines were denoted 4P.x cells (4P=4 positive, x=line number).

Tetramer Staining of 4P Cell Lines

After verifying AID induction by Doxycycline in the various cell lines, the next step was to check the different cell lines for Tetramer staining in order to choose with which of the cell lines to continue. 1 M cells from each cell line were stained by tetramers and analyzed by FACS. As can be seen in FIG. 11, lines number 2, 4, 6, 9, 10, 11, 14, 17, 18 and 19 are properly stained with tetramers whereas other lines were stained poorly.

Tetramer Staining of 4P Cell Lines after AID Induction

The properly stained cell lines were farther analyzed for changing their tetramer staining pattern after AID induction by Doxycycline. The different cell lines were induced by 1 sg/ml of Doxycycline for 72H and then 1 M cells from each cell line were stained by tetramers and analyzed by FACS. As can be seen in FIG. 18, in lines number 11, 14, 17 and 10 a slight change toward the high tetramer stained can be detected after AID induction, whereas in lines 2, 4, 6 and 9 a slight change toward the low tetramer stained can be detected. In lines 16 and 18 no change was detected.

AID Induction and FACS Sorting of Tetramer Stained 4P Cells to Single High Affinity Colonies Because 4P.10 and 4P.17 cell lines displayed the most significant change toward high tetramer stained cells after AID induction, the study was initially continued with these cell lines first. AID was induced in the 4P.10 and 4P.17 cells by addition of 1 μg/ml Doxycycline to the growth medium, 72H post induction the cells were stained by tetramers and sorted by FACS. High tetramer stained cells were collected into 96 well plates, single cell per well. Gating and sorting parameters can be seen in FIG. 13.

After sorting, the single cell colonies were continuously cultured and expanded into bigger wells. The colonies that survived the expansion were named 4P.10.x and 4P.17.x. after expansion the different colonies were tested by tetramer staining and FACS analysis. As can be seen in FIG. 14, several 4P.17 colonies were indeed stained higher by tetramers than the basic 4P.17 cell line, For example lines 4P.17.3 and 4P.17.4. On the other hand some of the lines seem to have lower tetramer staining than the basic 4P.17 cell line, like 4P.17.1 and 4P.17.2.

The differences in tetramer staining may reflect differences in TCR affinity between the cell lines but it might reflect differences in the TCR expression level between the cell lines too. To address this question, the cell lines were tested in two different staining modes, (i) tetramer staining and (ii) use of an antibody that stains directly the TCRβ chain. The TCRβ staining reflects the TCR expression level of the cells and therefore the TCRβ staining data is used for normalizing the tetramer staining data thus teaching different affinities of the cells. Affinity was calculated as the division of the tetramer staining mean in the TCRβ staining mean, as can be seen in the next equation:

$$\text{affinity} = \frac{\text{tetramer staining mean}}{\text{TCR}\beta \text{ staining mean}}$$

In order to test this reference and to check the affinities of the different sorted cell lines, a FACS analysis was done after staining the cells differently with tetramers or with TCRβ antibody. As can be seen in FIGS. 15A-15D, there is a strong correlation between tetramer staining and TCRβ staining in most of the cell lines. This result suggests that most of the change in tetramer staining is actually due to changes in TCR expression levels and not in TCR affinity. However when looking at the results of the tetramer staining mean divided in the TCRβ staining mean (refer to as affinity) it seems that for some of the cell lines there is a change in the TCR affinity to some instance, for example in the case of 4P.10.2, 4P.10.3, 4P.10.6 and 4P.17.4.

5 Cycle Enrichment Sorting for High Affinity 4P Cells after AID Induction

The following approach was used in order to collect the high affinity cells together by sorting them together into a single well. AID was induced in 4P.17 cells by adding Dox to the medium and 72H after induction the cells was stained by tetramers (conjugated by APC) and TCR antibody (conjugated by PerCp-Cy5.5. The cells were sorted according to the following conditions (as can be seen in FIG. 16): First gating is for main size cells, to avoid collecting large or small size cells or even dual or triple cells together. Second gating is for GFP positive cells, in order to avoid collecting cells that lose the TCR expressing vector. The third gating is for medium to low TCR staining, this gating step is in order to avoid collecting cells that stain highly by tetramers due to high TCR expression level and not due to high affinity. The last gating is for high tetramer stained cells, this cells are collected together into single well in 96 well plate. By use of the five gating steps described above, cells that stain highly with tetramers while having low TCR expression level were collected. These cells can be referred as high affinity cells.

These cells were further cultured and expanded. After expansion the cells were induced by Dox and a second sorting cycle was carried out. The gating for this second cycle was identical to the first cycle, and so on for 3 more cycles (total of 5 sorting cycles). In every cycle a protein samples were taken and AID induction was verified by western blot as can be seen in FIG. 17B. In this way, the high affinity cell fraction was enriched. The sorted cells were named according to the enrichment cycle, 4P.17 HAf cy1, 2, 3, 4 and 5 (4P.17-High Affinity, cycle 1, 2, 3, 4, and 5). As can be seen in FIG. 17A, when comparing the tetramer/TCR staining of the cells from the different sorting cycles to that of the original 4P.17 cell line, it seems like there is an affinity maturation of the cells between the different sorting cycles.

After the 5 enrichment cycles, a limiting dilution procedure was done in order to obtain single cell colonies for sequencing the TCR segments in the cells. These colonies were expanded and tested again by tetramer and TCR staining and analyzed by FACS. As can be seen in FIG. 18, most of the colonies exhibited high affinity character compared to the basic 4P.17 cell line.

After analysis, RNA was extracted from the different 4P.17 HAf Cy5 cell lines. First strand cDNA was synthesized by RT and the TCR segments were amplified by PCR using specific primers. The amplified TCR from the different cell lines was sent for sequencing and the sequencing results were aligned to the original TCR sequence. To However, no mutations were discovered in this alignment too.

It is obvious that the AID protein is expressed in the cells after induction by Dox as can be seen in FIG. 17B. The AID protein expressed in the cells seems to be active and capable to mutate plasmid DNA as shown in table 6.

A series of sorting experiments was launched to find out what are the finest conditions for sorting the cells in order to increase their survival even when sorted in low numbers into separate wells. In these experiments several different sorting parameters were tested as well as different feeders in several concentrations. Thereafter, it was discovered that the best options for sorting the cells is by using very low speed sorting, achieved by enlarging the sorting nasal to maximum, and using 293TREx cells as feeders. After sorting the cells into wells with 293TREx cells and letting them to expand for several days, the 4 selecting antibiotics that the 4P cells are resistant to (but not the 293TREx cells) are added thereby enabling only the 4P cells to expand in the presence of the selection.

AID induction period in these experiments was relatively short (72H before staining and sorting). Short induction time means decreasing the chances of AID to target the TCR segments and to mutate it. In addition to that, in this short period the mutated cell replicates less than 3 times, which means low number of cells for each random mutation and low chances to detect the mutations. Thus, another experiment series was performed with longer periods of AID induction.

Long Induction of AID and Sorting of High Affinity Cells

In this experiment AID was induced by adding Dox to the culture medium and sorting of high affinity cells after long induction periods spreading from one week to approximately two months. The cells were kept in Dox containing medium for all the experiment, and were split every 4 days by using Dox containing medium. Every week, 10 million induced cells were taken for staining with tetramers and TCR antibody and relatively high tetramer/low TCR cells were sorted into 96 plate containing 293TREx cells as feeders. The high affinity cells were sorted as 4-5 cells per well in order to increase survival chances. In this way the inventors managed to get enough colonies and preserve the ability to see a mutation in some of the cells. 3 days after sorting, the cutler medium was replaced to a selection medium containing all 4 selection antibiotics that the 4P cell lines are resistant for, and the 4P cells were selected in this medium. This procedure has been done for three of the 4P cell lines, 4P.2, 4P.11 and 4P.17. During the experiment, the induction of AID was verified by western blot analysis of cell extracts and the verification can be seen in FIG. 19.

The gating steps for sorting the cells in this experiment can be seen in FIG. 20. First gating step is for main size cells, to avoid collecting large or small size cells or dual or triple cells together. Second gating step is for GFP positive and TCR staining positive cells, in order to avoid collecting cells that lost the TCR expressing vector or the ability to present the TCR on the cell surface. The third gating step is for relatively high tetramer staining while low TCR staining cells, the upper left corner of the tetramer vs. TCR graph. These are the cells that were collected.

The same gating steps and sorting were taken weekly for 7 weeks. During the induction period there was a slight increase in the percentage of the high affinity cells in line 4P.11 and especially in line 4P.2, less in line 4P.17 as can be seen in FIG. 21 A-E representing the change in cells affinity after some of the induction periods (FIG. 21A, 21B, 21 C, 21D or 21E exemplifies week 2, 3, 5, 6, or 7, respectively).

After selection of the high affinity cells with the selection media, the different cells that were sorted from the 6th' and 7th' week formed 165 different colonies. Culturing these colonies continued to receive expansion to high cell numbers. After expansion, 1 million cells from every colony were stained by tetramers and TCR antibody and the affinity level of the TCR was analyzed by FACS. Some of the colonies indeed increased their TCR affinity comparing to the original 4P cell line, as can be seen for example for some of the 4P.17 sorted lines in FIG. 22A-22C. while in other cell line it seems that there was no improvement or even a slight decrease in TCR affinity, as can be seen for example for some of the 4P.11 sorted lines in FIG. 22D-22E.

In parallel to the FACS analysis of the different colonies, RNA was extracted from the colonies. First strand cDNA was synthetized using oligo dT primers and a PCR reaction with primers specific for the TCR segment was conducted in order to amplify the TCR segment. In the PCR reaction a high fidelity PFU polymerase was used in order to avoid introducing mutations in this step. Some of the samples were run on Agarose gel in order to confirm the TCR amplification and the amplification results can be seen in FIG. 23.

After amplification, the PCR samples were treated with ExoSAP-IT reagent (manufactured by USB-Affymetrix, Cleveland, Ohio, USA) in order to get rid of any primers or dNTPs left from the PCR reaction and the samples were sent for sequencing using primers specific for sequencing the variable regions of the Pmel-TCR α or β chains.

At the first step, TCR α and β segments from 31 different colonies were sequenced. A total of 8 different mutations in 7 out of the 31 cell lines were observed. A summary of the mutation found can be seen in table 6.

Due to the fact that the cells were sorted 4-5 cells per well, meaning the cell lines are not pure single cell colonies, the mutations are present only in part of the cells in each cell line. That can be seen when examining the sequencing chromatographs as can be seen in FIG. 24.

Colony PCR Sequencing

In order to be able to check for mutation directly after sorting a colony PCR sequencing procedure is performed. In this experiment, high affinity cells are sorted directly into 96 well PCR plate. The cells are sorted as single cell per well or up to 7 cells per well. The cells are lysed in the wells by a lysis buffer containing Proteinase K and SDS. The lysis is performed by incubating the cells in the buffer at 50° C. for 1H followed by 30 minutes incubation in 99° C. for DNA denaturation. After lysis, a PCR mixture, containing PFU polymerase and primers specific for the TCR segment is added to the lysed cells and the TCR segment is amplified by 35 cycles of PCR reaction. After this first PCR reaction, 2 μl of each amplified DNA sample is added to a new plate containing new PCR mixture (same mixture as for the first PCR reaction) and a second PCR reaction is performed. After these two PCR reactions a sample of each well is separated on Agarose gel and the wells that contained band at the appropriate size for the TCR segment (≈1700 bp) are sequenced.

Example 2

Ex-Vivo Affinity Maturation System Using Controlled Expression of AID by mRNA Electroporation In this system, control of AID expression is achieved by inducing AID expression in the cells through AID-mRNA electroporesis. The mRNA will be electroporeted into the TCR expressing cells. Once in the cell, the mRNA will be translated into the AID protein. Because the mRNA has a relatively short half-life, after several translation cycles, it will disintegrate in the cell. This allows for temporary expression of AID in the cells. After AID induction, the TCR improved cells will be collected by FACS sorting after tetramer staining, cultured and mutations in the TCR will be analyzed by DNA sequencing.

TABLE 6

8 mutations found at 7 out of 31 lines sequenced at the first step of sequencing the different colonies

| Line | Sequencing sample | TCR alpha mutation | TCR beta mutation | Mutation classification | Codon change | Effect on protein |
|---|---|---|---|---|---|---|
| 4.17.160 | B5a | 14 bases deletion from G238 to G341 | | Deletion + frame shift | Bases 460-463 = TGA | Stop translation of TCR alpha after 153 amino acids and not TCR beta translation |
| 6.17.G11 | G1a | G388A | | transition | GCA >> ACA | Ala >> Thr |
| 6.2.F12 | A2 | C413G | | transversion | GCT >> GGT | Ala >> Gly |
| 6.17.G6 | A9 | A398G | | transition | CAG >> CGG | Gln >> Arg |
| 7.11.F5 | B12 | | C600T | transition | AGC >> AGT | Silent mutation (Ser in both) |
| 6.2.E12 | B14 | | G548C | transversion | GTA >> CTA | Gly >> Ala |
| 7.2.D7 | B20 | | G49C | transversion | GCA >> GTA | Val >> Leu |
| 7.2.D7 | B20 | | C797T | transition | | Ala >> Val |

In-Vitro Expression of hAID-mRNA

In order to electoporete the AID-mRNA into the 293TREx-CD3-Pmel-TCR cells, the AID-mRNA needs to be expresses in an in-vitro system. The hAID gene was cloned into a pGEM4z vector, downstream of T7 promoter, to create the pGEM4z-hAID vector. A map of the pGEM4z-hAID vector can be seen in FIG. 26.

The pGEM4z-hAID vector was expressed in-vitro by using the commercial in-vitro expression system from Epicentr biotechnologies according to the manufacturer protocol. AID mRNA transcription was verified by RT-PCR. As can be seen in FIG. 27, AID-mRNA was successfully transcribed in-vitro.

Validation of hAID-mRNA Translation by Electroporation into 293HEK and 293TREx Cells To test translation of in-vitro expressed hAID-mRNA in live cells, AID-mRNA was electroporated into 293HEK and 293TREx cells. 18H post electroporation, proteins were extracted and analyzed for presence of the AID protein, by Western blot. As can be seen in FIG. 28, AID protein was detected in both 293HEK and 293TREx cells that were electroporeted with AID-mRNA, but not in cells that were electroporeted with no mRNA.

Electroporation of AID-mRNA into 293TREx-CD3-Pmel-TCR Cells

After AID-mRNA electroporation to 293TREx-CD3-Pmel-TCR cells, the cells are stained with tetramers, sorted for cells with improved TCRs and mutated-analyzed. Before staining, cells must be checked for the presence of the AID protein. A time course experiment was created in order to determine the AID translation pattern in the cells. 293TREx-CD3-Pmel-TCR cells were electroporeted with AID-mRNA and tested for AID protein levels at several time points post electroporation. As can be seen in FIG. 29, AID levels are already high five hours after electroporation and remain high for more than 24 hours. 48H after electroporation there is no detectable AID protein in the cells.

AID mRNA Electroporation and Calibration of Tetramer Staining

After determining the time scale for AID expression and degradation after AID mRNA electroporation in 293TREx-CD3-Pmel-TCR cells, changes in tetramer staining of these cells were evaluated. 5 million 293TREx-CD3-Pmel-TCR cells were electroporeted with or without 5 µg of AID mRNA, 72H after electroporation the cells were stained with several decimal dilutions of tetramers starting with 0.178 µg tetramers for 1 million cells. The cells were then analyzed by FACS. As can be seen in FIG. 30, upon electroporation of AID mRNA there is an increase in the proportion of positively tetramer stained cells, among the medium-low Pmel-TCR expressing cells. The cells are stained properly only with the 0.178 µg tetramers per 1M cells and a change in tetramer staining upon AID electroporation can be detected only in this staining concentration.

AID mRNA Electroporation and Sorting of High Affinity Cells

After calibrating the tetramer staining, an experiment was conducted in which 293TREx-CD3-Pmel-TCR cells were electroporated with AID mRNA and 72H post electroporation, the cells were stained with tetramers and TCR antibody. After staining, the cells were sorted by FACS. Gating steps for this sorting can be seen in FIG. 31. The first gating step is for main size cells, to avoid collecting large or small size cells or dual or triple cells together. Second gating step is for medium to low TCR stained cells, this gating step is in order to avoid collecting cells that stain highly by tetramers due to high TCR expression level and not due to high affinity. The last gating is for high tetramer stained cells. These cells were collected.

This procedure was done several times. At the initial attempts the cells were sorted as single cells into 96 well plates containing enriched medium. At the next attempts the high affinity cells were sorted as single cells into 96 well plates containing 10,000 to 150,000 irradiated PBMCs per well as feeders. Some of the attempts were done in several different time points after electroporation, for example 72H and 96H after electroporation. In all the experiments a slight increase in tetramer staining upon AID mRNA electroporation is detected as can be seen for example in FIG. 32.

No single cell colonies survived from these experiments, so no TCR sequencing could be analyzed. Thus, high affinity cells were collected together to one well and cultured collectively. AID mRNA was electroporeted and the cells were stained as described before. High affinity cells (shown in FIG. 33) were sorted together into a single well and cultured for few days to let the cell expand to higher numbers. These cells were named 293TREx-CD3-Pmel-TCR-HAf Cy1 (high affinity, cycle 1).

After expansion, the cells were electroporeted again with AID mRNA and 72H after the electroporation the cells were stained with tetramers and TCR antibody and taken for a second sorting cycle. To our surprise, the electroporeted cells seemed to lose the TCR expression as can be seen in FIG. 34. This phenomenon of losing TCR expression after 2 cycles of AID mRNA electroporation repeated again in two more experiments. Loss of TCR expression may be a result of a nonsense mutation in the TCR sequence.

Example 3

In-Vitro Affinity Maturation System Using AID and Cell Extracts

In this affinity maturation system, AID is used in-vitro, in order to mutate Pmel-TCR on plasmids. The reaction is carried out in tubes containing the plasmid, recombinant AID, Ramos cells extract, T7 RNA polymerase, nucleotides and buffers that maintain appropriate reaction conditions. Previous studies showed that transcription is essential for AID activity in-vitro (Bachl et al., 2001; Besmer et al., 2006; Shen et al., 2009) for this reason transcription needs to be induced in the mutation reaction. In order to be able to induce transcription of the TCR genes, the TCR expression segment was cloned downstream of T7 promoter. The T7 RNA polymerase and nucleotides in the reaction mix will induce AID transcription during the mutation reaction. After AID deaminates the Cytidine to Uridine, Uracil DNA Glycosylase (UNG) and DNA repair mechanisms will turn Uridine to Guanine/Adenine or Thymidine. The repair mechanisms involved in the process are the Base Excision Repair (BER) system and the Mismatch Repair (MMR) system. To mimic the involvement of these repair systems in the mutating process, it is essential to include the relevant enzymes in the in-vitro mutation reactions. By adding a nuclear extract from cells capable of the SHM process we can be sure that all the enzymes needed for the process are in the reaction mixture. The Ramos cell line is a B cell lymphoma that expresses high amounts of the AID protein and it is constantly in a SHM process, therefore Ramos extract was used in the reaction mixture. The repair mechanism enzymes are nuclear and the AID protein is usually cytoplasmatic and only locates to the nuclear when activated. For this reason, both cytoplasm and nuclear fractions were added to the reaction mixture. After the mutation reaction, the plasmids are transformed into bacteria, cultured, extracted from bacteria, packed into retroviruses, infected into CD3 expressing cells and analyzed by tetramer staining and FACS.

Constructing a pBABE-T7-Pmel-TCR Vector

In order to package the mutated plasmids in retroviruses the Pmel-TCR expression cassette needs to be initially transferred into a retroviral vector. In addition, in order to allow AID mediated mutation of the plasmid, transcription of the vector needs to be activated. For this, a T7 promoter should be inserted before the Pmel-TCR expression segment. For these reasons the pBABE-Pmel-TCR vector was cloned. As can be seen in FIG. 35, there is a T7 promoter before the Pmel-TCR segment in a pBABE-T7-Pmel-TCR expression vector. The pBABE vector contains a Puromycin resistance segment.

Sequence Analysis of pBABE-T7-Pmel-TCR Vector for SHM Enhancing

Motif Previous studies showed that the cis-element CAGGTG in the context of Ig enhancers is sufficient to target SHM to a nearby transcribed gene (Michael et al., 2003; Storb et al., 2007; Tanaka et al., 2010). The CAGGTG motif binds E47 in nuclear extracts of the mutating cells. Replacing CAGGTG with AAGGTG in the construct without any other E47 binding site eliminates SHM. The CA versus AA effect requires AID. CAGGTG does not enhance transcription, chromatin acetylation, or overall target gene activity. In order to check for a CAGGTG sequence in the pBABE-T7-Pmel-TCR vector, the vector sequence was scanned using Fuzznuc software. As can be seen in FIG. 36, the CAGGTG motif was found in six places on the plasmid, three times on the sense strand and three times on the anti sense strand.

In-Vitro AID Activity Assay

Initially the Ramos cell extracts were considered as an exclusive source for all enzymes for the in-vitro affinity maturation system reaction. Meaning that, the AID protein and all the repair mechanisms enzymes will be exclusively from the Ramos extracts. In order to test the ability of the Ramos extracts to mutate the TCR vector we designed an in-vitro AID activity assay. In this assay, a reporter plasmid named pKMP2 was used. The plasmid was a gift from Ursula Storb and was previously described (Shen et al., 2009). Briefly, the pKMP2 plasmid contains two open reading frames that code for antibiotic resistance. One reading frame for Ampicillin resistance and the other for Kanamycin resistance. The start codon ATG at the 5' of the Amp resistance segment is mutated to ACG while the Kan resistance segment is intact. The ACG start codon of the Amp resistance is in the context of an AID "hot-spot", WRCY. In addition to the resistant segments, the pKMP2 vector contains a T7 promoter up-stream to the Amp resistance gene in order to allow transcription activation in the assay. When incubated with AID, if the AID interacts and is activate on the ACG site, the C will be deaminated and become U. After deamination, if the mutated vector is transformed into bacteria and the U has not be replaced by a different nucleotide, it will be recognized by bacterial transcription and replication machineries as a T and the transformed bacteria will gain resistance to Amp. To make sure that the deaminated U is not been removed or replaced by different nucleotides, the vectors are transformed into UNG deficient bacteria. In order to test the Ramos extracts a pKMP2 vector was incubated with Ramos cytoplasm, nuclear or whole cell extracts, in the presence of T7 RNA polymerase. 293HEK whole cell extract was used as control.

After incubating the plasmids with the different extracts, the plasmids were precipitated and transformed into BW504 UNG deficient a E. coli strain. The BW504 bacteria were a generous gift from Ashok Bhagwat. After the transformation, the same amounts of bacteria were seeded on Kan and Amp plates (half of the transformation mixture was seeded on a Kan plate and the other half on an Amp plate). As can be seen in Table 1, the results are problematic. Samples that contain cytoplasm extract have no or very few colonies on the Kan plate. A repeat of the reaction gives similar results. This could be due to the presence of DNAse in the cytoplasm of 293HEK and Ramos cells. The 15 colonies that grow on the Amp plate from the pKMP2 vector sample are probably a result of spontaneous mutations of the ACG to ATG although no verification was made.

TABLE 1

Number of transformed colonies that grew on Kan or Amp plates

| Incubation mixture | Approximate number of colonies grown on Kanamycin plates | Approximate number of colonies grown on Ampicillin plates |
|---|---|---|
| pKMP2 vector alone | 1000 | 15 |
| pKMP2 + 293HEK extracts | 0 | 0 |
| pKMP2 + Ramos whole cell extract | 20 | 0 |
| pKMP2 + Ramos cytoplasm extract | 0 | 0 |
| pKMP2 + Ramos nuclear extract | 500 | 1 |
| pKMP2 + Ramos cytoplasm extract + Ramos nuclear extract | 0 | 0 |

To overcome the DNAse problem DNAse inhibitors were sought. There are no commercial DNAse inhibitors but there are a few molecules that were shown to relatively inhibit DNAse activity. Aurintricarboxylic acid was shown to inhibit DNAse but could not be used in this assay because it works by disrupting enzyme-DNA access and might also disrupt transcription and AID activity in the reaction. G-Actin and $ZnCl_2$ were also shown to inhibit DNAse activity (Lazarides and Lindberg, 1974). Unfortunately, a repeat experiment with several concentrations of G-Actin and/or $ZnCl_2$, resulted similarly.

Producing Recombinant AID

Because loss of the plasmid seems to occur when adding the cytoplasmatic fraction, ways of avoiding this fraction were investigated. The problem is that most of the AID protein in Ramos cells is cytoplasmatic. Work was continued with the nuclear fraction and recombinant AID was added. The hAID gene was cloned into a pET28b+ vector with two six-His tags, one at the amine terminus of the AID protein and the other at its carboxyl terminus. The pET28 system is designed for expression of recombinant proteins in bacteria. The induction of protein production is done by adding IPTG to the growth media. The vector was named pET28-hAID as can be seen in FIG. 37.

Purification of Recombinant AID

The pET28-hAID vector, was transformed into Rosetta strain E. coli bacteria. The rosette strain is an E. coli strain with some genetic changes that make it suitable for producing recombinant proteins. Recombinant AID protein was produced by culturing high quantity of the transformed bacteria in the presence of IPTG. After IPTG induction the bacteria was harvested and the AID-tagged protein was purified according to standard protocols using TALON metal affinity resin, beads that bind specifically to the 6-His tag on the recombinant protein. Several attempts to produce and purify the protein were done in order to calibrate culturing temperatures, IPTG concentration, induction time and other parameters. At the first attempts most of the produced protein wasn't purified well, as can be seen in FIG. 38A, probably because of over production of the recombinant protein in the bacteria what caused it to aggregate and to form complexes of the protein with other unknown proteins in the bacteria. But after calibrating the IPTG concentration and lowering the culturing temperatures, as can be seen in FIG. 38B, the purification of the recombinant protein was improved, as can be seen in FIG. 38C.

Coomassie staining of SDS-PAGE resolution of the eluted recombinant AID, reviled that the elution is not completely pure, and there are some other un-specific proteins in the sample (FIG. 39).

Since the eluted recombinant protein was not completely pure, the inventors decided to purify the protein with FPLC. The eluted sample was loaded on superdex 200-10/30 column and eluted fractions that can be seen in FIG. 40A were further analyzed for AID content by western blot (FIG. 40B). The AID protein is concentrated in the pick eluted in fractions 8-10, mainly in fraction 9. This fraction was further analyzed by Coomassie staining after SDS-PAGE resolution (FIG. 40C). The recombinant protein came out not completely purified, but better than before the FPLC procedure.

REFERENCES

Bachl, J. et al. (2001). J Immunol 166, 5051-5057.
Besmer, E. et al. (2006). Molecular and cellular biology 26, 4378-4385.
Fang, J., et al. (2005). Nature biotechnology 23, 584-590.
Lazarides, E., and Lindberg, U. (1974). Proceedings of the National Academy of
Sciences of the United States of America 71, 4742-4746.
Michael, N., et al. (2003). Immunity 19, 235-242.
Muramatsu, M., et al. (2000). Cell 102, 553-563.
Muramatsu, M., et al. (1999) The Journal of biological chemistry 274, 18470-18476.
Ogg, G. S., and McMichael, A. J. (1998). Current opinion in immunology 10, 393-396.
Overwijk, W. et al. (2003). The Journal of experimental medicine 198, 569-580.
Overwijk, W. W., et al. (1998). The Journal of experimental medicine 188, 277-286.
Shen, H. M., P et al. (2009). The Journal of experimental medicine 206, 1057-1071.
Storb, U., S et al. (2007). Advances in experimental medicine and biology 596, 83-91.
Szymczak, A. L., et al. (2010). A The Journal of experimental medicine 207, 405-415.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A method for preparing a T cell comprising an affinity maturated T cell receptor (TCR), the method comprising:
   (i) expressing in a host cell a polycistronic nucleic acid construct comprising a nucleic acid sequence encoding a TCR comprising a TCR alpha chain and a TCR beta chain, wherein said TCR comprises an N-terminal immunoglobulin variable domain, an immunoglobulin constant domain, a transmembrane-spanning region and a cytoplasmic region,
   (ii) mutating said nucleic acid sequence encoding said TCR using somatic hypermutation (SHM),
   (iii) selecting cells expressing a TCR with a higher affinity to a selected ligand compared to said TCR encoded by said nucleic acid construct prior to said (ii),
   (iv) obtaining an expression vector comprising a nucleic acid sequence encoding said TCR with said higher affinity to said selected ligand; and
   (iv) expressing said expression vector in a T cell, wherein said TCR with the higher affinity to said selected ligand functions to initiate an immune response in said T cell when binding said ligand,
   thereby preparing the T cell comprising the affinity maturated TCR.

2. The method of claim 1, wherein said TCR with the higher affinity to said selected ligand exhibits a dissociation constant lower than 50 nanomolar for said selected ligand.

3. A method of treating cancer in a subject in need thereof, the method comprising:
   (a) preparing a T cell comprising an affinity maturated T cell receptor (TCR) according to the method of claim 1, wherein said selected ligand is a cancer antigen-MHC complex; and
   (b) administering to the subject a therapeutically effective amount of said T cell comprising the affinity maturated TCR, wherein the cancer expresses said selected ligand,
   thereby treating the cancer in the subject.

4. The method of claim 3, wherein said cancer is selected from the group consisting of: prostate cancer, breast cancer, skin cancer, colon cancer, lung cancer, pancreatic cancer, head and neck cancer, kidney cancer, ovarian cancer, cervix cancer, bone cancer, liver cancer, thyroid cancer, brain cancer, lymphoma, myeloma and leukemia.

5. The method of claim 3, wherein said cancer is melanoma.

6. The method of claim 3, wherein said T cell is autologous to said subject or a T cell derived from an HLA identical allogeneic donor.

* * * * *

SEQUENCE LISTING

<160> NUMBER OF SEQ ID NOS: 24

<210> SEQ ID NO 1
<211> LENGTH: 804
<212> TYPE: DNA
<213> ORGANISM: Mus musculus

<400> SEQUENCE: 1

```
atgaaatcct tgagtgtttc actagtggtc ctgtggctcc agtttaattg ggtgagaagc      60
cagcagaagg tgcagcagag cccagaatcc ctcactgtct cagagggagc catggcctct     120
ctcaactgca ctttcagtga tcgttcttct gacaacttca ggtggtacag acagcattct     180
gggaaaggcc ttgaggtgct ggtgtccatc ttctctgatg gtgaaaagga agaaggtagt     240
tttacagctc acctcaatag agccagcctg catgttttcc tacacatcag agagccgcaa     300
cccagtgact ctgctctcta cctctgtgca gtgaacacag gaaactacaa atacgtcttt     360
ggagcaggta ccagactgaa ggttatagca cacatccaga acccagaacc tgctgtgtac     420
cagttaaaag atcctcggtc tcaggacagc accctctgcc tgttcaccga ctttgactcc     480
caaatcaatg tgccgaaaac catggaatct ggaacgttca tcactgacaa aactgtgctg     540
gacatgaaag ctatggattc caagagcaat ggggccattg cctggagcaa ccagacaagc     600
ttcacctgcc aagatatctt caaagagacc aacgccacct accccagttc agacgttccc     660
tgtgatgcca cgttgactga gaaaagcttt gaaacagata tgaacctaaa ctttcaaaac     720
ctgtcagtta tgggactccg aatcctcctg ctgaaagtag ccggatttaa cctgctcatg     780
```
acgctgaggc tgtggtccag ctga                                                804

<210> SEQ ID NO 2
<211> LENGTH: 924
<212> TYPE: DNA
<213> ORGANISM: Mus musculus

<400> SEQUENCE: 2
atggccccgc ggcttcttgg ctgggcagtg ttctgtctcc ttgacacagt actgtctgaa     60
gctggagtca cccagtctcc cagatatgca gtcctacagg aagggcaagc tgtttccttt   120
tggtgtgacc ctatttctgg acatgatacc ctttactggt atcagcagcc agagaccag    180
gggcccccagc ttctagttta ctttcgggat gaggctgtta tagataattc acagttgccc   240
tcggatcgat tttctgctgt gaggcctaaa ggaactaact ccactctcaa gatccagtct   300
gcaaagcagg gcgacacagc cacctatctc tgtgccagca gtttccacag ggactataat   360
tcgcccctct actttgcggc aggcaccccg ctcactgtga cagaggatct gagaaatgtg   420
actccaccca aggtctcctt gttttgagcca tcaaaagcag agattgcaaa caaacaaaag   480
gctaccctcg tgtgcttggc caggggcttc ttccctgacc acgtggagtt gagctggtgg   540
gtgaatggca aggaggtcca cagtggggtc agcacggacc ctcaggccta caaggagagc   600
aattatagct actgcctgag cagccgcctg agggtctctg ctaccttctg cacaatcct    660
cgcaaccact ccgctgtca agtgcagttc catgggcttt cagaggagga caagtggcca    720
gagggctcac ccaaacctgt cacacagaac atcagtgcag aggcctgggg ccgagcagac   780
tgtgggatta cctcagcatc ctatcaacaa ggggtcttgt ctgccaccat cctctatgag   840
atcctgctag ggaaagtcac cctgtatgct gtgcttgtca gtacactggt ggtgatggct   900
atggtcaaaa gaaagaattc atga                                            924

<210> SEQ ID NO 3
<211> LENGTH: 597
<212> TYPE: DNA
<213> ORGANISM: Homo sapiens

<400> SEQUENCE: 3
atggacagcc tcttgatgaa ccggaggaag tttctttacc aattcaaaaa tgtccgctgg     60
gctaagggtc ggcgtgagac ctacctgtgc tacgtagtga agaggcgtga cagtgctaca   120
tccttttcac tggactttgg ttatcttcgc aataagaacg gctgccacgt ggaattgctc   180
ttcctccgct acatctcgga ctgggaccta gaccctggcc gctgctaccg cgtcacctgg   240
ttcacctcct ggagcccctg ctacgactgt gcccgacatg tggccgactt ctgcgaggg    300
aaccccaacc tcagtctgag gatcttcacc gcgcgcctct acttctgtga ggaccgcaag   360
gctgagcccg aggggctgcg gcggctgcac cgcgccgggg tgcaaatagc catcatgacc   420
ttcaaagatt attttttactg ctggaatact tttgtagaaa accacgaaag aactttcaaa   480
gcctgggaag gctgcatga aaattcagtt cgtctctcca gacagcttcg gcgcatcctt    540
ttgccccctgt atgaggttga tgacttacga gacgcatttc gtactttggg actttga      597

<210> SEQ ID NO 4
<211> LENGTH: 198
<212> TYPE: PRT
<213> ORGANISM: Homo sapiens

<400> SEQUENCE: 4

Met Asp Ser Leu Leu Met Asn Arg Arg Lys Phe Leu Tyr Gln Phe Lys

```
                1               5                   10                  15
            Asn Val Arg Trp Ala Lys Gly Arg Arg Glu Thr Tyr Leu Cys Tyr Val
                            20                  25                  30
            Val Lys Arg Arg Asp Ser Ala Thr Ser Phe Ser Leu Asp Phe Gly Tyr
                            35                  40                  45
            Leu Arg Asn Lys Asn Gly Cys His Val Glu Leu Phe Leu Arg Tyr
                            50                  55                  60
            Ile Ser Asp Trp Asp Leu Asp Pro Gly Arg Cys Tyr Arg Val Thr Trp
            65                  70                  75                  80
            Phe Thr Ser Trp Ser Pro Cys Tyr Asp Cys Ala Arg His Val Ala Asp
                            85                  90                  95
            Phe Leu Arg Gly Asn Pro Asn Leu Ser Leu Arg Ile Phe Thr Ala Arg
                            100                 105                 110
            Leu Tyr Phe Cys Glu Asp Arg Lys Ala Glu Pro Glu Gly Leu Arg Arg
                            115                 120                 125
            Leu His Arg Ala Gly Val Gln Ile Ala Ile Met Thr Phe Lys Asp Tyr
                            130                 135                 140
            Phe Tyr Cys Trp Asn Thr Phe Val Glu Asn His Glu Arg Thr Phe Lys
            145                 150                 155                 160
            Ala Trp Glu Gly Leu His Glu Asn Ser Val Arg Leu Ser Arg Gln Leu
                            165                 170                 175
            Arg Arg Ile Leu Leu Pro Leu Tyr Glu Val Asp Asp Leu Arg Asp Ala
                            180                 185                 190
            Phe Arg Thr Leu Gly Leu
                            195
```

<210> SEQ ID NO 5
<211> LENGTH: 9
<212> TYPE: PRT
<213> ORGANISM: Artificial
<220> FEATURE:
<223> OTHER INFORMATION: synthitic peptide

<400> SEQUENCE: 5

```
Lys Val Pro Arg Asn Gln Asp Trp Leu
1               5
```

<210> SEQ ID NO 6
<211> LENGTH: 26
<212> TYPE: DNA
<213> ORGANISM: artificial
<220> FEATURE:
<223> OTHER INFORMATION: Synthetic primer

<400> SEQUENCE: 6
cgggatccat ggacagcctc ttgatg                                        26

<210> SEQ ID NO 7
<211> LENGTH: 26
<212> TYPE: DNA
<213> ORGANISM: Artificial
<220> FEATURE:
<223> OTHER INFORMATION: sythetic primer

<400> SEQUENCE: 7
gcgaattctc aaagtcccaa agtacg                                        26

<210> SEQ ID NO 8
<211> LENGTH: 26
<212> TYPE: DNA

<213> ORGANISM: Artificial
<220> FEATURE:
<223> OTHER INFORMATION: synthetic primer

<400> SEQUENCE: 8
cggaattcgc caggatggaa cacagc                                    26

<210> SEQ ID NO 9
<211> LENGTH: 26
<212> TYPE: DNA
<213> ORGANISM: Artificial
<220> FEATURE:
<223> OTHER INFORMATION: synthetic primer

<400> SEQUENCE: 9
atgtcgactt agcgaggggc cagggt                                    26

<210> SEQ ID NO 10
<211> LENGTH: 29
<212> TYPE: DNA
<213> ORGANISM: Artificial
<220> FEATURE:
<223> OTHER INFORMATION: synthetic primer

<400> SEQUENCE: 10
cgcgctctag aatggacagc ctcttgatg                                 29

<210> SEQ ID NO 11
<211> LENGTH: 34
<212> TYPE: DNA
<213> ORGANISM: Artificial
<220> FEATURE:
<223> OTHER INFORMATION: Synthetic primer

<400> SEQUENCE: 11
atagtttagc ggccgctcaa agtcccaaag tacg                           34

<210> SEQ ID NO 12
<211> LENGTH: 46
<212> TYPE: DNA
<213> ORGANISM: Artificial
<220> FEATURE:
<223> OTHER INFORMATION: synthetic primer

<400> SEQUENCE: 12
cgggatccta atacgactca ctatagggat gaaatccttg agtgtt              46

<210> SEQ ID NO 13
<211> LENGTH: 28
<212> TYPE: DNA
<213> ORGANISM: Artificial
<220> FEATURE:
<223> OTHER INFORMATION: synthetic primer

<400> SEQUENCE: 13
acgcgtcgac tcatgaattc tttctttt                                  28

<210> SEQ ID NO 14
<211> LENGTH: 26
<212> TYPE: DNA
<213> ORGANISM: Artificial
<220> FEATURE:
<223> OTHER INFORMATION: Synthetic primer

<400> SEQUENCE: 14
cggtcgacat ggacagcctc ttgatg                                    26

<210> SEQ ID NO 15
<211> LENGTH: 23
<212> TYPE: DNA
<213> ORGANISM: Artificial
<220> FEATURE:
<223> OTHER INFORMATION: synthetic primer

<400> SEQUENCE: 15
gcctcgagaa gtcccaaagt acg                                              23

<210> SEQ ID NO 16
<211> LENGTH: 522
<212> TYPE: DNA
<213> ORGANISM: Mus musculus

<400> SEQUENCE: 16
atggaacaca gcgggattct ggctagtctg atactgattg ctgttctccc ccaagggagc      60
cccttcaaga tacaagtgac cgaatatgag acaaagtat ttgtgacctg caataccagc      120
gtcatgcatc tagatggaac ggtggaagga tggtttgcaa agaataaaac actcaacttg     180
ggcaaaggcg ttctggaccc acgagggata tatctgtgta atgggacaga gcagctggca     240
aaggtggtgt cttctgtgca agtccattac cgaatgtgcc agaactgtgt ggagctagac     300
tcgggcacca tggctggtgt catcttcatt gacctcatcg caactctgct cctggctttg     360
ggcgtctact gctttgcagg acatgagacc ggaaggcctt ctgggctgc tgaggttcaa      420 gcactgctga agaatgagca gctgtatcag cctcttcgag atcgtgaaga tacccagtac     480
agccgtcttg gagggaactg gccccggaac aagaaatctt aa                        522

<210> SEQ ID NO 17
<211> LENGTH: 570
<212> TYPE: DNA
<213> ORGANISM: Mus musculus

<400> SEQUENCE: 17
atgcggtgga acactttctg gggcatcctg tgcctcagcc tcctagctgt tggcacttgc      60
caggacgatg ccgagaacat tgaatacaaa gtctccatct caggaaccag tgtagagttg     120
acgtgccctc tagacagtga cgagaactta aatgggaaa aaaatggcca agagctgcct     180
cagaagcatg ataagcacct ggtgctccag gatttctcgg aagtcgagga cagtggctac     240
tacgtctgct acacaccagc ctcaaataaa aacacgtact gtacctgaa agctcgagtg      300 tgtgagtact gtgtggaggt ggacctgaca gcagtagcca taatcatcat tgttgacatc     360
tgtatcactc tgggcttgct gatggtcatt tattactgga gcaagaatag gaaggccaag     420
gccaagcctg tgacccgagg aaccggtgct ggtagcaggc ccagagggca aaacaaggag     480
cggccaccac ctgttcccaa cccagactat gagcccatcc gcaaaggcca gcgggacctg     540
tattctggcc tgaatcagag agcagtctga                                      570

<210> SEQ ID NO 18
<211> LENGTH: 549
<212> TYPE: DNA
<213> ORGANISM: Mus musculus

<400> SEQUENCE: 18
atggagcaga ggaagggtct ggctggcctc ttcctggtga tctctcttct tcaaggcact      60
gtagcccaga caaataaagc aaagaatttg gtacaagtgg atggcagccg aggagacggt     120

```
tctgtacttc tgacttgtgg cttgactgac aagactatca agtggcttaa agacgggagc    180
ataataagtc ctctaaatgc aactaaaaac acatggaatc tgggcaacaa tgccaaagac    240
cctcgaggca cgtatcagtg tcaaggagca aaggagacat caaaccccct gcaagtgtat    300
tacagaatgt gtgaaaactg cattgagcta acataggca ccatatccgg ctttatcttc     360
gctgaggtca tcagcatctt cttccttgct cttggtgtat atctcattgc gggacaggat    420
ggagttcgcc agtcaagagc ttcagacaag cagactctgt tgcaaaatga acagctgtac    480
cagcccctca aggaccggga atatgaccag tacagccatc tccaaggaaa ccaactgagg    540
aagaagtga                                                            549

<210> SEQ ID NO 19
<211> LENGTH: 495
<212> TYPE: DNA
<213> ORGANISM: Mus musculus

<400> SEQUENCE: 19
atgaagtgga aagtgtctgt tctcgcctgc atcctccacg tgcggttccc aggagcagag     60
gcacagagct ttggtctgct ggatcccaaa ctctgctact tgctagatgg aatcctcttc    120
atctacggag tcatcatcac agccctgtac ctgagagcaa aattcagcag gagtgcagag    180
actgctgcca acctgcagga ccccaaccag ctctacaatg agctcaatct agggcgaaga    240
gaggaatatg acgtcttgga gaagaagcgg gctcgggatc cagagatggg aggcaaacag    300
cagaggagga ggaaccccca ggaaggcgta caatgcac tgcagaaaga caagatggca     360
gaagcctaca gtgagatcgg cacaaaaggc gagaggcgga gaggcaaggg gcacgatggc    420 cttttaccagg gtctcagcac tgccaccaag gacacctatg atgccctgca tatgcagacc    480
ctggcccctc gctaa                                                    495

<210> SEQ ID NO 20
<211> LENGTH: 624
<212> TYPE: DNA
<213> ORGANISM: Homo sapiens

<400> SEQUENCE: 20
atgcagtcgg gcactcactg gagagttctg ggcctctgcc tcttatcagt tggcgtttgg     60
gggcaagatg gtaatgaaga aatgggtggt attacacaga caccatataa agtctccatc    120
tctggaacca cagtaatatt gacatgccct cagtatcctg gatctgaaat actatggcaa    180
cacaatgata aaaacatagg cggtgatgag gatgataaaa acataggcag tgatgaggat    240
cacctgtcac tgaaggaatt ttcagaattg gagcaaagtg gttattatgt ctgctacccc    300
agaggaagca aaccagaaga tgcgaacttt tatctctacc tgagggcaag agtgtgtgag    360
aactgcatgg agatggatgt gatgtcggtg gccacaattg tcatagtgga catctgcatc    420
actgggggct tgctgctgct ggtttactac tggagcaaga tagaaaggc caaggccaag    480 cctgtgacac gaggagcggg tgctggcggc aggcaaaggg gacaaacaa ggagaggcca    540 ccacctgttc ccaacccaga ctatgagccc atccggaaag ccagcgggga cctgtattct    600
ggcctgaatc agagacgcat ctga                                          624

<210> SEQ ID NO 21
<211> LENGTH: 549
<212> TYPE: DNA
<213> ORGANISM: Homo sapiens

<400> SEQUENCE: 21
```

```
atggaacagg ggaagggcct ggctgtcctc atcctggcta tcattcttct tcaaggtact    60
ttggcccagt caatcaaagg aaaccacttg gttaaggtgt atgactatca agaagatggt   120
tcggtacttc tgacttgtga tgcagaagcc aaaaatatca catggtttaa agatgggaag   180
atgatcggct tcctaactga agataaaaaa aatggaatc tgggaagtaa tgccaaggac   240
cctcgaggga tgtatcagtg taaaggatca cagaacaagt caaaaccact ccaagtgtat   300
tacagaatgt gtcagaactg cattgaacta atgcagcca ccatatctgg ctttctcttt   360
gctgaaatcg tcagcatttt cgtccttgct gttggggtct acttcattgc tggacaggat   420
ggagttcgcc agtcgagagc ttcagacaag cagactctgt tgcccaatga ccagctctac   480
cagcccctca aggatcgaga agatgaccag tacagccacc ttcaaggaaa ccagttgagg   540
aggaattga                                                           549
```

<210> SEQ ID NO 22
<211> LENGTH: 549
<212> TYPE: DNA
<213> ORGANISM: Homo sapiens

<400> SEQUENCE: 22

```
atggaacagg ggaagggcct ggctgtcctc atcctggcta tcattcttct tcaaggtact    60
ttggcccagt caatcaaagg aaaccacttg gttaaggtgt atgactatca agaagatggt   120
tcggtacttc tgacttgtga tgcagaagcc aaaaatatca catggtttaa agatgggaag   180
atgatcggct tcctaactga agataaaaaa aatggaatc tgggaagtaa tgccaaggac   240
cctcgaggga tgtatcagtg taaaggatca cagaacaagt caaaaccact ccaagtgtat   300
tacagaatgt gtcagaactg cattgaacta atgcagcca ccatatctgg ctttctcttt   360
gctgaaatcg tcagcatttt cgtccttgct gttggggtct acttcattgc tggacaggat   420
ggagttcgcc agtcgagagc ttcagacaag cagactctgt tgcccaatga ccagctctac   480
cagcccctca aggatcgaga agatgaccag tacagccacc ttcaaggaaa ccagttgagg   540
aggaattga                                                           549
```

<210> SEQ ID NO 23
<211> LENGTH: 492
<212> TYPE: DNA
<213> ORGANISM: Homo sapiens

<400> SEQUENCE: 23

```
atgaagtgga aggcgctttt caccgcggcc atcctgcagg cacagttgcc gattacagag    60
gcacagagct ttggcctgct ggatcccaaa ctctgctacc tgctggatgg aatcctcttc   120
atctatggtg tcattctcac tgccttgttc ctgagagtga agttcagcag gagcgcagag   180
ccccccgcgt accagcaggg ccagaaccag ctctataacg agctcaatct aggacgaaga   240
gaggagtacg atgttttgga caagagacgt ggccgggacc ctgagatggg gggaaagccg   300
agaaggaaga accctcagga aggcctgtac aatgaactgc agaaagataa gatggcggag   360
gcctacagtg agattgggat gaaaggcgag cgccggaggg gcaaggggca cgatggcctt   420
taccagggtc tcagtacagc caccaaggac acctacgacg cccttcacat gcaggccctg   480
ccccctcgct aa                                                       492
```

<210> SEQ ID NO 24
<211> LENGTH: 9
<212> TYPE: PRT

```
<213> ORGANISM: Artificial
<220> FEATURE:
<223> OTHER INFORMATION: Synthetic peptide

<400> SEQUENCE: 24

Glu Gly Ser Arg Asn Gln Asp Trp Leu
1               5
```